US010017768B2

(12) United States Patent
Tsang et al.

(10) Patent No.: US 10,017,768 B2
(45) Date of Patent: Jul. 10, 2018

(54) METHOD OF TREATMENT OF CHLAMYDIAL INFECTIONS WITH SELECTED EGFR INHIBITORS

(71) Applicant: Wake Forest University Health Sciences, Winston-Salem, NC (US)

(72) Inventors: Allen W. Tsang, Clemmons, NC (US); Cristina M. Furdui, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 15/153,401

(22) Filed: May 12, 2016

(65) Prior Publication Data

US 2017/0067059 A1 Mar. 9, 2017

Related U.S. Application Data

(63) Continuation of application No. 14/483,961, filed on Sep. 11, 2014, now abandoned.

(60) Provisional application No. 61/877,898, filed on Sep. 13, 2013.

(51) Int. Cl.
| | |
|---|---|
| *C07K 16/28* | (2006.01) |
| *C07K 16/32* | (2006.01) |
| *A61K 31/517* | (2006.01) |
| *C12N 15/113* | (2010.01) |
| *A61K 31/5377* | (2006.01) |
| *A61K 45/06* | (2006.01) |
| *C12Q 1/6883* | (2018.01) |
| *G01N 33/569* | (2006.01) |
| *A61K 31/712* | (2006.01) |
| *C12Q 1/689* | (2018.01) |
| *G01N 33/68* | (2006.01) |
| *A61K 39/00* | (2006.01) |

(52) U.S. Cl.
CPC ........ *C12N 15/1138* (2013.01); *A61K 31/517* (2013.01); *A61K 31/5377* (2013.01); *A61K 31/712* (2013.01); *A61K 45/06* (2013.01); *C07K 16/2863* (2013.01); *C07K 16/32* (2013.01); *C12Q 1/689* (2013.01); *C12Q 1/6883* (2013.01); *G01N 33/56927* (2013.01); *G01N 33/6893* (2013.01); *A61K 2039/505* (2013.01); *C07K 2317/24* (2013.01); *C07K 2317/76* (2013.01); *C12N 2310/11* (2013.01); *C12N 2320/31* (2013.01); *C12Q 2600/154* (2013.01); *C12Q 2600/158* (2013.01); *G01N 2333/485* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,271,146 A | 6/1981 | Seawell |
| 8,790,649 B2 | 7/2014 | Setiady et al. |
| 8,940,885 B2 | 1/2015 | Gmeiner |
| 2009/0169581 A1 | 7/2009 | Sandrine |

FOREIGN PATENT DOCUMENTS

AU 2011202860 A1 7/2011

OTHER PUBLICATIONS

Amann et al. "Aberrant Epidermal Growth Factor Receptor Signaling and Enhanced Sensitivity to EGFR Inhibitors in Lung Cancer" *Cancer Research* 65(1):226-235 (2005).
Baas et al. "Recommendations on management of EGFR inhibitor-induced skin toxicity: A systematic review" *Cancer Treatment Reviews* 38:505-514 (2012).
Birkelund et al. "*Chlamydia trachomatis* Serovar L2 Induces Protein Tyrosine Phosphorylation during Uptake by HeLa Cells" *Infection and Immunity* 62(11):4900-4908 (1994).
Bjorkelund et al. "Comparing the Epidermal Growth Factor Interaction with Four Different Cell Lines: Intriguing Effects Imply Strong Dependency of Cellular Context" *PLoS ONE* 6(1):e16536 (2011).
Carabeo et al. "*Chlamydia trachomatis* Induces Remodeling of the Actin Cytoskeleton during Attachment and Entry into HeLa Cells" *Infection and Immunity* 70(7):3793-3803 (2002).
Chung et al. "Spatial control of EGF receptor activation by reversible dimerization on living cells" *Nature* 464:783-788 (2010).
Clifton et al. "A chlamydial type III translocated protein is tyrosine-phosphorylated at the site of entry and associated with recruitment of actin" *Proceedings of the National Academy of Sciences* 101(27):10166-10171 (2004).
Clifton et al. "Tyrosine Phosphorylation of the Chlamydial Effector Protein Tarp Is Species Specific and Not Required for Recruitment of Actin" Infection and Immunity 73(7):3860-3868 (2005).
De Clercq et al. "Animal Models for Studying Female Genital Infection with *Chlamydia trachomatis*" *Infection and Immunity* 81(9):3060-3067 (2013).
Den Hartigh et al. "The EGF Receptor is an Actin-binding Protein" *The Journal of Cell Biology* 119(2):349-355 (1992).
Fawaz et al. "Infection with *Chlamydia trachomatis* Alters the Tyrosine Phosphorylation and/or Localization of Several Host Cell Proteins Including Cortactin" *Infection and Immunity* 65(12):5301-5308 (1997).
Gan et al. "The Epidermal Growth Factor Receptor (EGFR) Tyrosine Kinase Inhibitor AG1478 Increases the Formation of Inactive Untethered EGFR Dimers" *The Journal of Biological Chemistry* 282(5):2840-2850 (2007).
Hafner et al. "*Chlamydia trachomatis* infection: host immune responses and potential vaccines" *Mucosal Immunology* 1(2):116-130 (2008).

(Continued)

*Primary Examiner* — Elly-Gerald Stoica
(74) *Attorney, Agent, or Firm* — Myers Bigel, P.A.

(57) ABSTRACT

The present invention provides compositions and methods of use in the treatment/prevention of chlamydial infection and/or diseases and disorders associated with chlamydial infection in a subject.

2 Claims, 36 Drawing Sheets

(56) References Cited

OTHER PUBLICATIONS

Hung et al. "Nuclear epidermal growth factor receptor (EGFR) interacts with signal transducer and activator of transcription 5 (STAT5) in activating *Aurora-A* gene expression" *Nucleic Acids Research* 36(13):4337-4351 (2008).
Hurley et al. "Translating tissue culture results into animal models: the case of *Salmonella typhimurium*" *TRENDS in Microbiology* 11(12):562-569 (2003).
International Preliminary Report on Patentability corresponding to International Application No. PCT/US2014/055167 (7 pages) (dated Mar. 15, 2016).
International Search Report and the Written Opinion of the International Searching Authority corresponding to International Application No. PCT/US2014/055167 (11 pages) (dated Dec. 23, 2014).
Iyer et al. "A review of erlotinib—an oral, selective epidermal growth factor receptor tyrosine kinase inhibitor" *Expert Opinion on Pharmacotherapy* 11(2):311-320 (2010).
Jin et al. "Effect of an epidermal growth factor receptor tyrosine kinase inhibitor on actin remodeling in an in vitro bladder cancer carcinogenesis model" *Molecular Cancer Therapeutics* 5(7):1754-1763 (2006).
Kim et al. "*Chlamydia trachomatis* Co-opts the FGF2 Signaling Pathway to Enhance Infection" *PLoS Pathogens* 7(10):e1002285 (2011).
Krüll et al. "Signal Transduction Pathways Activated in Endothelial Cells Following Infection with *Chlamydia pneumoniae*" *The Journal of Immunology* 162:4834-4841 (1999).
Kumar et al. "Actin and intermediate filaments stabilize the *Chlamydia trachomatis* vacuole by forming dynamic structural scaffolds" *Cell Host & Microbe* 4(2):1-23 (2008).
Lo et al. "Nuclear EGFR signalling network in cancers: linking EGFR pathway to cell cycle progression, nitric oxide pathway and patient survival" *British Journal of Cancer* 94:184-188 (2006).
Lui et al. "Mitogenic effects of gastrin-releasing peptide in head and neck squamous cancer cells are mediated by activation of the epidermal growth factor receptor" *Oncogene* 22:6183-6193 (2003).
Majeed et al. "Roles of $Ca^{2+}$ and F-Actin in Intracellular Aggregation of *Chlamydia trachomatis* in Eucaryotic Cells" *Infection and Immunity* 61(4):1406-1414 (1993).
Mehlitz et al. "Tarp regulates early *Chlamydia*-induced host cell survival through interactions with the human adaptor protein SHC1" *The Journal of Cell Biology* 190:143-157 (2010).
Mölleken et al. "The *Chlamydia pneumoniae* Invasin Protein Pmp21 Recruits the EGF Receptor for Host Cell Entry" *PLOS Pathogens* 9(4):e1003325 (2013).
Patel et al. "Activation of epidermal growth factor receptor is required for *Chlamydia trachomatis* development" *BMC Microbiology* 14(277):1-20 (2014).
Perez-Soler, Roman "Rash as a Surrogate Marker for Efficacy of Epidermal Growth Factor Receptor Inhibitors in Lung Cancer" *Clinical Lung Cancer* 8(Suppl. 1):S7-S14 (2006).
Peters et al. "Oral epidermal growth factor receptor tyrosine kinase inhibitors for the treatment of non-small cell lung cancer: Comparative pharmacokinetics and drug-drug interactions" *Cancer Treatment Reviews* 40:917-926 (2014).
Rolfo et al. "Novel therapeutic strategies for patients with NSCLC that do not respond to treatment with EGFR inhibitors" *Cancer Treatment Reviews* 40:990-1004 (2014).
Song et al. "Epidermal growth factor induces changes of interaction between epidermal growth factor receptor and actin in intact cells" *Acta Biochimica et Biophysica Sinica* 40(8):754-760 (2008).
Stoorvogel et al. "Sorting of Ligand-activated Epidermal Growth Factor Receptor Lysosomes Requires Its Actin-binding Domain" *The Journal of Biological Chemistry* 279(12):11562-11569 (2004).
Subtil et al. "Analysis of *Chlamydia caviae* entry sites and involvement of Cdc42 and Rac activity" *Journal of Cell Science* 117(17):3923-3933 (2004).
Tang et al. "Regulated EGF receptor binding to F-actin modulates receptor Phosphorylation" *Biochemical and Biophysical Research Communications* 312:930-936 (2003).
Yi et al. "Inhibition of the EGF-induced activation of phospholipase C-γ1 by a single chain antibody fragment" *Oncogene* 20:7954-7964 (2001).
Zhang et al. "Role of EGFR Transactivation in Preventing Apoptosis in *Pseudomonas aeruginosa*-Infected Human Corneal Epithelial Cells" *Investigative Ophthalmology & Visual Science* 45(8):2569-2576 (2004).
Extended European Search Report corresponding to related European Patent Application No. 14843533.2 (15 pages) (dated Feb. 1, 2017).
Elwell et al. "RNA Interference Screen Identifies Abl Kinase and PDGFR Signaling in *Chlamydia trachomatis* Entry" *PLoS Pathogens* 4(3):e1000021 (2008).

*Total time for Ct infection was 24 h

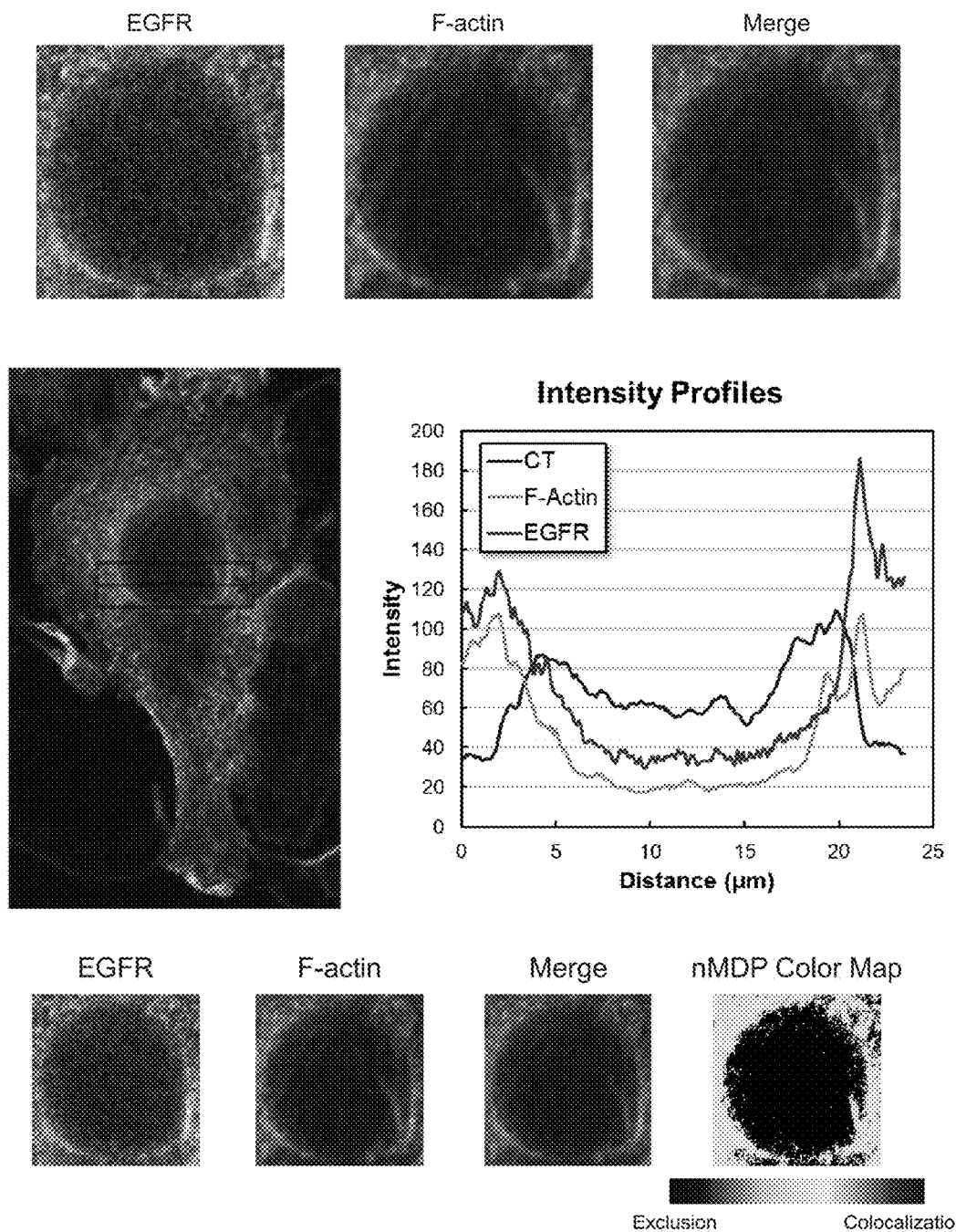
FIG. 24 (Ct infected HeLa cell #1)

| Colocalization Parameter | Range | Value | % Colocalization |
|---|---|---|---|
| Pearson's Coefficient | -1:1 | 0.734 | 73.4 |
| Icorr | -1:1 | 0.840 | 84.0 |
| Manders' EGFR/F-actin | 0:1 | 0.714 | 71.4 |
| Manders' F-actin/EGFR | | 0.773 | 77.3 |
| Li's ICQ | -0.5:0.5 | 0.334 | 66.8 |

FIG. 24 (Cont'd.)

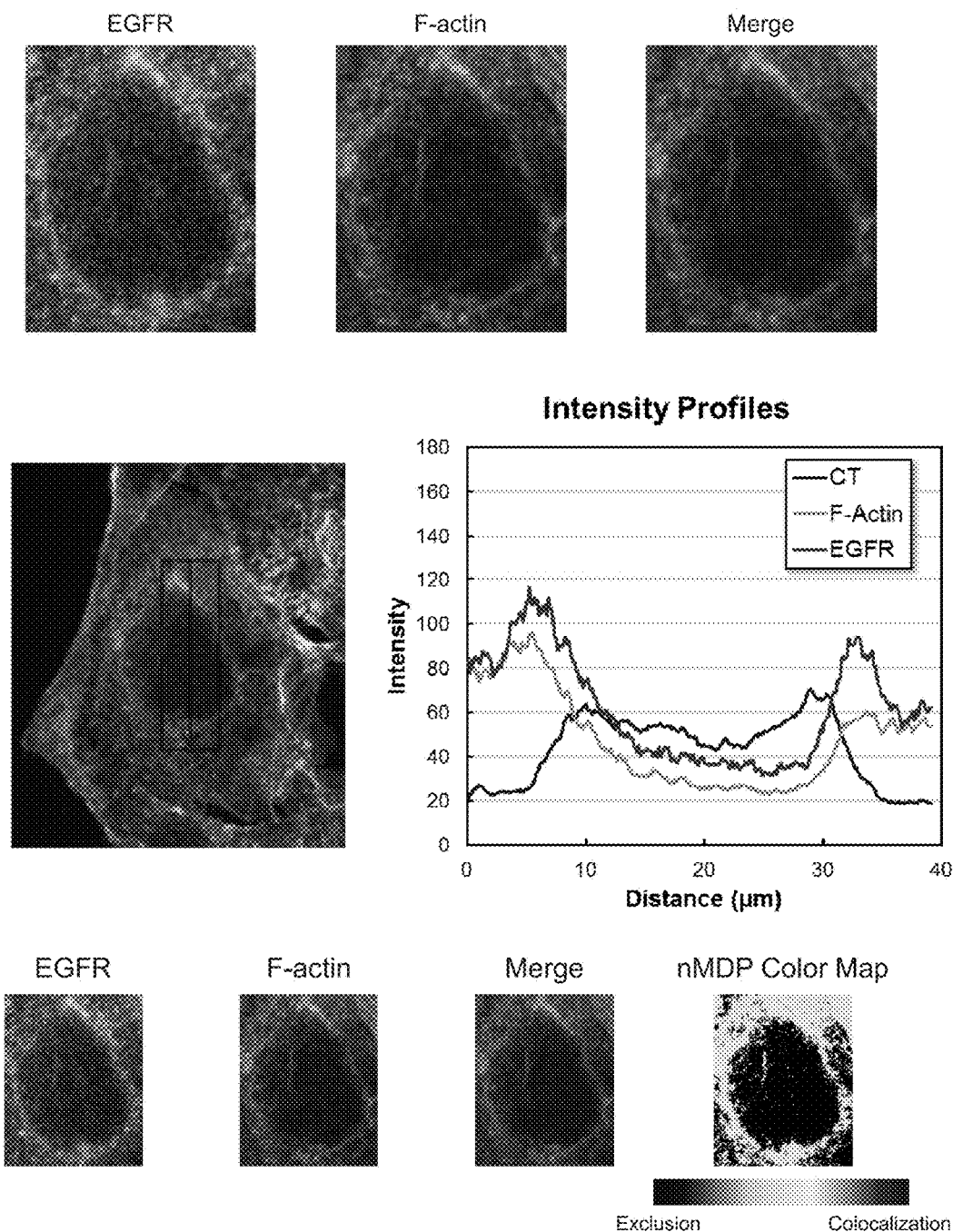
FIG. 25 (Ct infected HeLa cell #2)

| Colocalization Parameter | Range | Value | % Colocalization |
|---|---|---|---|
| Pearson's Coefficient | -1:1 | 0.690 | 69.0 |
| Icorr | -1:1 | 0.786 | 78.6 |
| Manders' EGFR/F-actin | 0:1 | 0.683 | 68.3 |
| Manders' F-actin/EGFR | 0:1 | 0.724 | 72.4 |
| Li's ICQ | -0.5:0.5 | 0.279 | 55.8 |

FIG. 25 (Cont'd.)

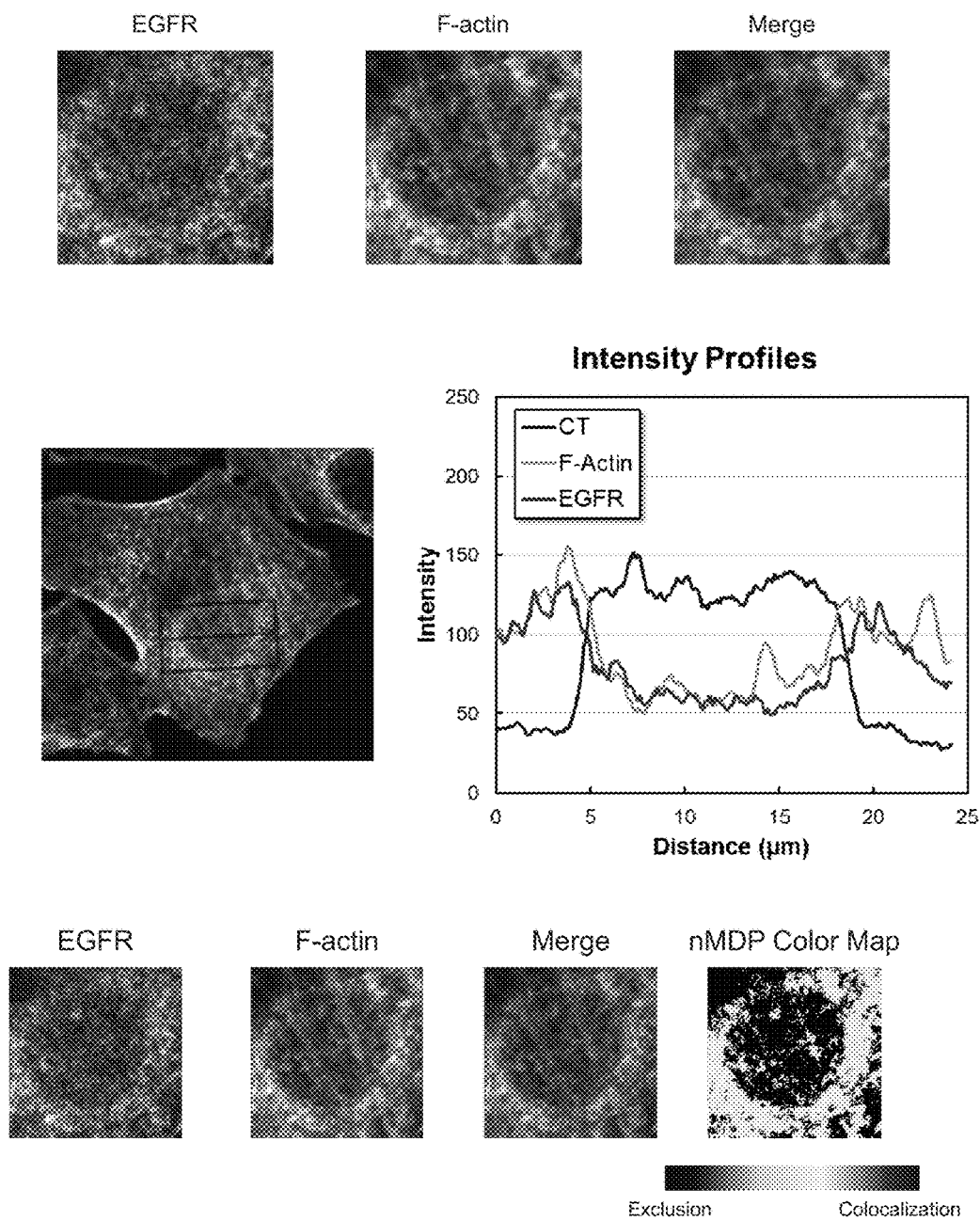
FIG. 26 (Ct infected HeLa cell #3)

| Colocalization Parameter | Range | Value | % Colocalization |
|---|---|---|---|
| Pearson's Coefficient | -1:1 | 0.604 | 60.4 |
| Icorr | -1:1 | 0.721 | 72.1 |
| Manders EGFR/F-actin | 0:1 | 0.669 | 66.9 |
| Manders F-actin/EGFR | | 0.645 | 64.5 |
| Li's ICQ | -0.5:0.5 | 0.217 | 43.4 |

FIG. 26 (Cont'd.)

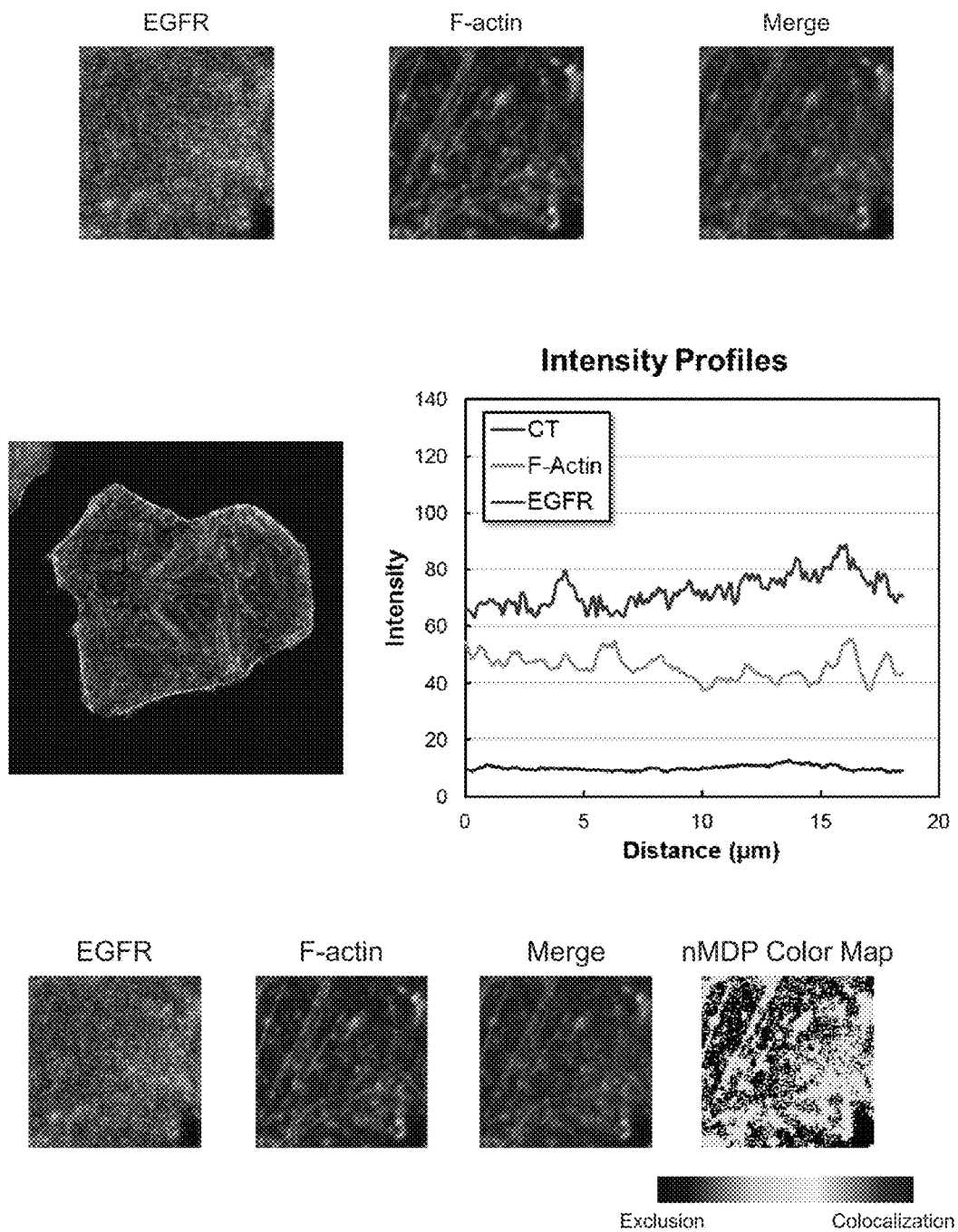
FIG. 27 (Uninfected HeLa cell #1)

| Colocalization Parameter | Range | Value | % Colocalization |
|---|---|---|---|
| Pearson's Coefficient | -1:1 | 0.265 | 26.5 |
| Icorr | -1:1 | 0.584 | 58.4 |
| Manders' EGFR/F-actin | 0:1 | 0.366 | 36.6 |
| Manders' F-actin/EGFR | 0:1 | 0.525 | 52.5 |
| Li's ICQ | -0.5:0.5 | 0.082 | 16.4 |

FIG. 27 (Cont'd.)

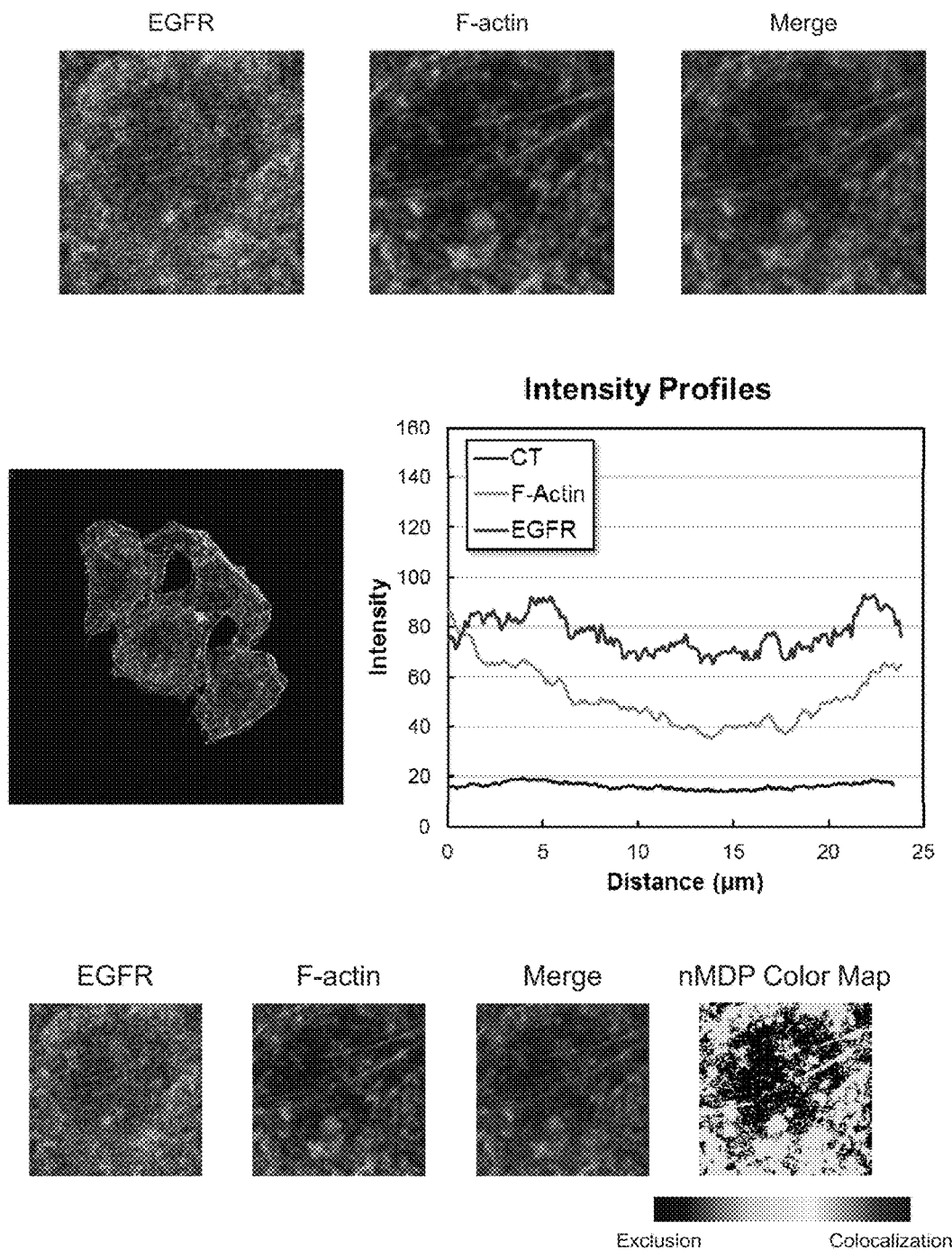
FIG. 28 (Uninfected HeLa cell #2)

| Colocalization Parameter | Range | Value | % Colocalization |
|---|---|---|---|
| Pearson's Coefficient | -1:1 | 0.346 | 34.6 |
| Icorr | -1:1 | 0.629 | 62.9 |
| Manders' EGFR/F-actin | 0:1 | 0.505 | 50.5 |
| Manders' F-actin/EGFR | 0:1 | 0.560 | 56.0 |
| Li's ICQ | -0.5:0.5 | 0.125 | 25.0 |

FIG. 28 (Cont'd.)

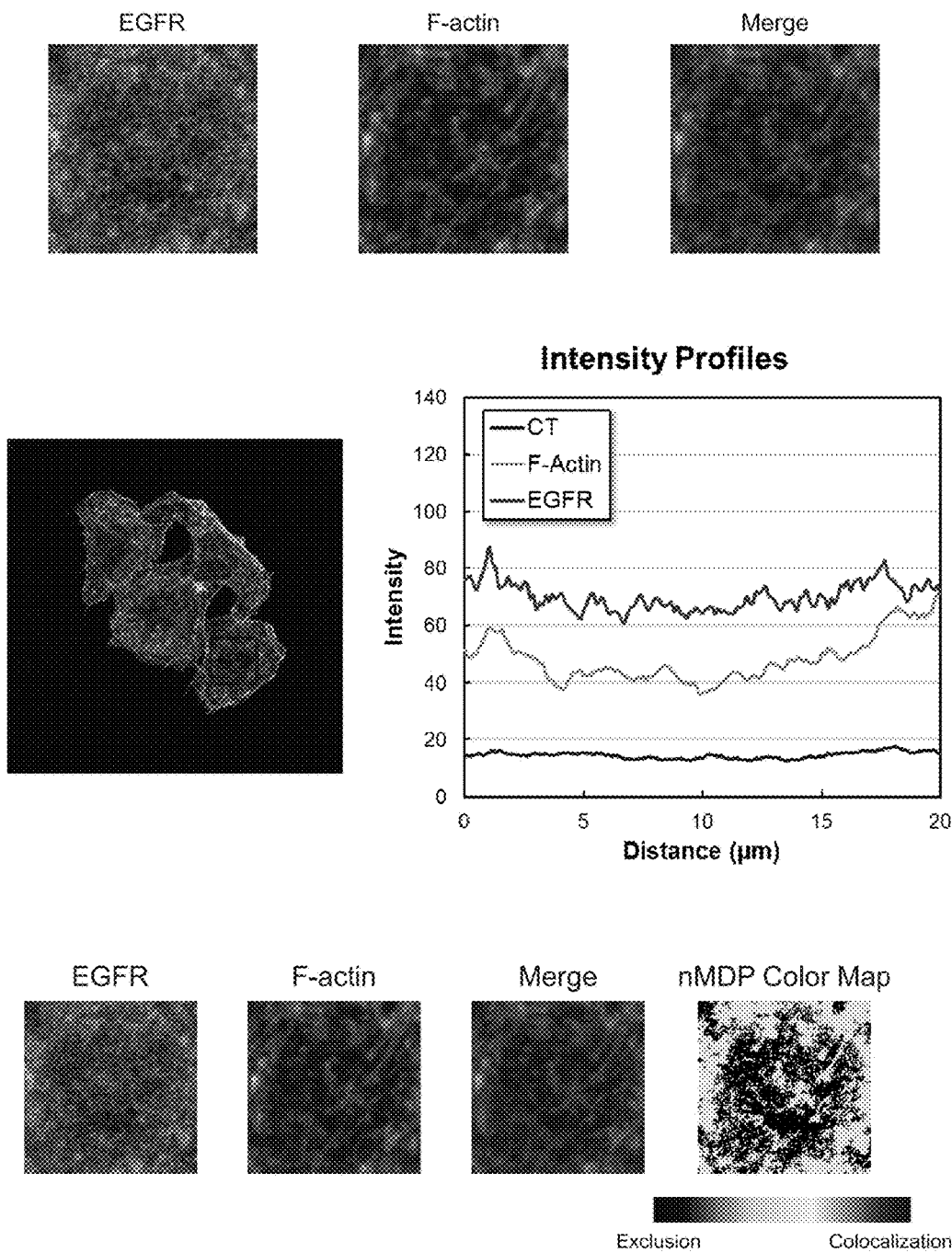
FIG. 29 (Uninfected HeLa cell #3)

| Colocalization Parameter | Range | Value | % Colocalization |
|---|---|---|---|
| Pearson's Coefficient | -1:1 | 0.358 | 35.8 |
| Icorr | -1:1 | 0.623 | 62.3 |
| Manders' EGFR/F-actin | 0:1 | 0.485 | 48.5 |
| Manders' F-actin/EGFR | | 0.569 | 56.9 |
| Li's ICQ | -0.5:0.5 | 0.122 | 24.4 |

FIG. 29 (Cont'd.)

METHOD OF TREATMENT OF CHLAMYDIAL INFECTIONS WITH SELECTED EGFR INHIBITORS

STATEMENT OF PRIORITY

This application is a continuation application of, and claims priority to, U.S. application Ser. No. 14/483,961 filed Sep. 11, 2014, which claims the benefit, under 35 U.S.C. § 119(e), of U.S. Provisional Application Ser. No. 61/877,898, filed Sep. 13, 2013, the entire contents of each of which are incorporated by reference herein.

BACKGROUND OF THE INVENTION

Field of the Invention

The present invention relates to treatment/prevention of chlamydial infection and diseases and disorders associated with *Chlamydia* infection.

Background Art

*Chlamydia* is one of the most common sexually transmitted pathogens in the world, causing an estimated 92 million infections per year, with over 2.8 million infections in the US alone. The rate for chlamydial infection is 3.3 times higher in women than it is in men. It is estimated that nearly 3 million Americans are infected annually costing >$4 billion in healthcare. Most infected people have no symptoms. However, untreated infections can cause numerous diseases such as infertility, osteoporosis, reactive arthritis, Alzheimer's disease, pelvic inflammatory disease and others. In addition, numerous epidemiological studies have shown a positive association between *Chlamydia* infections and the presence of premalignant or invasive cancers.

Currently there is no mechanism-based treatment of *Chlamydia* infections and *Chlamydia*-related diseases. Commonly used antibiotics can stop acute infections with *Chlamydia*; however, this treatment can also cause *Chlamydia* to change into a persistent state, a stealth mode underlying a chronic infection that can lead to *Chlamydia* associated diseases. In addition, during the last 30 years, attempts to create an effective *Chlamydia* vaccine have proven unsuccessful. Thus, the identification of chlamydial or host cell proteins that *Chlamydia* rely on for development in infected tissue is useful for development of effective therapeutics against this pathogen.

The present invention overcomes previous shortcomings in the art by providing methods and compositions employing inhibitors of epidermal growth factor receptor (EGFR) for the treatment and/or prevention of chlamydial infection and *Chlamydia*-associated diseases and disorders.

SUMMARY OF THE INVENTION

In one aspect the present invention provides a method of treating chlamydial infection and/or treating and/or preventing a disease or disorder caused by or associated with chlamydial infection in a subject, comprising administering to the subject an effective amount of an inhibitor of epidermal growth factor receptor (EGFR) expression and/or activity.

In a further aspect, the present invention provides a method of delivering an agent of interest to a cell that expresses EGFR, comprising contacting the cell with a genetically modified *Chlamydia* organism comprising the agent of interest under conditions whereby the *Chlamydia* organism binds the EGFR on the cell, thereby delivering the agent of interest to the cell.

In addition, the present invention provides a method of identifying a substance that inhibits the binding of EGFR to F-actin, comprising: a) contacting the substance with EGFR and F-actin under conditions whereby binding of EGFR and F-actin can occur; and b) assaying for the formation of an EGFR/F-actin binding complex, wherein the absence of formation of an EGFR/F-actin binding complex identifies the substance as a substance that inhibits the binding of EGFR to F-actin.

In another aspect, the present invention provides a method of identifying a subject as having an infection caused by *Chlamydia* or as having had an infection caused by *Chlamydia*, comprising: a) obtaining a biological sample from the subject; and b) assaying the sample of (a) for one or more proteins that are altered due to *Chlamydia* infection in the subject; wherein altered is defined as a decrease or increase in the amount of the protein(s) of (b), and/or as a decrease or increase or change in posttranslational modification (e.g., phosphorylation, oxidation, etc.) of the protein(s) and/or as a decrease or increase in activity of the protein(s), and wherein detection of an alteration in the protein(s) of (b) relative to a control (e.g., proteins assayed in a biological sample from a subject that does not have an infection caused by *Chlamydia* and/or that has not had an infection caused by *Chlamydia*) identifies the subject as having an infection caused by *Chlamydia* or as having had an infection caused by *Chlamydia*.

Additionally provided herein is a method of identifying a subject as having an increased likelihood of having or developing a disease or disorder associated with infection caused by *Chlamydia*, comprising: a) obtaining a biological sample from the subject; and b) assaying the sample of (a) for one or more proteins that are altered due to *Chlamydia* infection in the subject; wherein altered is defined as a decrease or increase in the amount of the protein(s) of (b), and/or as a decrease or increase or change in posttranslational modification (e.g., phosphorylation, oxidation, etc.) of the protein(s) and/or as a decrease or increase in activity of the protein(s), and wherein detection of an alteration in the protein(s) of (b) relative to a control identifies the subject as having an increased likelihood of having or developing a disorder associated with infection caused by *Chlamydia*.

A further aspect of the present invention is a method of identifying a subject for whom prophylactic treatment for a disease or disorder associated with infection caused by *Chlamydia* is indicated, comprising: a) obtaining a biological sample from the subject; and b) assaying the sample of (a) for one or more proteins that are altered due to *Chlamydia* infection in the subject; wherein altered is defined as a decrease or increase in the amount of the protein(s) of (b), and/or as a decrease or increase or change in posttranslational modification (e.g., phosphorylation, oxidation, etc.) of the protein(s) and/or as a decrease or increase in activity of the protein(s), and wherein detection of an alteration in the protein(s) of (b) relative to a control identifies the subject as a subject for whom prophylactic treatment for a disease or disorder associated with infection caused by *Chlamydia* is indicated.

The present invention also provides a method of guiding a treatment regimen for a subject being treated for a disease or disorder associated with infection caused by *Chlamydia*, comprising: a) obtaining a first biological sample from the subject prior to or during treatment; b) assaying the first biological sample for one or more proteins that are altered due to *Chlamydia* infection in the subject, wherein altered is defined as a decrease or increase in the amount of the protein(s) of (b), and/or as a decrease or increase or change in posttranslational modification (e.g., phosphorylation, oxidation, etc.) of the protein(s) and/or as a decrease or increase in activity of the protein(s); c) obtaining a second biological sample from the subject at a subsequent time point during treatment; d) assaying the second biological sample for the same one or more proteins that are altered due to *Chlamydia* infection in the subject; and e) comparing the altered proteins assayed in (b) with the amount and/or degree of alteration of the same altered proteins assayed in (d), wherein a change in amount and/or degree of the alteration of the proteins assayed in (d) relative to the proteins assayed in (b) indicates whether the treatment regimen should be continued and/or increased or discontinued and/or decreased.

Furthermore, the present invention provides a method of identifying a subject as having an infection caused by *Chlamydia* or as having had an infection caused by *Chlamydia*, comprising: a) obtaining a biological sample from the subject; and b) measuring in the sample of (a) methylation at specific DNA CpG sites that are altered due to *Chlamydia* infection in the subject; wherein altered is defined as a decrease or increase in the amount of methylation of (b) in the sample relative to a control, and wherein detection of alteration of methylation at specific DNA CpG sites relative to control identifies the subject as having an infection caused by *Chlamydia* or as having had an infection caused by *Chlamydia*.

In additional embodiments, the present invention provides a method of identifying a subject as having an increased likelihood of having or developing a disease or disorder associated with infection caused by *Chlamydia*, comprising: a) obtaining a biological sample from the subject; and b) measuring in the sample of (a) methylation at specific DNA CpG sites that are altered due to *Chlamydia* infection in the subject, wherein altered is defined as a decrease or increase in the amount of methylation of (b) in the sample relative to a control, and wherein detection of alteration of methylation at specific DNA CpG sites relative to control identifies the subject as having an increased likelihood of having or developing a disorder associated with infection caused by *Chlamydia*.

In addition, the present invention provides a method of identifying a subject for whom prophylactic treatment for a disease or disorder associated with infection caused by *Chlamydia* is indicated, comprising: a) obtaining a biological sample from the subject; and b) measuring in the sample of (a) methylation at specific DNA CpG sites that are altered due to *Chlamydia* infection in the subject, wherein altered is defined as a decrease or increase in the amount of methylation of (b) in the sample relative to a control and wherein detection of alteration of methylation at specific DNA CpG sites relative to control identifies the subject as a subject for whom prophylactic treatment for a disorder associated with infection caused by *Chlamydia* is indicated. As a further aspect, the present invention provides a method of guiding a treatment regimen for a subject being treated for a disease or disorder associated with infection caused by *Chlamydia*, comprising: a) obtaining a first biological sample from the subject prior to or during treatment; b) measuring in the first biological sample the amount of methylation at specific DNA CpG sites that are altered due to *Chlamydia* infection in the subject; c) obtaining a second biological sample from the subject at a subsequent time point during treatment; d) measuring in the second biological sample the amount of methylation at specific DNA CpG sites that are altered due to *Chlamydia* infection in the subject; and e) comparing the amount of altered methylation as measured in (b) with the amount of altered methylation at the same sites as measured in (d), wherein a change in the amount of methylation measured in (d) relative to the amount of methylation measured in (b) indicates whether the treatment regimen should be continued and/or increased or discontinued and/or decreased.

DETAILED DESCRIPTION OF THE INVENTION

Figure 1:
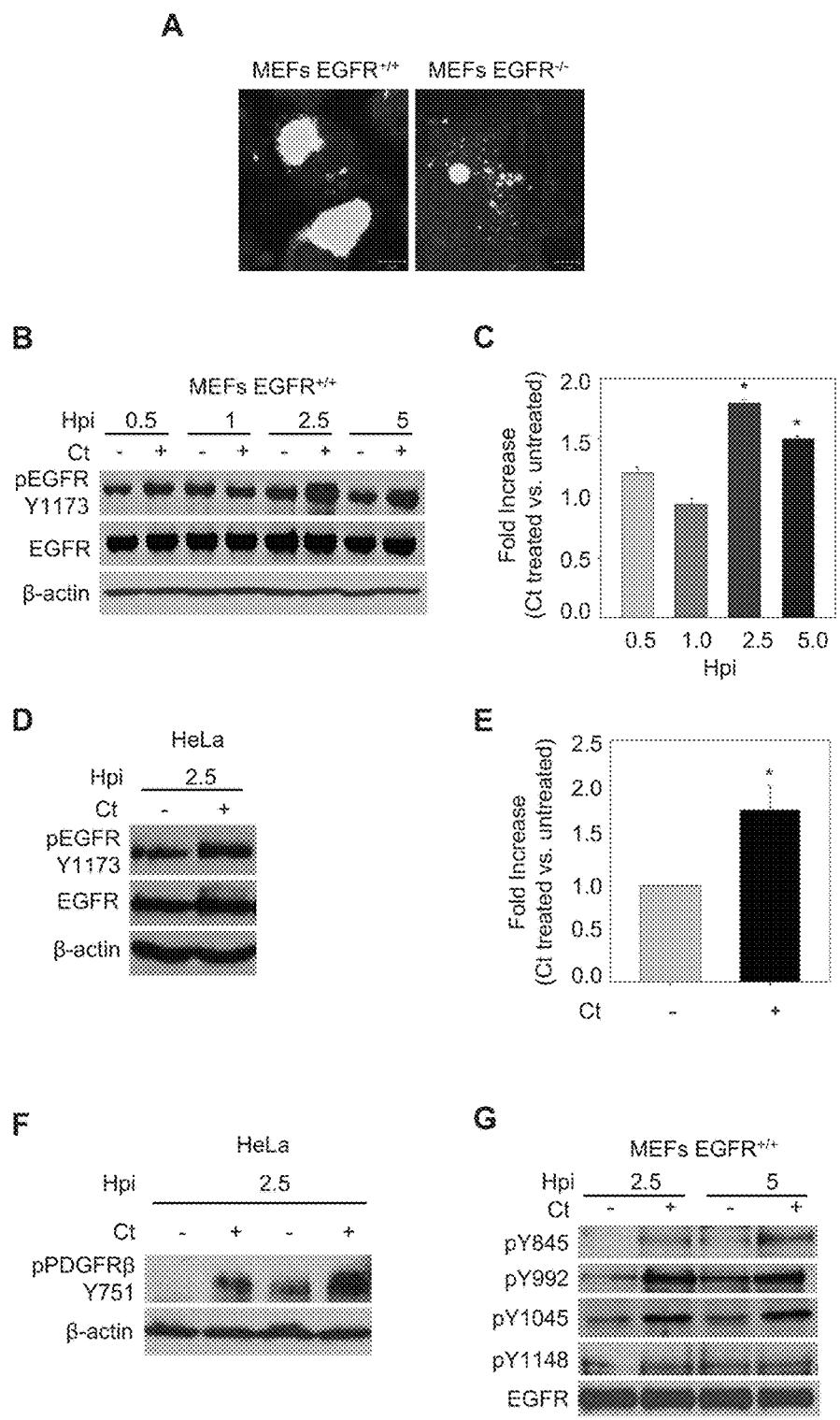
FIG. 1. EGFR is activated by *C. trachomatis* infection. (Panel A) MEFs EGFR$^{+/+}$ and MEFs EGFR$^{-/-}$ cells were infected with *C. trachomatis* (Ct). Note the small chlamydial inclusions formed in the MEFs EGFR$^{-/-}$ cells in comparison to the inclusions formed in MEFs EGFR$^{+/+}$ cells. (Panels B-F) Phosphorylation of EGFR in *C. trachomatis*-infected cells. Monolayers of MEFs EGFR$^{+/+}$ (Panel B) and HeLa (Panel D) with and without chlamydial infection were lysed at different hours post-infection (hpi) as indicated and immunoblotted with antibodies against pY1173-EGFR and EGFR. The immunoblots from three independent experiments were quantified for both MEFs (Panel C) and HeLa cells (Panel E) after normalization with β-actin used as loading control. A significant increase (P<0.05) in phosphorylation of EGFR in MEFs EGFR$^{+/+}$ (Panel C) and HeLa cells (Panel E) was observed at 2.5 hpi. (Panel F) HeLa cells with and without chlamydial infection were lysed at 2.5 hpi. Two biological replicates were subjected to immunoblotting for pPDFGRβ (Y751) and β-actin as loading control. An increase in PDGFRβ phosphorylation was observed in *C. trachomatis*-infected cells compared with non-infected cells. (Panel G) MEFs EGFR$^{+/+}$ were infected with *C. trachomatis* for 2.5 h or 5 h. Western blotting was performed for comparing EGFR phosphorylation by *C. trachomatis* at various tyrosine residues. *C. trachomatis* induced phosphorylation was observed at all sites analyzed with the exception of Y1148 site FIG. 2. *C. trachomatis* activates EGFR downstream signaling. (Panel A) Monolayers of MEFs EFGR$^{+/+}$ and (Panel C) MEFs EGFR$^{-/-}$ cells with and without chlamydial infection were lysed at 2.5, 5, 10 and 18 hpi. Cell lysates were immunoblotted with antibodies against phosphorylated and total EGFR, PLCγ1, Akt and STAT5. β-actin was used as loading control. Each phosphorylated protein was first normalized against the total protein and then the fold increase from –Ct to +Ct was calculated from three independent experiments (Panel B). An increased phosphorylation of EGFR, PLCγ1, Akt and STAT5 was observed in MEFs EGFR$^{+/+}$ (P<0.05) while no change was observed in the MEFs EGFR$^{-/-}$ upon *C. trachomatis* infection.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

The present invention is based on the unexpected discovery that epidermal growth factor receptor (EGFR) is involved in attachment and development of *Chlamydia* to and within, respectively, human cells during chlamydial infection. Thus, in one embodiment, the present invention provides a method of treating chlamydial infection and/or treating and/or preventing a disease or disorder caused by or associated with chlamydial infection in a subject, comprising administering to the subject an effective amount of an inhibitor of epidermal growth factor receptor (EGFR) expression and/or activity.

In the methods of this invention, the inhibitor of EGFR expression and/or activity can be, but is not limited to, an antibody (e.g., Cetuximab, Panitumumab, h-R3 (Nimotuzumab), EMD-72000 (Matuzumab), Zalutumab, MDX-447, mAb-806), a tyrosine kinase based inhibitor (e.g., Erlotinib, Gefitinib, Lapatinib, Canertinib, vandetanib), an antisense oligonucleotide based inhibitor (e.g., GEM231), FR18, an antibody or small molecule that targets the F-actin binding domain of EGFR, or any combination of the above. Also included in this invention is any other inhibitor of EGFR expression and/or activity now known or later identified.

In the methods of this invention, an agent that inhibits binding and/or interaction of a *Chlamydia* organism with EGFR on a cell can also be employed. Nonlimiting examples of an inhibitor of this binding or interaction include an antibody or small molecule that targets a chlamydial protein and prevents or interferes with the binding of a *Chlamydia* organism to EGFR on a cell. Nonlimiting examples of a *Chlamydia* protein that can be targeted for binding include a surface membrane protein (e.g., OmcB), a polymorphic membrane protein (Pmps), and/or a major outer membrane protein (MOMP).

Furthermore, nonlimiting examples of a disease or disorder caused by or associated with chlamydial infection include cancer (e.g., lung, breast, cervical, head and neck, ovarian, etc.), infertility, osteoporosis, arthritis, Alzheimer's disease, pelvic inflammatory disease, asthma, atherosclerosis, chronic fatigue syndrome, chronic obstructive pulmonary disease, coronary heart disease, metabolic syndrome, multiple sclerosis, myocardial infarction, stroke, Tourette syndrome, and any combination thereof.

In some embodiments, the methods of this invention can further comprise administering to the subject an antibiotic, a chemotherapeutic agent, an anti-inflammatory agent, an immunomodulatory agent and/or radiation, in any combination.

The present invention also provides a method of delivering an agent of interest to a cell that expresses EGFR, comprising contacting the cell with a genetically modified *Chlamydia* organism comprising the agent of interest under conditions whereby the *Chlamydia* organism binds the EGFR on the cell, thereby delivering the agent of interest to the cell. By "genetically modified," it is meant that the *Chlamydia* organism has been mutated to render ii capable of infection of a cell but not capable of further development in the cell; i.e., it is not pathogenic. In some embodiments, a nucleotide sequence encoding the agent of interest is introduced into the mutant *Chlamydia*. Nonlimiting examples of an agent of interest of this invention include a nucleic acid molecule, a protein, a drug, a small molecule, an imaging agent, a therapeutic agent and any combination thereof. As one nonlimiting example, genetically modified *Chlamydia* particles could be used for both sequential and site-specific delivery technique. The *Chlamydia* particles first deliver TNF-related apoptosis-inducing ligand (TRAIL) to cancer cell membranes, e.g., to induce cell death and then penetrate the membrane to deliver the chemotherapeutic doxorubicin (Dox) to the nucleus. The sequential combination of TRAIL and Dox may also produce an additive or synergistic effect.

In further embodiments, the present invention provides a method of identifying a substance that inhibits the binding of EGFR to F-actin, comprising: a) contacting the substance with EGFR and F-actin under conditions whereby binding of EGFR and F-actin can occur; and b) assaying for the formation of an EGFR/F-actin binding complex, wherein the absence of formation of an EGFR/F-actin binding complex identifies the substance as a substance that inhibits the binding of EGFR to F-actin. Such a substance can be employed in the methods of this invention as an inhibitor of EGFR activity.

As one nonlimiting example, the method of identifying a substance that inhibits the binding of EGFR to F-actin can be an in vitro binding assay using recombinant EGFR and actin. Actin polymerizes into F-actin in vitro and can be separated from the soluble mixture by centrifugation. The ratio of soluble to F-actin bound EGFR can be used to quantify the inhibition of binding by substances of interest. This assay could be coupled with high-throughput screening of chemical libraries to find a "hit"; i.e., a chemical with an appropriate affinity to the EGFR-actin binding domains that could be developed into a drug.

The present invention also provides a method of identifying a subject as having an infection caused by *Chlamydia* or as having had an infection caused by *Chlamydia*, comprising: a) obtaining a biological sample from the subject; and b) assaying the sample of (a) for one or more proteins that are altered due to *Chlamydia* infection in the subject; wherein altered is defined as a decrease or increase in the amount of the protein(s), and/or as a decrease or increase or change in the posttranslational modification of the protein(s) and/or as a decrease or increase in activity of the protein(s), and wherein detection of an alteration in the protein(s) relative to a control identifies the subject as having an infection caused by *Chlamydia* or as having had an infection caused by *Chlamydia*.

The present invention also provides a method of identifying a subject as having an increased likelihood of having or developing a disease or disorder associated with infection caused by *Chlamydia*, comprising: a) obtaining a biological sample from the subject; and b) assaying the sample of (a) for one or more proteins that are altered due to *Chlamydia* infection in the subject; wherein altered is defined as a decrease or increase in the amount of the protein(s) of (b), and/or as a decrease or increase or change in its posttranslational modification (e.g., phosphorylation, oxidation, etc.) and/or as a decrease or increase in activity of the one or more proteins, and wherein detection of an alteration in the protein(s) of (b) relative to a control identifies the subject as having an increased likelihood of having or developing a disorder associated with infection caused by *Chlamydia*.

Additionally provided is a method of identifying a subject for whom prophylactic treatment for a disease or disorder associated with infection caused by *Chlamydia* is indicated, comprising: a) obtaining a biological sample from the subject; and b) assaying the sample of (a) for one or more proteins that are altered due to *Chlamydia* infection in the subject; wherein altered is defined as a decrease or increase in the amount of the protein(s) of (b), and/or as a decrease or increase or change in its posttranslational modification (e.g., phosphorylation, oxidation, etc.) and/or as a decrease or increase in activity of the one more proteins, and wherein detection of an alteration in the protein(s) of (b) relative to a control identifies the subject as a subject for whom prophylactic treatment for a disease or disorder associated with infection caused by *Chlamydia* is indicated. In some embodiments, this method can further comprise: c) providing prophylactic treatment to the subject if the subject is identified in step (b) as a subject for whom prophylactic treatment for a disease or disorder associated with infection caused by *Chlamydia* is indicated; and d) not providing prophylactic treatment to the subject if the subject is not identified in step (b) as a subject for whom prophylactic treatment for a disease or disorder associated with infection caused by *Chlamydia* is indicated.

Additionally provided herein is a method of guiding a treatment regimen for a subject being treated for a disease or disorder associated with infection caused by *Chlamydia*, comprising: a) obtaining a first biological sample from the subject prior to or during treatment; b) assaying the first biological sample for one or more proteins that are altered due to *Chlamydia* infection in the subject, wherein altered is defined as a decrease or increase in the amount of the protein(s) of (b), and/or as a decrease or increase or change in its posttranslational modification (e.g., phosphorylation, oxidation, etc.) and/or as a decrease or increase in activity of the one or more proteins; c) obtaining a second biological sample from the subject at a subsequent time point during treatment and/or after treatment; d) assaying the second biological sample for one or more proteins (e.g., the same one or more proteins assayed in step (b)) that are altered due to *Chlamydia* infection in the subject; and e) comparing the altered protein(s) assayed in (b) with the amount and/or degree of alteration of the same altered protein(s) assayed in (d), wherein a decrease in the amount and/or degree of alteration of the protein(s) as assayed in the second biological sample as compared with the amount and/or degree of alteration of the protein(s) as assayed in the first biological sample indicates that the treatment regimen is imparting a positive or beneficial effect and should be continued and/or increased and an increase in the amount and/or degree of alteration of the protein(s) as assayed in the second biological sample as compared with the amount and/or degree of alteration of the protein(s) as assayed in the first biological sample indicates that the treatment regimen is not imparting a positive or beneficial effect and should be discontinued or reduced.

A nonlimiting example of a treatment regimen for a subject being treated for a disease or disorder associated with infection caused by *Chlamydia* include treatment with antibiotics, including but not limited to Azithromycin, Doxycycline, Erythromycin base, Erythromycin ethylsuccinate, Levofloxacin, and/or Ofloxacin, singly or in any combination.

In the methods described above, the one or more proteins that are altered due to *Chlamydia* infection can be, but are not limited to, EGFR, AKT, STAT3/5, PLCgamma, MKK4, ATR, cyclin B1, GADD45, MDM1, actin, p53, SIRT1-6, alpha-fetoprotein, apolipoprotein A-1, early growth response 1, peroxiredoxin 3, MKI67 antigen identified by monoclonal antibody KI67, YWHAE, RbL1, heat shock protein 70 kDa (HSPA8), mitochondrial superoxide dismutase 2, endothelial nitric oxide synthase 3 and any combination thereof. In a further embodiment, the present invention provides a method of identifying a subject as having an infection caused by *Chlamydia* or as having had an infection caused by *Chlamydia*, comprising: a) obtaining a biological sample from the subject; and b) measuring in the sample of (a) methylation at specific DNA CpG sites that are altered due to *Chlamydia* infection in the subject; wherein altered is defined as a decrease or increase in the amount of methylation of (b) in the sample relative to a control (e.g., a sample from a subject that does not have and/or has not had *Chlamydia* infection), and wherein detection of alteration of methylation at specific DNA CpG sites relative to control identifies the subject as having an infection caused by *Chlamydia* or as having had an infection caused by *Chlamydia*.

The present invention also provides a method of identifying a subject as having an increased likelihood of having or developing a disease or disorder associated with infection caused by *Chlamydia*, comprising: a) obtaining a biological sample from the subject; and b) measuring in the sample of (a) methylation at specific DNA CpG sites that are altered due to *Chlamydia* infection in the subject, wherein altered is defined as a decrease or increase in the amount of methylation of (b) in the sample relative to a control, and wherein detection of alteration of methylation at specific DNA CpG sites relative to control identifies the subject as having an increased likelihood of having or developing a disorder associated with infection caused by *Chlamydia*.

Also provided herein is a method of identifying a subject for whom prophylactic treatment for a disease or disorder associated with infection caused by *Chlamydia* is indicated, comprising: a) obtaining a biological sample from the subject; and b) measuring in the sample of (a) methylation at specific DNA CpG sites that are altered due to *Chlamydia* infection in the subject, wherein altered is defined as a decrease or increase in the amount of methylation of (b) in the sample relative to a control and wherein detection of alteration of methylation at specific DNA CpG sites relative to control identifies the subject as a subject for whom prophylactic treatment for a developing a disorder associated with infection caused by *Chlamydia* is indicated. In some embodiments, this method can further comprise: c) providing prophylactic treatment to the subject if the subject is identified in step (b) as a subject for whom prophylactic treatment for a disease or disorder associated with infection caused by *Chlamydia* is indicated; and d) not providing prophylactic treatment to the subject if the subject is not identified in step (b) as a subject for whom prophylactic treatment for a disease or disorder associated with infection caused by *Chlamydia* is indicated.

In addition, the present invention provides a method of guiding a treatment regimen for a subject being treated for a disease or disorder associated with infection caused by *Chlamydia*, comprising: a) obtaining a first biological sample from the subject prior to or during treatment; b) measuring in the first biological sample the amount of methylation at specific DNA CpG sites that are altered due to *Chlamydia* infection in the subject; c) obtaining a second biological sample from the subject at a subsequent time point during treatment; d) measuring in the second biological sample the amount of methylation at specific DNA CpG sites that are altered due to *Chlamydia* infection in the subject; and e) comparing the amount of altered methylation in (b) with the amount of altered methylation at the same sites measured in (d), wherein a decrease in the amount of altered methylation sites measured in the second biological sample as compared with the amount of altered methylation sites measured in the first biological sample indicates that the treatment regimen is imparting a positive or beneficial effect and should be continued and/or increased and an increase in the amount of altered methylation sites measured in the second biological sample as compared with the amount of altered methylation sites measured in the first biological sample indicates that the treatment regimen is not imparting a positive or beneficial effect and should be discontinued or reduced. Nonlimiting examples of methylation sites include the promoter region of genes such as STEAP3, FOXP1, C2orf76, LMAN1, SMARCC2, GPR133, FAM46A, ALCAM, TXNIP, LRCH3 and SP5, singly or in any combination.

In some embodiments, a method is provided of identifying a subject as having an infection caused by *Chlamydia* or as having had an infection caused by *Chlamydia*, comprising: a) obtaining a biological sample from the subject; and b) measuring in the sample of (a) the amount of one or more proteins that are downregulated due to *Chlamydia* infection in the subject; wherein a decrease in the amount of the protein(s) of (b) in the sample relative to a control amount of the protein(s) identifies the subject as having an infection caused by *Chlamydia* or as having had an infection caused by *Chlamydia*.

In some embodiments, the present invention provides a method of identifying a subject as having an increased likelihood of having or developing a disease or disorder associated with infection caused by *Chlamydia*, comprising: a) obtaining a biological sample from the subject; and b) measuring in the sample of (a) the amount of one or more proteins that are downregulated due to *Chlamydia* infection in the subject, wherein a decrease in the amount of the protein(s) of (b) in the sample relative to a control amount of protein(s) identifies the subject as having an increased likelihood of having or developing a disorder associated with infection caused by *Chlamydia*.

Furthermore, the present invention provides a method of identifying a subject for whom prophylactic treatment for a disease or disorder associated with infection caused by *Chlamydia* is indicated, comprising: a) obtaining a biological sample from the subject; and b) measuring in the sample of (a) the amount of one or more proteins that are downregulated due to *Chlamydia* infection in the subject, wherein a decrease in the amount of the protein(s) of (b) in the sample relative to a control amount of protein(s) identifies the subject as a subject for whom prophylactic treatment for a developing a disorder associated with infection caused by *Chlamydia* is indicated.

In additional embodiments, the present invention provides a method of guiding a treatment regimen for a subject being treated for a disease or disorder associated with infection caused by *Chlamydia*, comprising: a) obtaining a first biological sample from the subject prior to or during treatment; b) measuring in the first biological sample the amount of one or more proteins that are downregulated due to *Chlamydia* infection in the subject; c) obtaining a second biological sample from the subject at a subsequent time point during treatment; d) measuring in the second biological sample the amount of the one or more proteins that are downregulated due to *Chlamydia* infection in the subject; and e) comparing the amount of the protein(s) measured in (b) with the amount of the protein(s) measured in (d), wherein an increase in the amount of the protein(s) measured in (d) relative to the amount of the protein(s) measured in (b) indicates that the treatment regimen should be continued or increased and a further decrease or limited change in the amount of the protein(s) measured in (d) relative to the amount of the protein(s) measured in (b) indicates that the treatment regimen should be discontinued.

In the methods described above regarding a protein that is downregulated due to *Chlamydia* infection, the protein can be, but is not limited to MKK4, ATR, cyclin B1, GADD45, MDM1, alpha-fetoprotein, apolipoprotein A-1, early growth response 1, peroxiredoxin 3, MK167 antigen identified by monoclonal antibody KI67 and any combination thereof.

In yet further embodiments, the present invention provides a method of identifying a subject as having an infection caused by *Chlamydia* or as having had an infection caused by *Chlamydia*, comprising: a) obtaining a biological sample from the subject; and b) measuring in the sample of (a) the amount of one or more proteins that are upregulated due to *Chlamydia* infection in the subject, wherein an increase in the amount of the protein(s) of (b) in the sample relative to a control amount of the protein(s) (e.g., an amount of the protein(s) in a sample from a subject that does not have and/or has not had a *Chlamydia* infection) identifies the subject as having an infection caused by *Chlamydia* or as having had an infection caused by *Chlamydia*.

Further provided herein is a method of identifying a subject as having an increased likelihood of having or developing a disease or disorder associated with infection caused by *Chlamydia*, comprising: a) obtaining a biological sample from the subject; and b) measuring in the sample of (a) the amount of one or more proteins that are upregulated due to *Chlamydia* infection in the subject, wherein an increase in the amount of the protein(s) of (b) in the sample relative to a control amount of protein(s) identifies the subject as having an increased likelihood of having or developing a disorder associated with infection caused by *Chlamydia*.

In addition, the present invention provides a method of identifying a subject for whom prophylactic treatment for a disease or disorder associated with infection caused by *Chlamydia* is indicated, comprising: a) obtaining a biological sample from the subject; and b) measuring in the sample of (a) the amount of one or more proteins that are upregulated due to *Chlamydia* infection in the subject, wherein an increase in the amount of the protein(s) of (b) in the sample relative to a control amount of protein(s) identifies the subject as a subject for whom prophylactic treatment for a developing a disorder associated with infection caused by *Chlamydia* is indicated.

A further embodiment of this invention includes a method of guiding a treatment regimen for a subject being treated for a disease or disorder associated with infection caused by *Chlamydia*, comprising: a) obtaining a first biological sample from the subject prior to or during treatment; b) measuring in the first biological sample the amount of one or more proteins that are upregulated due to *Chlamydia* infection in the subject; c) obtaining a second biological sample from the subject at a subsequent time point during treatment; d) measuring in the second biological sample the amount of the one or more proteins that are upregulated due to *Chlamydia* infection in the subject; and e) comparing the amount of the protein(s) measured in (b) with the amount of the protein(s) measured in (d), wherein a decrease in the amount of the protein(s) measured in (d) relative to the amount of the protein(s) measured in (b) indicates that the treatment regimen is imparting a positive and/or beneficial effect should be continued or increased, and an increase or limited change in the amount of the protein(s) measured in (d) relative to the amount of the protein(s) measured in (b) indicates that the treatment regimen is not imparting a positive or beneficial effect and should be discontinued or decreased.

In the methods described above regarding a protein that is upregulated due to *Chlamydia* infection, the protein can be, but is not limited to, EGFR, AKT2, PLCγ1, STAT5, YWHAE, RbL 1, heat shock protein 70 kDa (HSPA8), mitochondrial superoxide dismutase 2, endothelial nitric oxide synthase 3, and any combination thereof.

In the methods described above, measuring downregulation or upregulation of a protein and/or assaying a sample for a protein that is altered due to *Chlamydia* infection can be carried out by using protocols that measure the amount of the protein itself, protocols that measure the amount of activity of the protein, protocols that measure the characteristics of the protein (e.g., phosphorylation, oxidation state, etc.), protocols that measure the amount of messenger RNA that encodes the protein, protocols that measure expression of DNA that encodes the protein, etc., either singly or in any combination, all of which are protocols that are well known in the art.

A further embodiment of this invention includes a method of reducing the likelihood of infertility due to *Chlamydia* infection in a subject, comprising administering to the subject an effective amount of an inhibitor of epidermal growth factor receptor (EGFR) expression and/or activity.

By "reducing the likelihood of infertility due to *Chlamydia* infection" is meant that a subject of this invention to whom the compositions of this invention are administered is less likely to become infertile as a result of being infected by *Chlamydia* as compared to the likelihood that an untreated subject will become infertile as a result of being infected by *Chlamydia*. That infertility is prevented or its likelihood as a result of *Chlamydia* infection is reduced in a subject can be determined according to protocols well known in the art.

In some embodiments of the methods of this invention, the disease or disorder associated with infection caused by *Chlamydia* can be cancer or a precancerous condition. Nonlimiting examples of a cancer of this invention include B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, adenocarcinoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, uterine cancer, cervical cancer, gastrointestinal cancer, and any other cancer now known or later identified (see, e.g., Rosenberg (1996) *Ann. Rev. Med.* 47:481-491, the entire contents of which are incorporated by reference herein).

In certain embodiments, employing the methods of this invention provides a reduction in the incidence of hydrosalpinx, oviduct dilatation, and/or cellular infiltration associated with chlamydial infection. Thus, the present invention further provides methods of treating and/or preventing hydrosalpinx, oviduct dilatation, and/or cellular infiltration associated with chlamydial infection in a subject, comprising administering to the subject an effective amount of an inhibitor of EGFR expression and/or activity.

Definitions

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "consists essentially of" (and grammatical variants) means that an immunogenic composition of this invention comprises no other material immunogenic agent other than the indicated agents. The term "consists essentially of" does not exclude the presence of other components in the composition such as adjuvants, immunomodulators, and the like.

The term "disease or disorder associated with infection caused by *Chlamydia*" means that infection with *Chlamydia* was completely or partly responsible for the onset of disease or of the disorder. In some cases, the *Chlamydia* might still be present in the infected tissue; in others, the *Chlamydia* has been cleared or has switched to a persistent state after the initiation of disease or the disorder.

The terms "increased risk" and "decreased risk" as used herein define the level of risk that a subject has of developing a disease or disorder associated with infection by *Chlamydia*, as compared to a control subject that does not have the biomarkers of this invention.

A sample of this invention can be any sample containing protein and/or nucleic acid of a subject, as would be well known to one of ordinary skill in the art. Nonlimiting examples of a sample of this invention include a cell, a body fluid, a tissue, biopsy material, a washing, a swabbing, etc., as would be well known in the art.

A "subject" of this invention includes any animal susceptible to infection by a *Chlamydia* species. Such a subject can be a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species and in particular embodiments, is a human. A "subject in need thereof" is a subject known to be, or suspected of being, infected with, or at risk of being infected with, *Chlamydia*. A subject of this invention can also include a subject not previously known or suspected to be infected by *Chlamydia* or in need of treatment for *Chlamydia* infection. For example, a subject of this invention can be administered the compositions of this invention even if it is not known or suspected that the subject is infected with *Chlamydia* (e.g., prophylactically). A subject of this invention is also a subject known or believed to be at risk of infection by *Chlamydia*.

The species of *Chlamydia* encompassed by this invention include *Chlamydia trachomatis*, *Chlamydia muridarum*, *Chlamydia pneumoniae*, *Chlamydia psittaci*, *Chlamydophila abortus*, and/or *Chlamydia caviae* in any combination.

The terms "prevent," "preventing," and "prevention" and like terms are used herein to include imparting any level of prevention or protection which is of some benefit to a subject, such that there is a reduction in the incidence and/or the severity of the disease in a treated subject, regardless of whether the protection or reduction in incidence and/or severity is partial or complete.

The terms "reduce," "reduced," "reducing," and "reduction" (and grammatical variations thereof), as used herein, describe a decrease in a chlamydial infection- or disease-related parameter or symptom that is of some therapeutic value or benefit to the subject.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

"Effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

Pharmaceutical Compositions

Pharmaceutical compositions comprising a composition of this invention and a pharmaceutically acceptable carrier are also provided. The compositions described herein can be formulated for administration in a pharmaceutical carrier in accordance with known techniques. See, e.g., *Remington, The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention.

An effective amount of a composition of this invention, the use of which is in the scope of present invention, will vary from composition to composition, and subject to subject, and will depend upon a variety of well known factors such as the age and condition of the patient and the form of the composition and route of delivery. An effective amount can be determined in accordance with routine pharmacological procedures known to those skilled in the art. For example, a dosage range for administration of a protein (e.g., an antibody) to a subject in accordance with the methods of this invention can be from about 100 mg/day to about 1000 mg/day. Some nonlimiting examples, include Erlotinib, having a dosage range of about 100-150 mg orally once a day; Cetuximab, having a dosage range of about 100-200 mg once a day by intravenous infusion; and Vectibix, having a recommended dose of about 6 mg/kg, administered as an intravenous infusion over 60 minutes. Doses higher than 1000 mg should be administered over 90 minutes.

The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year or as necessary to control the condition. In some embodiments, one, two, three or four doses over the lifetime of a subject can be adequate to achieve the desired therapeutic effect. The amount and frequency of administration of the composition of this invention will vary depending on the particular condition being treated or to be prevented and the desired therapeutic effect.

The compositions of this invention can be administered to a cell of a subject either in vivo or ex vivo. For administration to a cell of the subject in vivo, as well as for administration to the subject, the compositions of this invention can be administered, for example as noted above, orally, parenterally (e.g., intravenously), by intramuscular injection, intradermally (e.g., by gene gun), by intraperitoneal injection, subcutaneous injection, transdermally, extracorporeally, topically or the like. Also, the composition of this invention may be pulsed onto dendritic cells, which are isolated or grown from patient cells, according to methods well known in the art, or onto bulk PBMC or various cell subtractions thereof from a patient.

If ex vivo methods are employed, cells or tissues can be removed and maintained outside the body according to standard protocols well known in the art while the compositions of this invention are introduced into the cells or tissues. For example, the nucleic acids and vectors of this invention can be introduced into cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject. Thus, in one embodiment of this invention, the chimeric polypeptide comprising the recall antigen and new antigen of this invention can be presented to the immune system in a subject on the surface of a cell (i.e., as a cell surface antigen present in the plasma membrane of the cell) and in other embodiments can be presented to the immune system in a subject as a non-cell associated (i.e., cell-free) chimeric polypeptide.

Administration of the nucleic acids of this invention can be achieved by any one of numerous, well-known approaches, for example, but not limited to, direct transfer of the nucleic acids, in a plasmid or viral vector, or via transfer in cells or in combination with carriers such as cationic liposomes. Such methods are well known in the art and readily adaptable for use in the methods described herein. Furthermore, these methods can be used to target certain diseases and cell populations by using the targeting characteristics of the carrier, which would be well known to the skilled artisan.

Transfer vectors employed in the methods of this invention can be any nucleotide construct used to deliver nucleic acid into cells, e.g., a plasmid or viral vector, such as a retroviral vector which can package a recombinant retroviral genome (see e.g., Pastan et al., *Proc. Natl. Acad. Sci. U.S.A.* 85:4486 (1988); Miller et al., *Mol. Cell. Biol.* 6:2895 (1986)). The recombinant retrovirus can then be used to infect and thereby deliver a nucleic acid of the invention to the infected cells. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naldini et al., *Science* 272:263-267, 1996), pseudotyped retroviral vectors (Agrawal et al., *Exper. Hematol.* 24:738-747, 1996), and any other vector system now known or later identified. Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used nucleic acid transfer methods. Appropriate means for transfection, including viral vectors, chemical transfectants, or physico-mechanical methods such as electroporation and direct diffusion of DNA, are described by, for example, Wolff et al., *Science* 247:1465-1468, (1990); and Wolff., *Nature* 352:815-818, (1991).

It is further contemplated that the present invention provides a kit comprising the compositions of this invention. It would be well understood by one of ordinary skill in the art that the kit of this invention can comprise one or more containers and/or receptacles to hold the reagents (e.g., drugs, antibodies, small molecules, nucleic acid, etc.) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

The efficacy of treating or preventing *Chlamydia* infection by the methods of the present invention can be determined by detecting a clinical improvement as indicated by the absence of symptoms or other clinical indicators of infection and/or by a change in the subject's symptoms and/or clinical parameters, as would be well known to one of skill in the art.

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Activation of Epidermal Growth Factor (EGFR) is Required for *Chlamydia trachomatis* Development

*Chlamydia trachomatis* (*C. trachomatis*) is a clinically significant human pathogen and one of the leading causative agents of sexually transmitted diseases. As obligate intracellular bacteria, *C. trachomatis* has evolved strategies to redirect the host's signaling and resources for its own survival and propagation. Despite the clinical notoriety of *Chlamydia* infections, the molecular interactions between *C. trachomatis* and its host cell proteins remain elusive. In this study, we focused on the involvement of the host cell epidermal growth factor receptor (EGFR) in *C. trachomatis* attachment and development. A combination of molecular approaches, pharmacological agents and cell lines were used to demonstrate distinct functional requirements of EGFR in *C. trachomatis* infection. We show that *C. trachomatis* increases the phosphorylation of EGFR and of its downstream effectors PLCγ1, Akt and STAT5. While both EGFR and platelet-derived growth factor receptor-β (PDGFRβ) are partially involved in bacterial attachment to the host cell surface, it is only the knockdown of EGFR and not PDGFRβ that affects the formation of *C. trachomatis* inclusions in the host cells. Inhibition of EGFR results in small immature inclusions, and prevents *C. trachomatis*-induced intracellular calcium mobilization and the assembly of the characteristic F-actin ring at the inclusion periphery. By using complementary approaches, we demonstrate that the coordinated regulation of both calcium mobilization and F-actin assembly by EGFR are necessary for maturation of chlamydial inclusion within the host cells. A particularly important finding of this study is the co-localization of EGFR with the F-actin at the periphery of *C. trachomatis* inclusion where it may function to nucleate the assembly of signaling protein complexes for cytoskeletal remodeling required for *C. trachomatis* development. Cumulatively, the data reported here connect the function of EGFR to *C. trachomatis* attachment and development in the host cells, leading to new venues for targeting *C. trachomatis* infections and associated diseases.

*C. trachomatis* is one of the leading causative agents of sexually transmitted diseases. As an intracellular pathogen it has evolved strategies to redirect hosts' signaling and resources for its own survival and propagation. The recruitment of tyrosine phosphorylated proteins at the site of entry in the host cell and the requirement of actin polymerization along the time course of infection are well documented. However, a function of receptor tyrosine kinases beyond the stages of attachment and entry in the host cell has never been reported. The studies presented here show that expression and phosphorylation of host cell epidermal growth factor receptor (EGFR) is required for *C. trachomatis* development. Most importantly, *C. trachomatis* can regulate the phosphorylation and intracellular localization of EGFR. Co-localization of EGFR with the F-actin at the periphery of *C. trachomatis* inclusion in the host cells is a particularly exciting and novel finding implicating EGFR in the regulation of actin polymerization around *C. trachomatis* inclusions. These studies open the opportunity to investigate key structural and functional elements in EGFR that are necessary for *C. trachomatis* development, leading to new therapies to advance the treatment of *C. trachomatis* infections and associated diseases.

*Chlamydia trachomatis* (*C. trachomatis*) is among the most common sexually transmitted pathogens in the US and contributes to many conditions, such as pelvic inflammatory disease, infertility, and others. *C. trachomatis* has a small genome, ~1.0 Mb, and like viruses (e.g., HPV), depends on the host cell for survival. The chlamydial life cycle exhibits two forms that are relevant to chlamydial pathology. The elementary body (EB) is a 'spore-like' infectious form, previously perceived as metabolically inert but recently shown to display maintenance level of metabolic activity. Following internalization into the host cells, EBs initiate the inclusion formation and transform into metabolically active reticulate bodies (RBs), which then replicate within the inclusion. During the time course of RB replication, the early inclusions expand and fuse to form the early-mid inclusion, which then further expands into the mid-late inclusion. At this stage the RBs are converted back into EBs and are then released from the host cells through extrusion or cell lysis. The process of *C. trachomatis* development from attachment/entry to extrusion/exit, is regulated by an arsenal of *C. trachomatis* and host cell proteins. For example, several groups reported the recruitment of tyrosine-phosphorylated host cell proteins at the site of *C. trachomatis* entry into the host cell and the requirement of actin polymerization along the time course of infection. In accordance with this, previous studies have shown that *Chlamydia muridarum* (*C. muridarum*), a species closely related to *C. trachomatis*, induces activation of two host cell surface receptor tyrosine kinases: the fibroblast growth factor receptor (FGFR), and the platelet derived growth factor receptor β (PDGFRβ). FGFR and PDGFRβ have been proposed to be important for binding of the chlamydial EBs to the host cell. PDGFRβ is phosphorylated upon *C. muridarum* infection and can function as a receptor for bacterial binding to the host cell. A function for PDGFR activation beyond this stage was not reported. *C. muridarum* also recruits FGF2 signaling to enhance infection and bacterial spread. In this case, FGF2 acts as a bridging molecule between the EBs and the receptor that results in the activation of FGFR and bacterial uptake in the host cells.

In the present study, evidence is provided that identifies EGFR signaling as the first host cell receptor pathway required for *C. trachomatis* development within the host cell. Our data show: a) distinct functional requirements of EGFR versus PDGFR during *C. trachomatis* infection—we demonstrate that PDGFR is critical only at the step of bacterial attachment, and that knockdown of EGFR but not PDGFR impairs development of *C. trachomatis* inclusions within the host cell; b) infection with *C. trachomatis* increases phosphorylation of EGFR and of its downstream effectors PLCγ1, Akt and STAT5; c) *C. trachomatis* infection results in re-localization of EGFR at the periphery of *C. trachomatis* inclusion inside the host cell; and d) inhibition of EGFR results in the formation of a diffuse assembly of F-actin at the periphery of incompletely developed inclusions. Co-localization of EGFR with the F-actin at the periphery of *C. trachomatis* inclusion is a particularly exciting and novel finding implicating EGFR in the regulation of actin polymerization around *C. trachomatis* inclusions.

Figure 4:
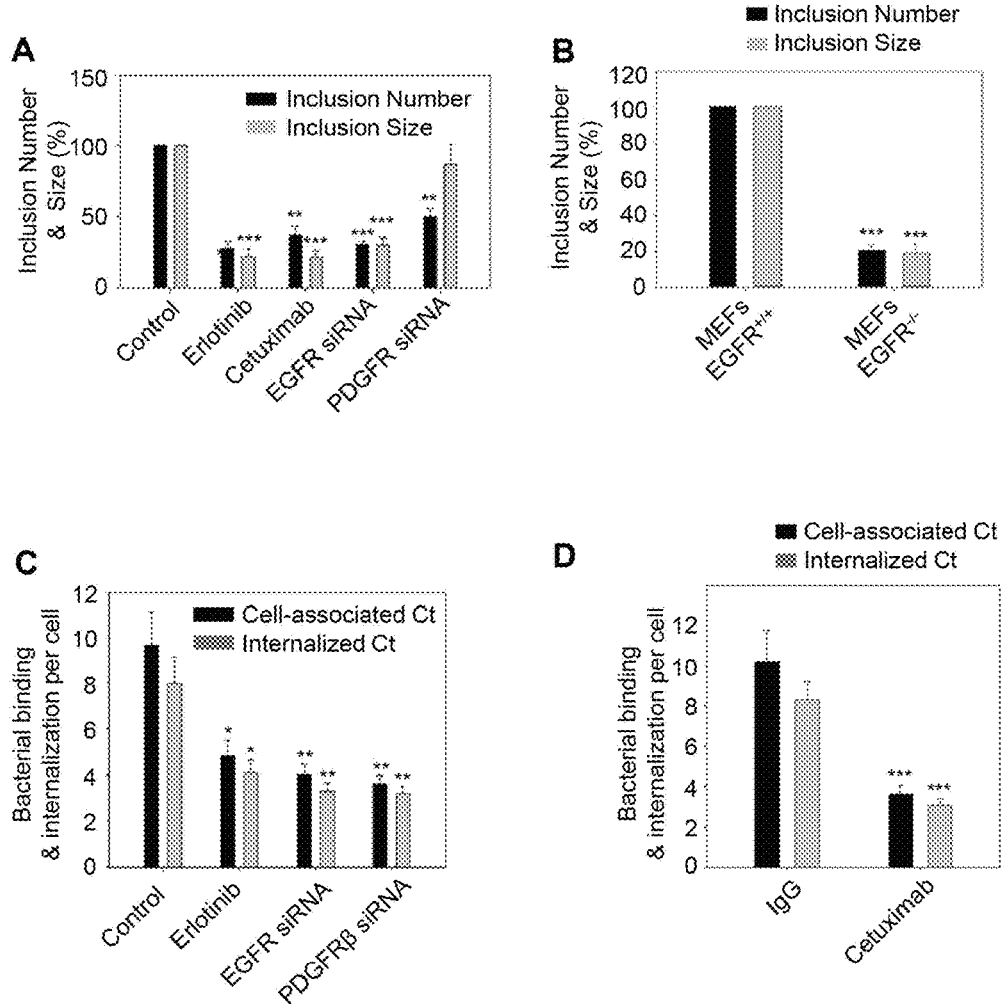
FIG. 4. EGFR is important for bacterial attachment and inclusion development. (Panels A-B) Effect of EGFR inhibition on number and size of inclusions. (Panel A) HeLa cells treated with Erlotinib (a small molecule inhibitor that targets the intracellular kinase domain of EGFR), Cetuximab, EGFR siRNA or PDGFRβ siRNA were infected with *C. trachomatis* for 24 h, fixed, and analyzed by confocal microscopy and ImageJ software. Data from three independent experiments are expressed as percentage of total number of inclusions (black bar) or inclusion size (gray bar) in comparison to the control. In each case the data were normalized with the respective controls (DMSO, IgG or control siRNA treated cells). The number of inclusions was significantly reduced in both EGFR-inhibited (Erlotinib, Cetuximab or EGFR siRNA treated cells) as well as PDGFRβ depleted cells (P<0.01). Significant reduction in the inclusion size was observed only in the Erlotinib, Cetuximab and EGFR siRNA treated cells (P<0.001) but not in PDGFRβ-depleted cells. (Panel B) MEFs EFGR$^{+/+}$ and MEFs EGFR$^{+/+}$ were infected and processed as in (Panel A). Significant reduction in both inclusion number and size was observed in MEFs EGFR$^{-/-}$ (P<0.001) in comparison to the MEFs EGFR$^{+/+}$ cells. Data are from three independent experiments. (Panels C-D) Effect of EGFR inhibition on chlamydial attachment and entry into the host cell. HeLa cells treated with Erlotinib, EGFR siRNA and PDGFRβ siRNA (Panel C) or Cetuximab (Panel D), were infected with *C. trachomatis* for 2.5 h and inside out staining was performed to differentially stain both external and internalized *C. trachomatis*. Data from three independent experiments are expressed as number of cell-associated bacteria (external+internalized *C. trachomatis*) and internalized *C. trachomatis* per infected host cell. Significant reduction in the chlamydial binding to the host cell surface was observed upon inhibition of both EGFR and PDGFRβ (P<0.05) in comparison to the *C. trachomatis*-infected control cells. (Panels E-F) Levels of chlamydial Hsp60 antigen. HeLa cells treated with Erlotinib, Cetuximab, EGFR siRNA or PDGFRβ siRNA were infected with *C. trachomatis* for 2.5 h and Western blotting was performed with anti-chlamydial Hsp60 antibody. Quantification of the Western blots from three independent experiments showed a significant (P<0.001) reduction in Hsp60 levels (Panel F). β-actin was used as loading control. In each case the data were normalized with the respective controls (DMSO, IgG or control siRNA treated cells). (Panels G-H) Transmission electron micrographs of HeLa cells infected with *C. trachomatis*. HeLa cells treated with Erlotinib (Panel G) and Cetuximab (Panel H), with respective controls, were infected with *C. trachomatis* for 24 h and fixed for transmission electron microscopy. Note the typical large inclusions in the control chlamydial infected cells. In cells treated with Erlotinib and Cetuximab the inclusions are smaller and less mature. Scale Bar=2 mm.
Figure 4:
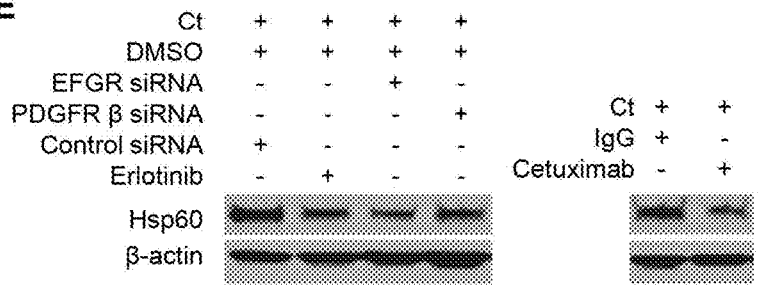
Figure 4:
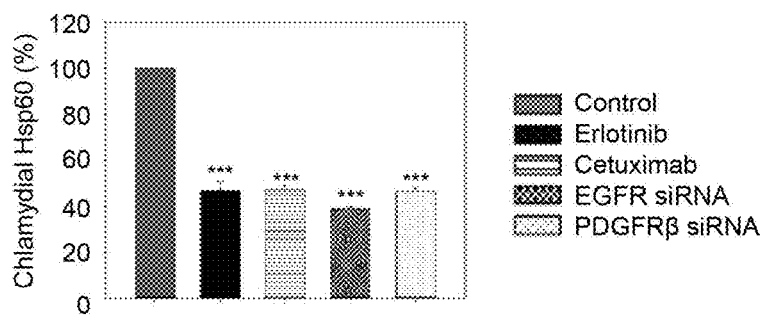
Figure 4:
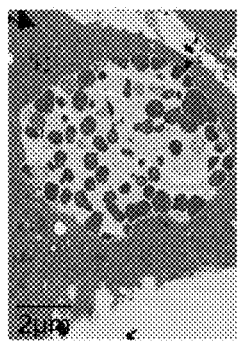
Figure 4:
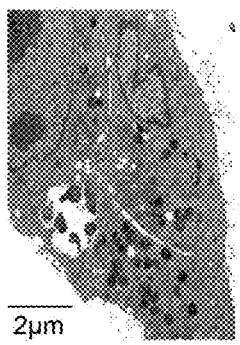
Figure 4:
Figure 4:
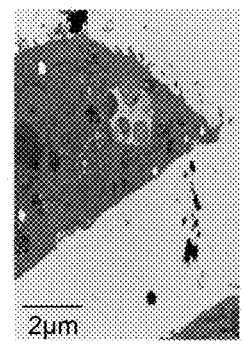

*C. trachomatis* induces EGFR phosphorylation and activation of EGFR signaling pathways. To assess the role of EGFR in *C. trachomatis* development, we initiated our studies by comparing the chlamydial inclusion formation between isogenic cell lines, MEFs EFGR$^{+/+}$ (mouse embryonic fibroblasts) and EGFR null MEFs (MEFs EGFR$^{-/-}$). Both cell lines were infected with chlamydial EBs and at 24 hours post infection (hpi) the cells were stained with chlamydial FITC-conjugated anti-lipopolysaccharide (LPS) mAb as described herein. Confocal imaging was performed to visualize the development of chlamydial inclusions. Well-developed *C. trachomatis* inclusions were observed in MEFs EGFR$^{+/+}$ while in the MEFs EGFR$^{-/-}$ cells, the inclusions were significantly smaller in size in comparison to MEFs EGFR$^{+/+}$ (FIG. 1, Panel A, quantification is shown in FIG. 4, Panel B). These initial results indicated a role of EGFR in *C. trachomatis* infection and prompted us to explore it further. We first examined whether *C. trachomatis* could induce EGFR phosphorylation in infected cells. To ensure the results were not biased by the selection of cell line, both HeLa cells and MEFs EGFR$^{+/+}$ were used in these experiments. The MEFs EGFR$^{+/+}$ cells were infected with chlamydial EBs and lysed at different time points ranging from 0.5 hpi to 5 hpi. We observed a significant 1.8-fold increase in phosphorylation of Y1173 in EGFR that peaked at 2.5 hpi (P<0.05) (FIG. 1, Panels B-C). Similar results were obtained in HeLa cells (FIG. 1, Panels D-E), in which we also observed an increase in PDGFRβ phosphorylation (FIG. 1, Panel F). We further analyzed the phosphorylation of EGFR at other tyrosine residues (Y845, Y992, Y1045 and Y1148). An increased phosphorylation was observed in *C. trachomatis*-infected MEFs EGFR$^{+/+}$ (2.5 and 5 hpi) at all sites analyzed with the exception of Y1148 (FIG. 1, Panel G). The results show that *C. trachomatis* can enhance EGFR activity and indicates a function of EGFR signaling in *C. trachomatis* infection.

Figure 2:
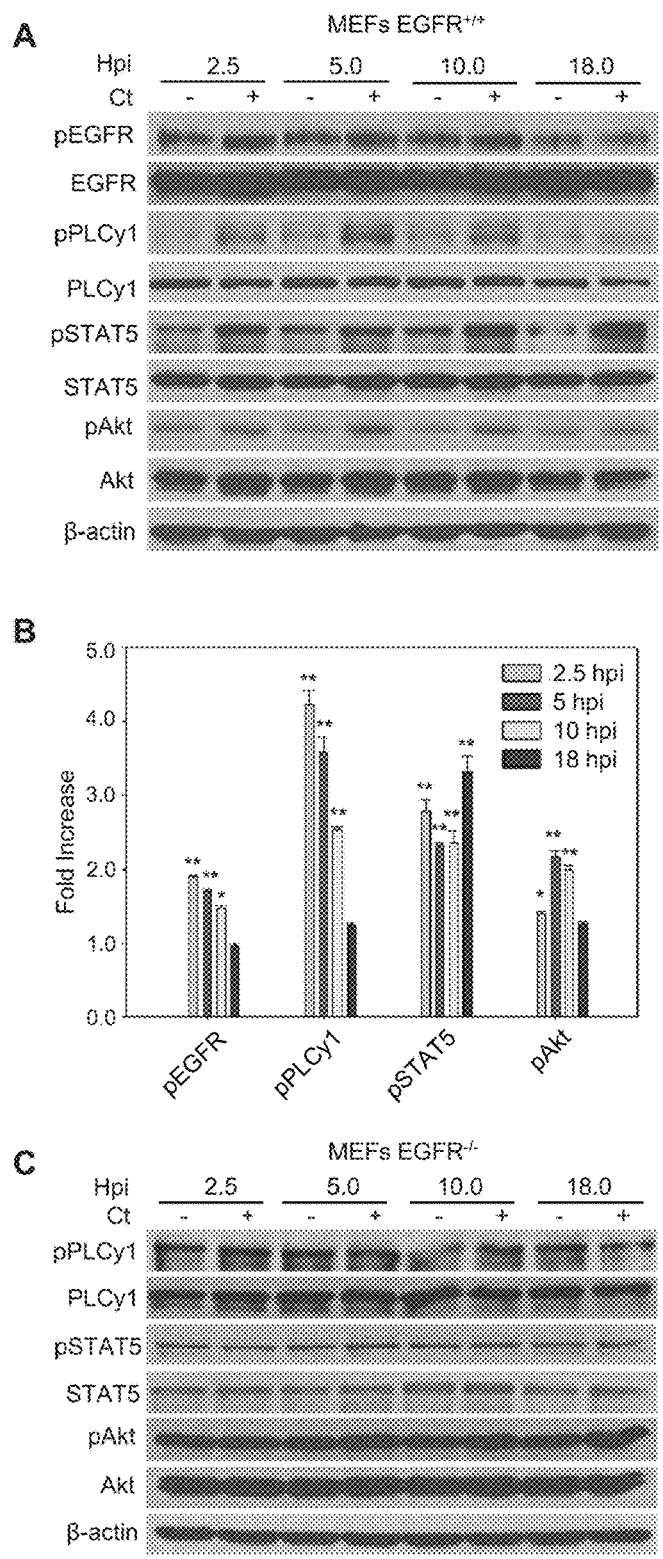
Figure 3:
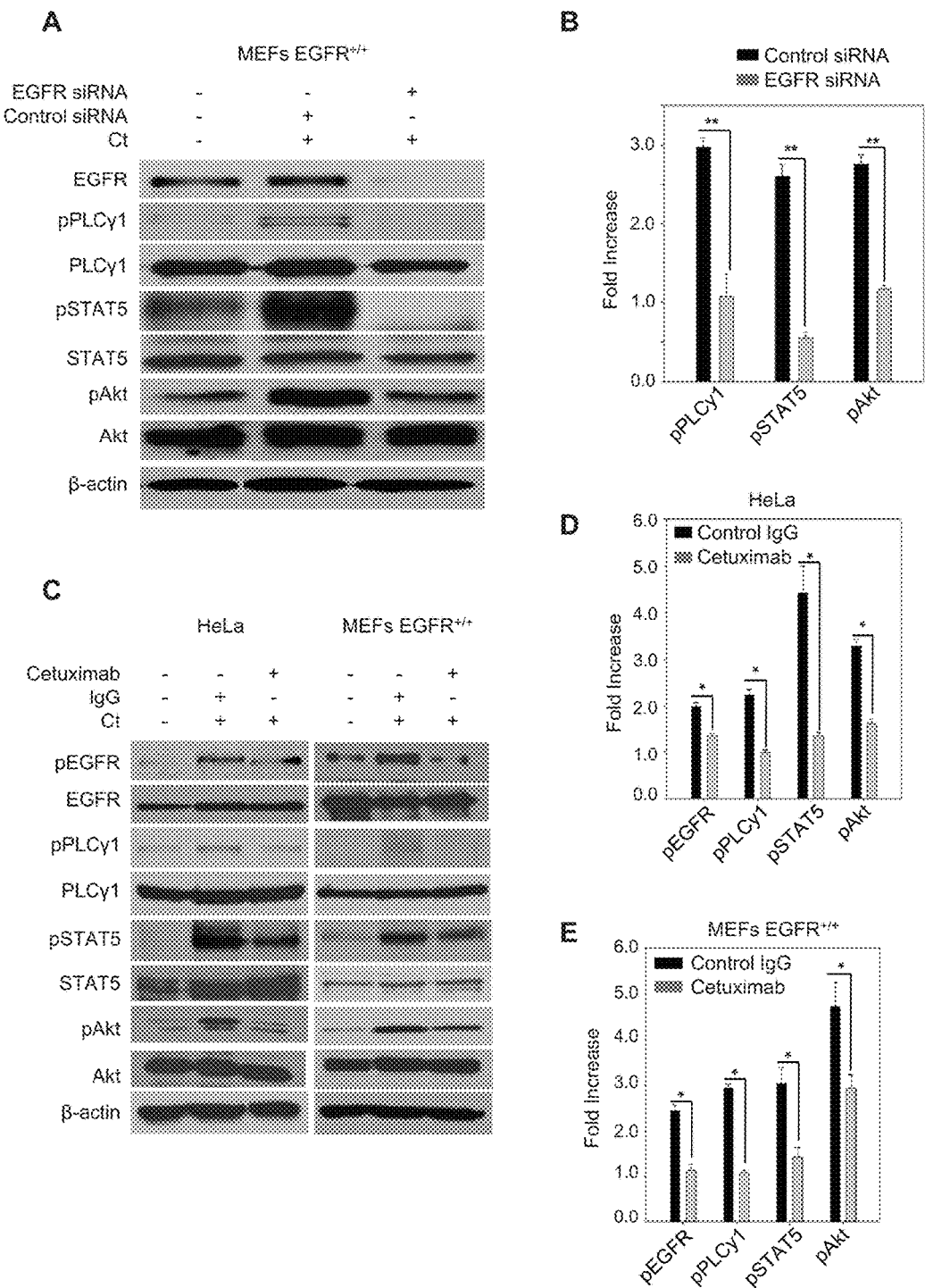
FIG. 3. *C. trachomatis*-induced activation of PLCγ1, STAT5 and Akt is EGFR-dependent. (Panels A-B) MEFs EGFR$^{+/+}$ were treated with either scrambled (control) or EGFR siRNA and then infected with *C. trachomatis*. Cells were lysed after 2.5 hpi and immunoblotted with antibodies against phosphorylated and total PLCγ1, STAT5 and Akt (Panel A). Western blots from three independent experiments were quantified (Panel B). (Panels C-E) HeLa and MEFs EGFR$^{+/+}$ were treated with Cetuximab (an anti-EGFR antibody that blocks the binding of EGF to EGFR, thus blocking receptor activation) followed by *C. trachomatis* infection. At 2.5 hpi the lysates were immunoblotted with antibodies against phosphorylated and total EGFR, PLCγ1, STAT5 and Akt (Panel C). Western blots from three independent experiments were quantified for both HeLa (Panel D) and MEFs (Panel E). *C. trachomatis*-induced phosphorylation of PLCγ1, STAT5 and Akt was completely or partially abrogated in cells that were either depleted of EGFR (Panels A-B; P<0.01) or treated with Cetuximab (Panels C-E; P<0.05). β-actin was used as loading control.

EGFR activation in response to extracellular cues (e.g., EGF ligand) is known to activate PI3K/Akt, PLCγ1 (phospholipase Cγ1) and STAT proteins (signal transducers and activators of transcription). To determine whether *C. trachomatis*-induced EGFR phosphorylation can also activate its downstream effector proteins, the phosphorylation of PLCγ1 (Y783), Akt (S473) and STAT5 (Y694) was monitored in MEFs EGFR$^{+/+}$ and EGFR$^{-/-}$ cells infected with chlamydial EBs at time points ranging from 2.5 hpi to 18 hpi. As shown in FIG. 2, Panel A and the quantification in FIG. 2, Panel B, *C. trachomatis* infection induced a significant increase in phosphorylation of EGFR and its downstream targets, PLCγ1, Akt and STAT5 at 2.5, 5 and 10 hpi (P<0.05). At 18 hpi, the phosphorylation of EGFR, Akt and PLCγ1 returned close to the basal level. The phosphorylation of STAT5 persisted at 18 hpi, presumably due to delayed kinetics or secondary activation subsequent to primary stimulus. The EGFR dependence of these phosphorylation events was further confirmed by the experiments in MEFs EGFR$^{-/-}$ cells. Under these conditions, *C. trachomatis* infection at the same time points did not induce an increase in phosphorylation of PLCγ1, Akt and STAT5 proteins (FIG. 2, Panel C). Combined with our previous observation of phenotypically smaller inclusions formed in MEFs EGFR$^{-/-}$ cells (FIG. 1, Panel A), these findings led us to hypothesize that activation of an EGFR-dependent signaling axis was essential for establishing a successful *C. trachomatis* infection. To further confirm that the activation of these proteins was *C. trachomatis*- and EGFR-dependent, we investigated the *C. trachomatis*-induced activation of PLCγ1, STAT5 and Akt in MEF EFGR$^{+/+}$ and HeLa cells using multiple methods of EGFR inhibition. MEFs EGFR$^{+/+}$ cells were treated with EGFR siRNA for 48 h, then infected with *C. trachomatis* for 2.5 h and tested for activation of PLCγ1, STAT5 and Akt. Chlamydial infection resulted in increased phosphorylation of all three proteins in cells treated with control siRNA but not in cells treated with EGFR siRNA (FIG. 3, Panels A-B; P<0.01). *C. trachomatis*-induced phosphorylation of EGFR, PLCγ1, STAT5 and Akt was also inhibited by treatment of HeLa and MEFs EGFR$^{+/+}$ with Cetuximab, a monoclonal antibody that binds to the extracellular domain of EGFR and specifically blocks EGFR functions (FIG. 3, Panels C-E). These studies confirmed EGFR activation as one of the upstream regulatory events in the phosphorylation of PLCγ1, STAT5 and Akt signaling in *C. trachomatis*-infected cells.

Figure 10:
FIG. 10. Western blot analysis of EGFR phosphorylation with Erlotinib treatment. HeLa cells were treated with Erlotinib (15 µM, 25 µM) followed by Western blotting. Phosphorylation of EGFR was significantly reduced in comparison to the untreated cells. β-actin was used as loading control.
Figure 11:
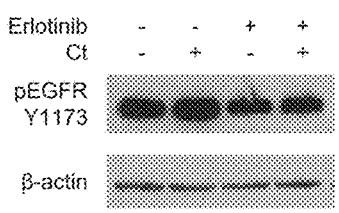
FIG. 11. Western blot analysis of EGFR phosphorylation induced by Ct infection in the absence or presence of Erlotinib treatment. HeLa cells were treated with 25 µM Erlotinib for 2 h followed by the Ct infection for 2.5 h. Western blotting with pEGFR antibody showed an increase in EGFR phosphorylation upon Ct infection in the absence of Erlotinib but not in the presence of the drug. β-actin was used as loading control.
Figure 12:
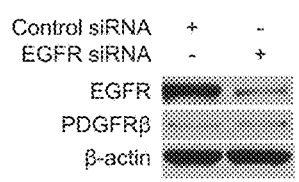
FIG. 12. Western blot analysis of EGFR expression. HeLa cells were treated with EGFR siRNA followed by Western blotting. siRNA treatment significantly reduced the protein levels of EGFR by 70% in comparison to the control siRNA treated cells. β-actin was used as loading control. This study also confirmed that expression of PDGFRβ remained unaffected in EGFR siRNA treated cells.
Figure 13:
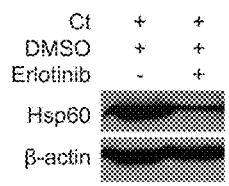
FIG. 13. Western blot analysis of chlamydial Hsp60. HeLa cells were treated with Erlotinib (25 µM) followed by Ct infection for 24 h. Western blotting with anti-chlamydial Hsp60 antibody showed marked decrease in the Hsp60 antigen in the Erlotinib treated cells. β-actin was used as loading control.
Figure 14:
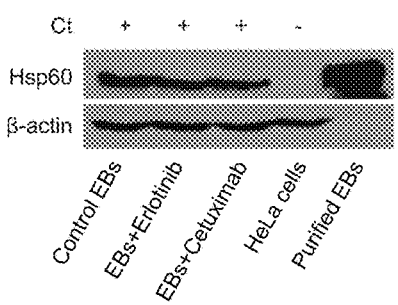
FIG. 14. Western blot analysis to test the viability of elementary bodies (EBs) treated with Erlotinib and Cetuximab. HeLa cells were pretreated with Erlotinib (25 µM) or Cetuximab (20 µg/ml) for 2.5 h followed by Ct infection for 24 h. Western blotting with anti-chlamydial Hsp60 antibody showed no difference in the chlamydial Hsp60 antigen load between the cells infected with either drug-treated or untreated EBs. β-actin was used as loading control.
Figure 15:
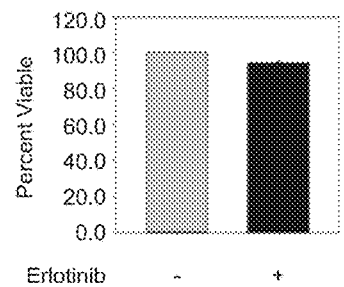
FIG. 15. Cell viability assay. HeLa cells were treated with 25 µM of Erlotinib for 24 h followed by the MTT assay (Roche). Erlotinib treatment did not affect the viability of HeLa cells.

EGFR is essential for the formation of mature chlamydial inclusions. Next, we assessed the contribution of EGFR to the formation of *C. trachomatis* inclusions in HeLa cells and MEFs. EGFR was inhibited by using Erlotinib, Cetuximab or EGFR siRNA. Erlotinib is a small molecule inhibitor that targets the intracellular kinase domain of EGFR, while Cetuximab blocks the binding of EGF to its cognate receptor and thus blocks receptor activation. Effective inhibition of EGFR phosphorylation by Erlotinib or Cetuximab was confirmed by Western blot (FIGS. 10, 11 and 3, Panel C). Similarly, Western blot analysis was performed to confirm the depletion of EGFR protein in HeLa and MEFs treated with EGFR siRNA (FIGS. 12 and 3, Panel A). HeLa cells with or without EGFR inhibition (protein depletion or inhibition of function), were infected with *C. trachomatis*. The cells were immunostained using anti-chlamydial LPS mAb at 24 hpi and analyzed by confocal imaging to quantify the size and number of inclusions. In comparison to control (DMSO, IgG or control siRNA treated cells), there was a significant decrease in both the number and size of chlamydial inclusions under all treatment conditions (P<0.01 to P<0.001; FIG. 4, Panel A). Use of multiple approaches to inhibit EGFR discounts the possibility of observing these results because of an unspecific interaction of the inhibitors with non-target molecules, a potential caveat of using pharmacological agents. The decreased chlamydial infection upon EGFR inhibition was further confirmed by monitoring the chlamydial Hsp60 using Western blot analysis (FIG. 13). To ensure that Erlotinib and Cetuximab treatments did not affect the viability of chlamydial EBs, we infected HeLa cells with EBs that were pretreated with Erlotinib or Cetuximab. At 24 hpi the cells were lysed and blotted using antibodies against chlamydial Hsp60. The Hsp60 antigen load in the cells infected with drug-treated EBs was comparable to the infection by the untreated EBs (FIG. 14), confirming that EGFR inhibitors did not affect the viability of EBs in these experiments. Additional studies were performed to ensure that the poor inclusion development was not due to loss of the host cells' viability during Erlotinib treatment. The highest concentration (25 μM) and maximum duration (24 h) of Erlotinib treatment did not reduce the viability of HeLa cells (FIG. 15).

Figure 16:
FIG. 16. Western blot analysis of PDGFRβ expression. HeLa cells were treated with PDGFRβ siRNA followed by Western blotting. siRNA treatment significantly reduced the protein levels of PDGFRβ in comparison to the control siRNA treated cells. β-actin was used as loading control. It was also confirmed that expression of EGFR remained unaffected in PDGFRβ siRNA treated cells.
Figure 17:
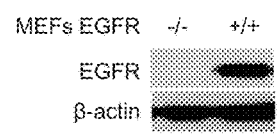
FIG. 17. Western blot analysis of EGFR in MEFs EGFR$^{+/+}$ and MEFs EGFR$^{-/-}$. EGFR was expressed only in MEFs EGFR$^{+/+}$. β-actin was used as loading control.
Figure 22:
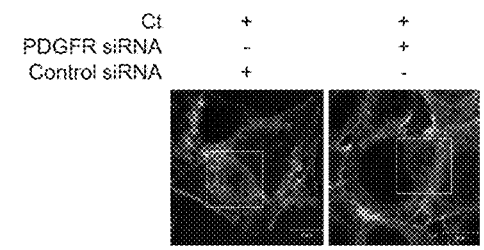
FIG. 22. Inclusion development in PDGFR siRNA treated cells. HeLa cells treated with control siRNA or PDGFR siRNA were infected with *C. trachomatis* for 24 h, fixed, and processed for confocal microscopy. F-actin was detected with Alexa Fluor 488-phalloidin and chlamydial inclusions were detected using anti-chlamydial LPS antibody. Note that silencing PDGFR did not affect the size of the inclusion.
Figure 23:
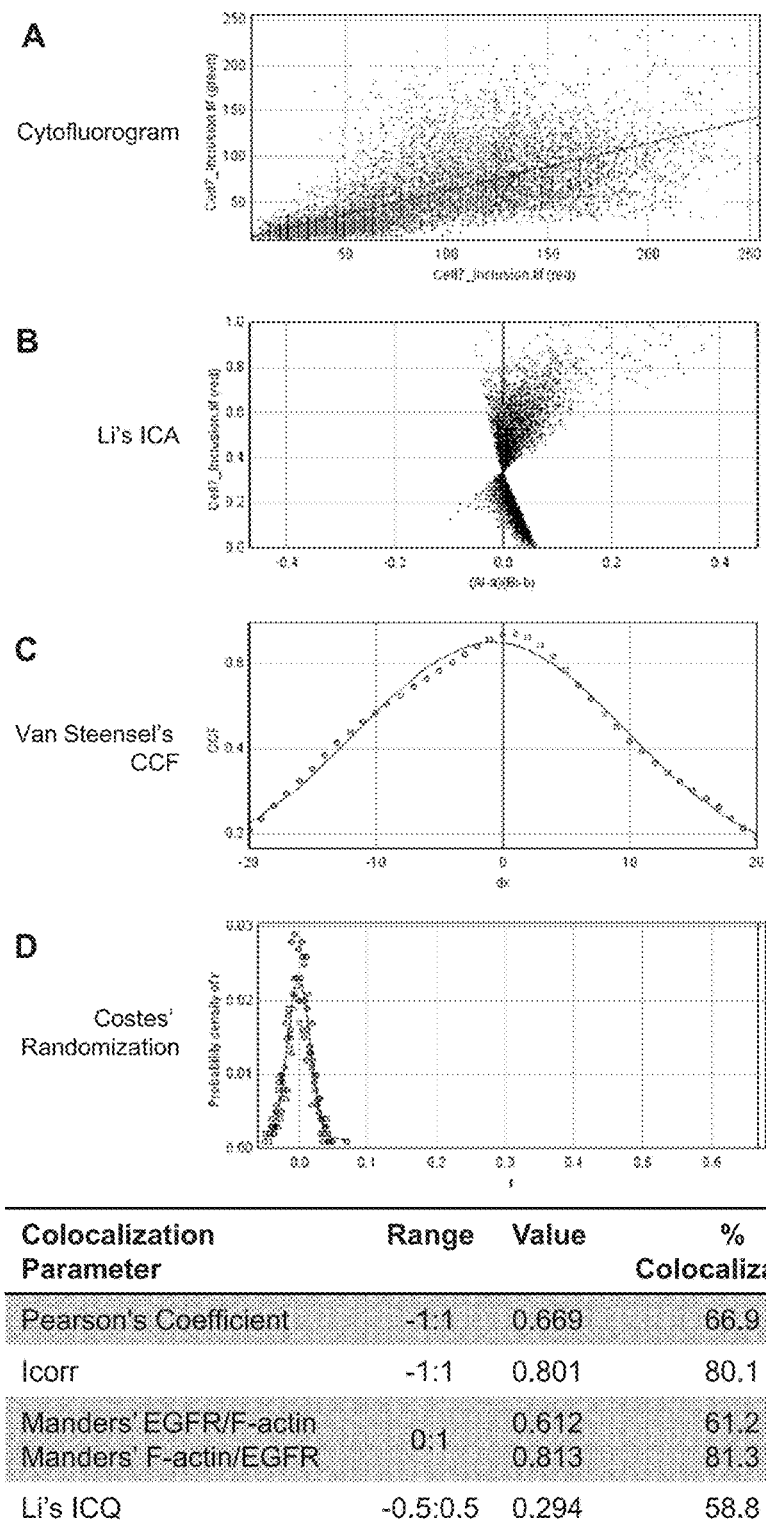
FIGS. 23, 24, 25, 26, 27, 28 and 29. Comparison of cytofluorogram, Li's ICA, Van Steensel's CCF, and Costes' randomization analyses for EGFR and F-actin channels of representative inclusion and non-inclusion area images and additional algorithms used to generate data in FIG. 8, Panel D. Cytofluorograms are generated to demonstrate the relationship between intensities of each color channel (EGFR—red; F-actin—green) at each pixel—a positive slope greater than 0.5 and a tight scatter of data points indicates co-localization of EGFR with F-actin. The increased slope of the inclusion cytofluorogram indicates higher colocalization of EGFR and F-actin than the non-inclusion image. This information was then utilized to determine the Pearson's Coefficient. Li's Intensity Correlation Analysis (ICA) is performed to gain further insight into the degree of co-localization. It calculates the difference from the mean channel intensity of each color at each pixel. Li's ICA analysis indicates noise-corrupted co-localization of EGFR and F-actin in the inclusion area images as indicated by the points mostly falling on the positive side of the x-axis. The non-inclusion area image is found to have almost no correlation between EGFR and F-actin as indicated by the points falling roughly equally along the positive and negative sides of the x-axis. Li's ICA was also used here to determine Li's intensity correlation quotient (ICQ). Van Steensel's CCA is performed by shifting one color channel in the x-direction pixel per pixel relative to the other channel and calculating the respective Pearson's Coefficient. The resulting Pearson's Coefficients are then plotted as a function of the pixel shift. Bell-shaped data in Van Steensel's CCA indicates co-localization and trough-shaped data indicates exclusion. Van Steensel's CCF analysis shows co-localization of EGFR and F-actin with unequal signal brightness in the inclusion area images and very weak, noise-corrupted partial overlap in the non-inclusion area images. Costes' randomization algorithm is performed to rule out the possibility that the observed co-localization of EGFR and F-actin is attributable simply to random noise. Costes' randomization algorithm generates a number of images populated by various amounts of noise in each color channel and calculates the Pearson's coefficient for each one (represented by the data points along the line). Costes' randomization algorithm shows that the Pearson's coefficients of both the inclusion area images and the non-inclusion area image are due to signal rather than noise. Additional algorithm used in FIGS. 8 and 24-29: The normalized mean deviation product (nMDP) is calculated for each pixel in the image to identify regions of intense co-localization or exclusion within the image. The nMDP analysis operates on the same basic principles as Li's ICA, except that pixel position information is maintained, allowing the user to visualize where in the image the algorithm has identified co-localization or exclusion. This algorithm is also used here to determine the index of correlation (Icon). Manders' coefficients are calculated to provide further insight into the relationship between EGFR and F-actin within each image. The EGFR/F-actin Manders' coefficient is a measure of the percentage of EGFR signal that is co-localized with F-actin signal. Conversely, the F-actin/EGFR Manders' coefficient is a measure of the percentage of F-actin signal that is co-localized with EGFR signal.
Figure 24:
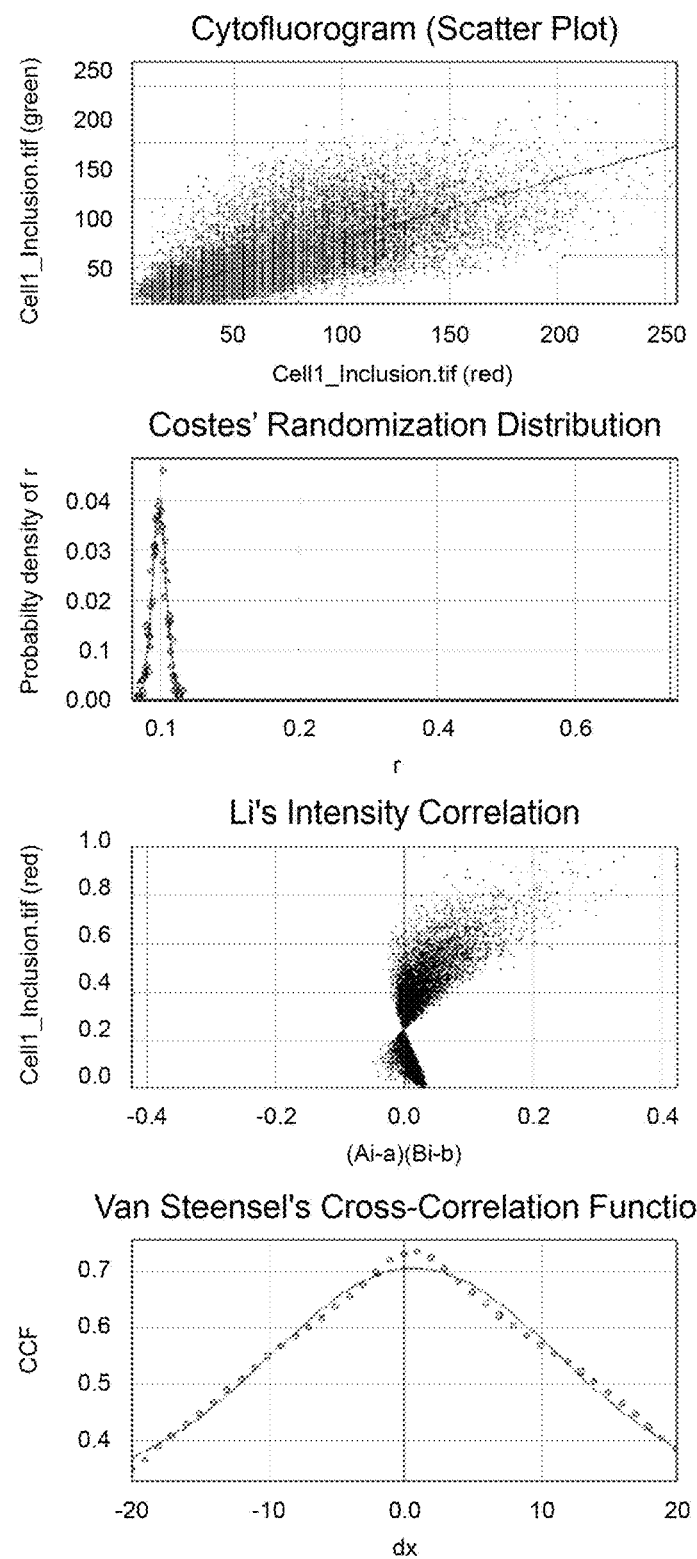
Figure 25:
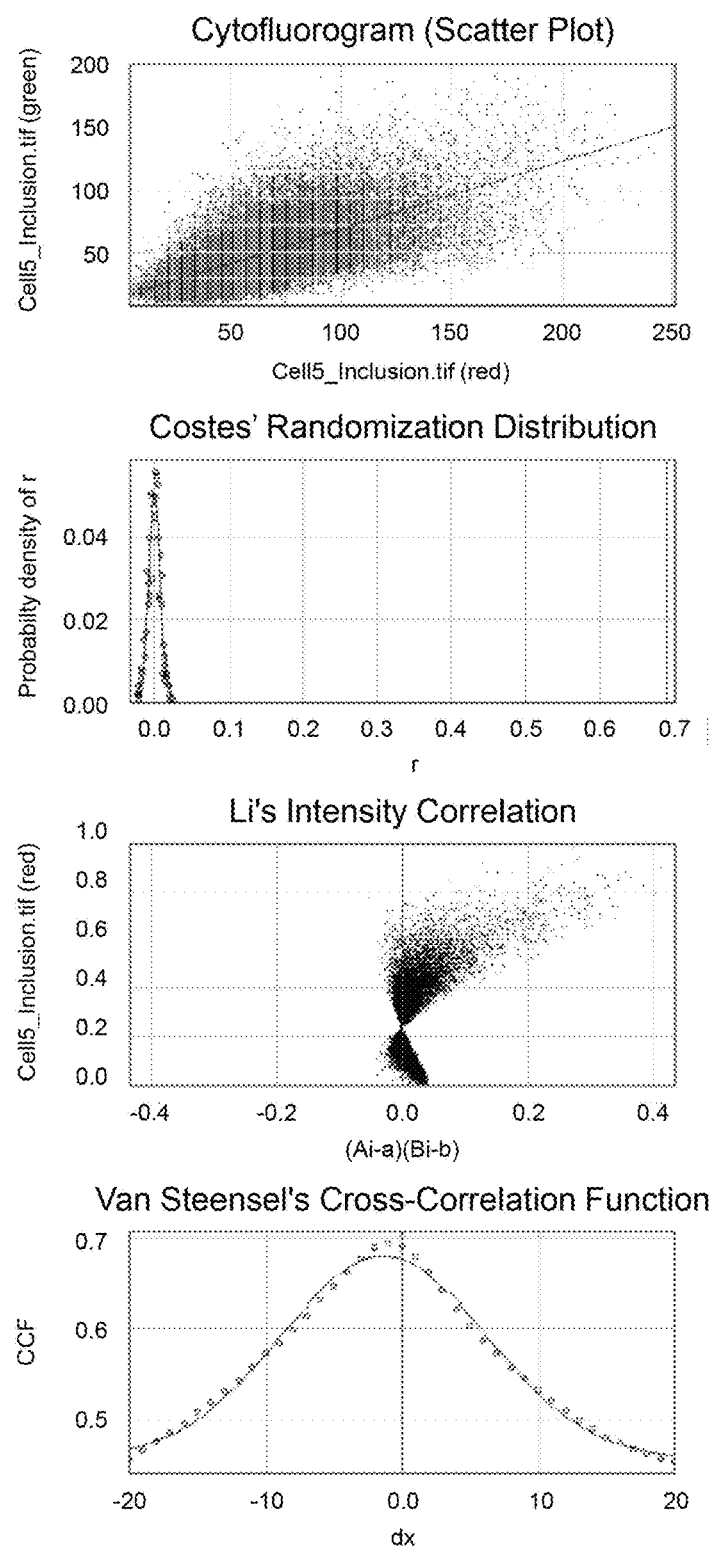
Figure 26:
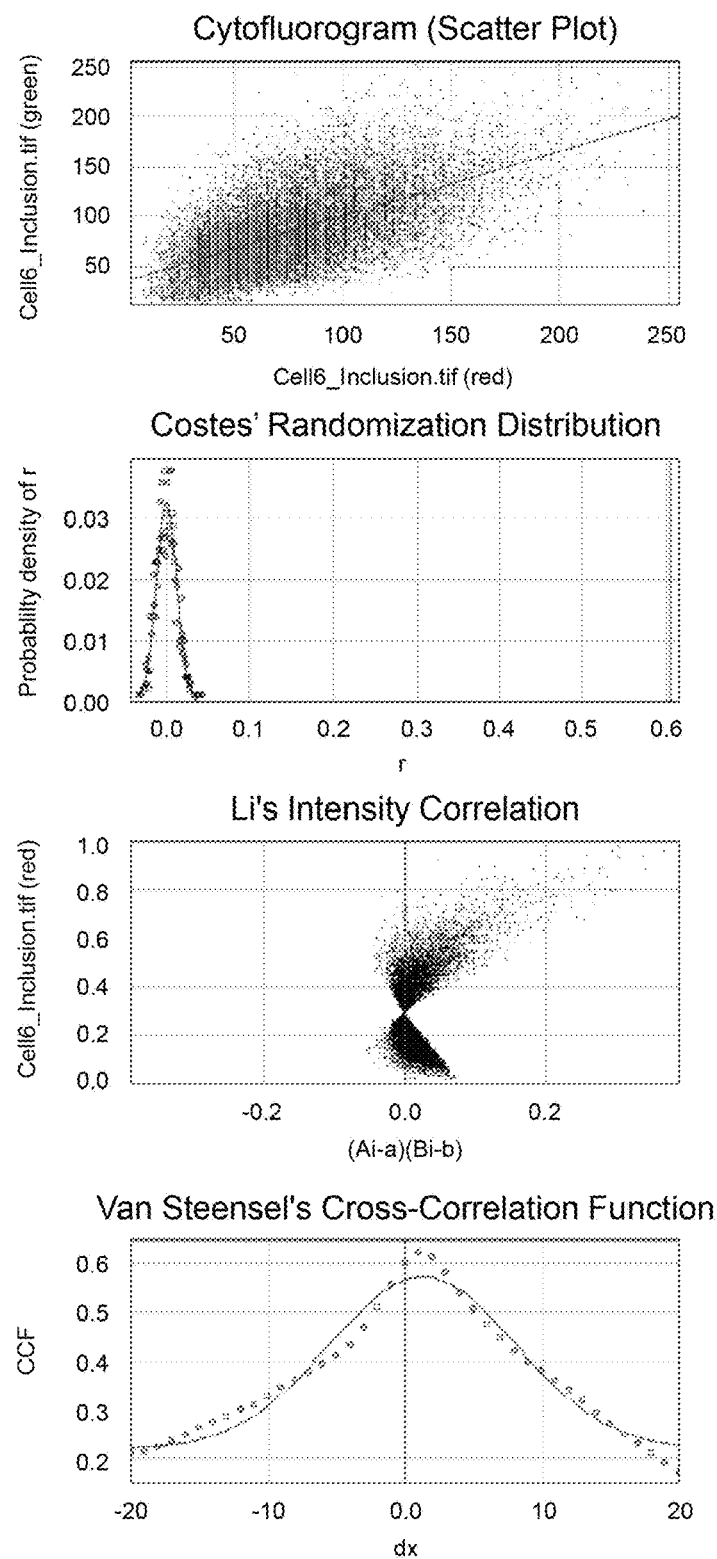
Figure 27:
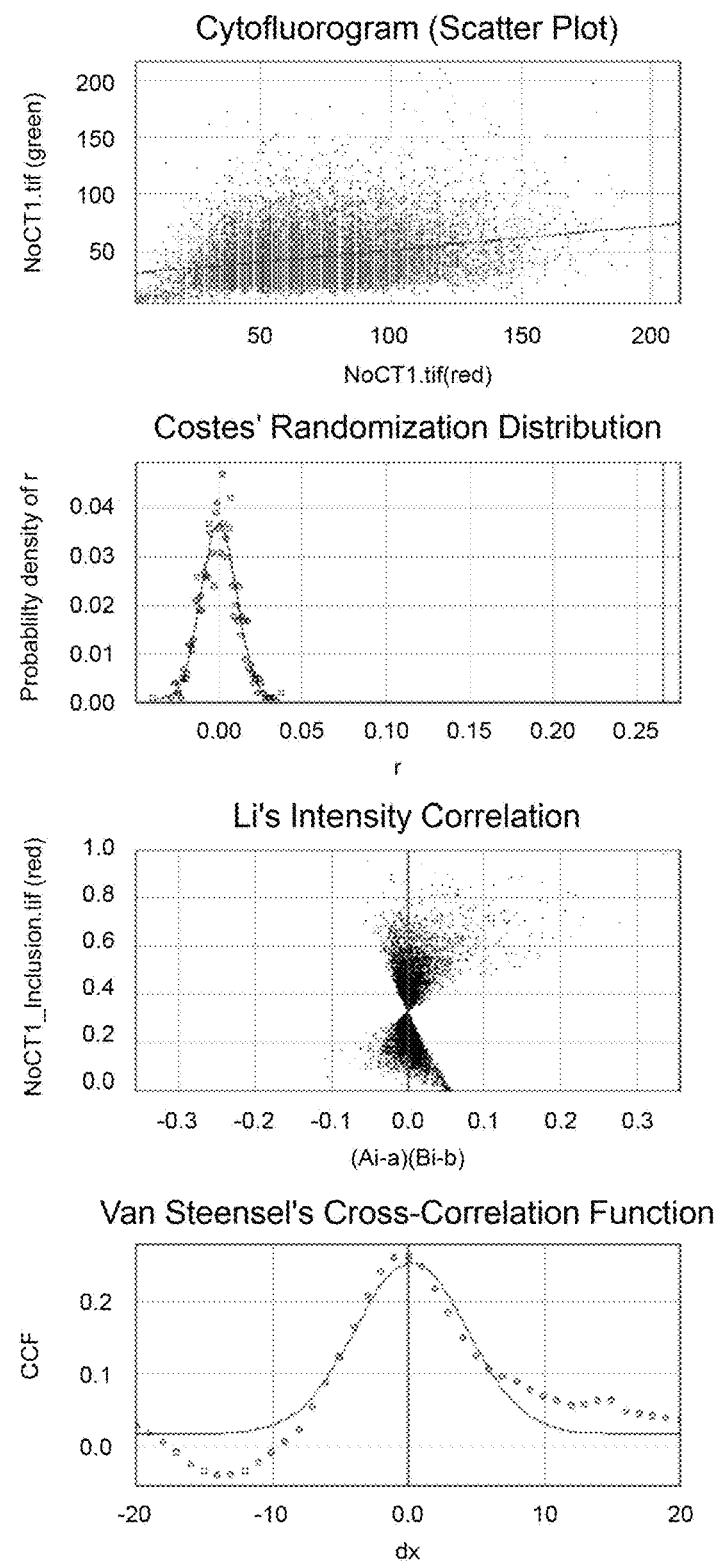
Figure 28:
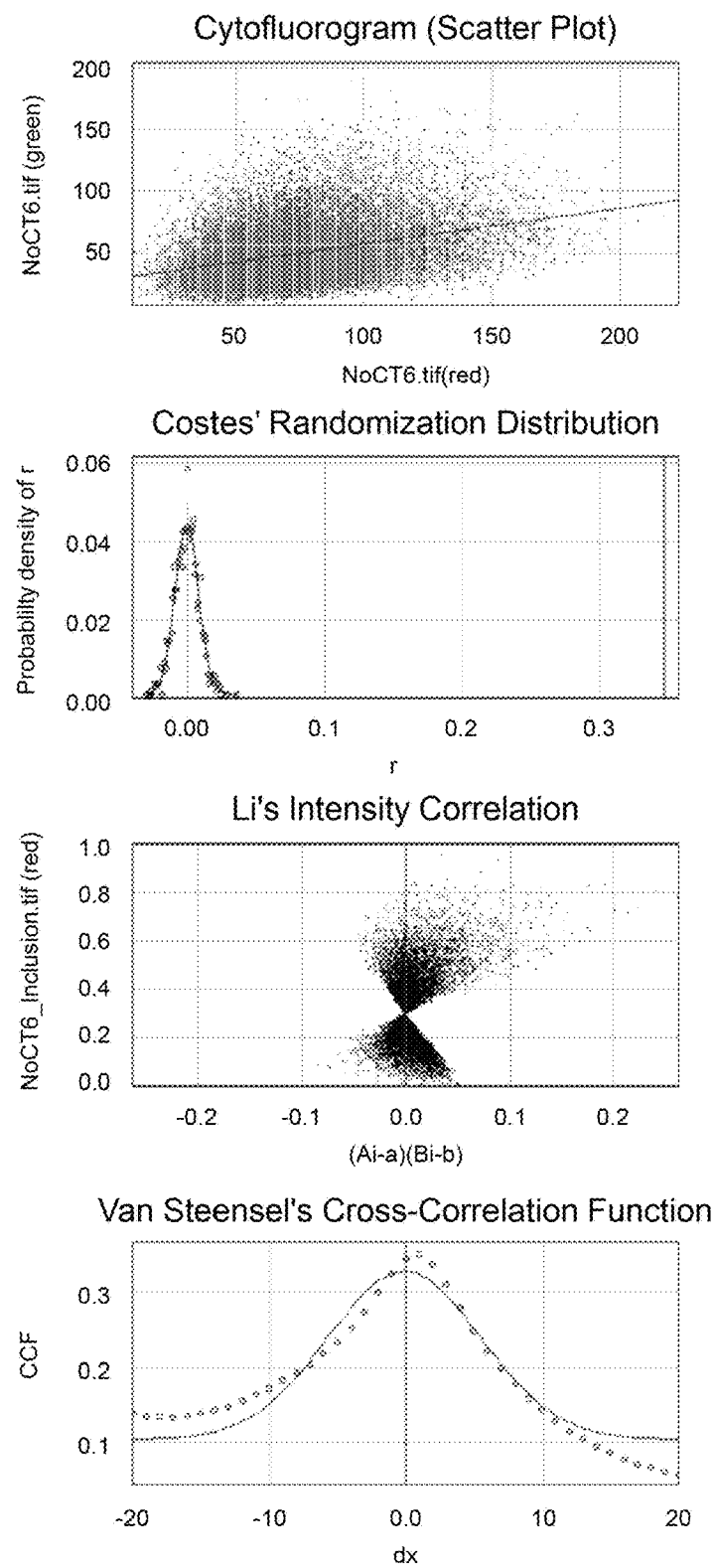
Figure 29:
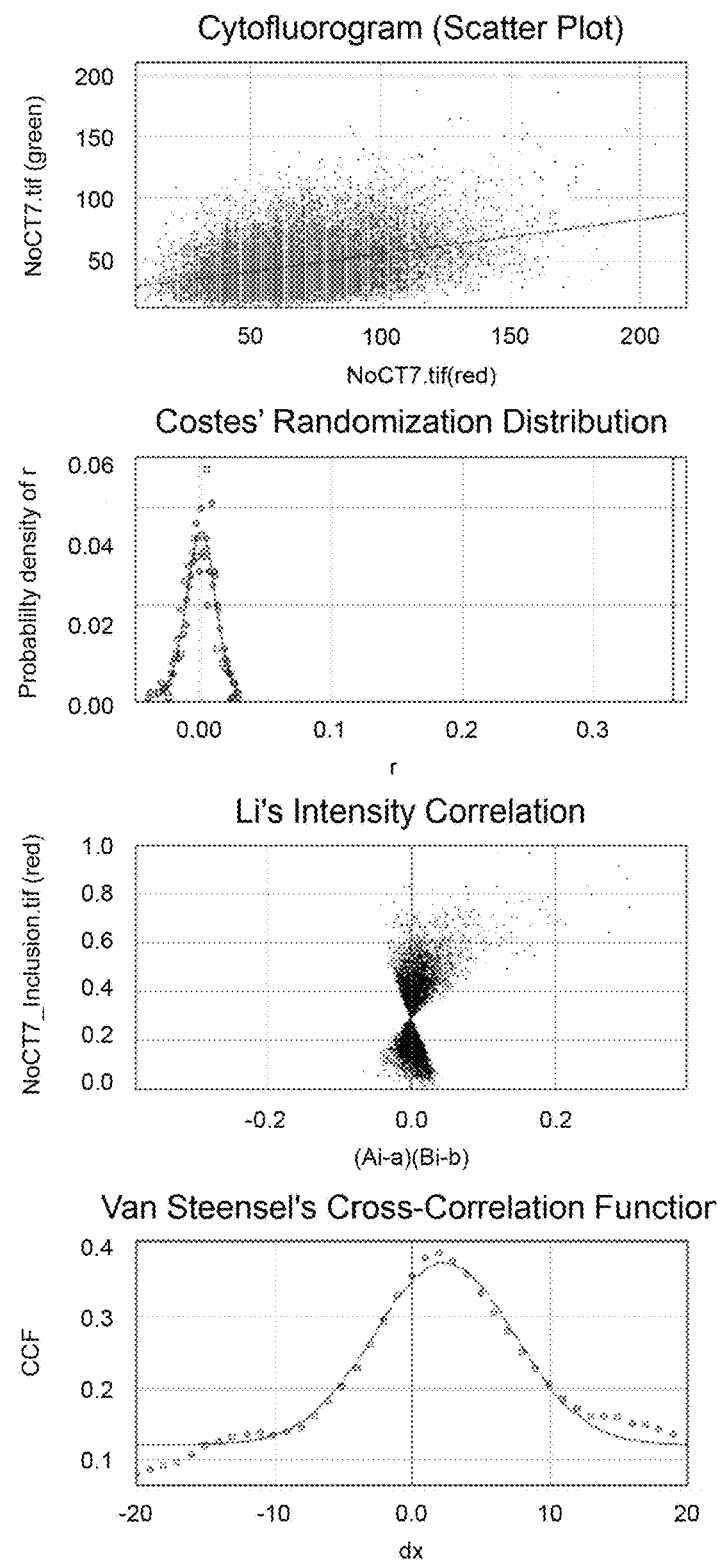

Because we observed PDGFRβ phosphorylation triggered by *C. trachomatis* infection (FIG. 1, Panel F) and the role of PDGFRβ has been established in *C. muridarum* attachment to host cells, we also investigated the formation of chlamydial inclusions in cells treated with PDGFRβ siRNA. The depletion of PDGFRβ in HeLa cells treated with PDGFRβ siRNA was confirmed by Western blot (FIG. 16). Similar to EGFR, depletion of PDGFRβ decreased the number of inclusions in host cells (P<0.01); however, unlike EGFR, the size of the inclusions was not significantly affected by PDGFRβ siRNA treatment (FIG. 4, Panel A and FIG. 22). These results were further substantiated by experiments in MEFs EGFR$^{-/-}$ cells, which showed similar results to the EGFR-inhibited HeLa cells (FIG. 4, Panel B and FIG. 17). We then examined the possible role of EGFR in the bacterial attachment to the cell surface and its subsequent internalization, during the early stage of *C. trachomatis* infection. The PDGFRβ siRNA treated HeLa cells were included as control in these experiments. HeLa cells with or without EGFR and PDGFRβ inhibition were infected with *C. trachomatis* for 2.5 h and processed for inside-out staining to differentially quantify external and internalized bacteria. At 2.5 hpi a significant decrease in cell-associated bacteria (external and internal) was observed (P<0.05 to P<0.001) in both EGFR and PDGFRβ inhibited cells (FIG. 4, Panels C-D). Since more than 80% of the cell-associated bacteria were successfully internalized into the host cell (FIG. 4, Panels C-D), these results point to defects in bacterial attachment to the host cell as a main cause for the decrease in overall chlamydial internalization. The results were further confirmed by Western blot analysis of chlamydial Hsp60 (P<0.001; FIG. 4, Panels E-F).

The small inclusions formed upon inhibition of EGFR were examined in detail by transmission electron microscopy experiments. Large inclusions were observed in HeLa cells infected with *C. trachomatis* whereas the Erlotinib and Cetuximab treated HeLa cells contained small inclusions (FIG. 4, Panels G-H).

Figure 5:
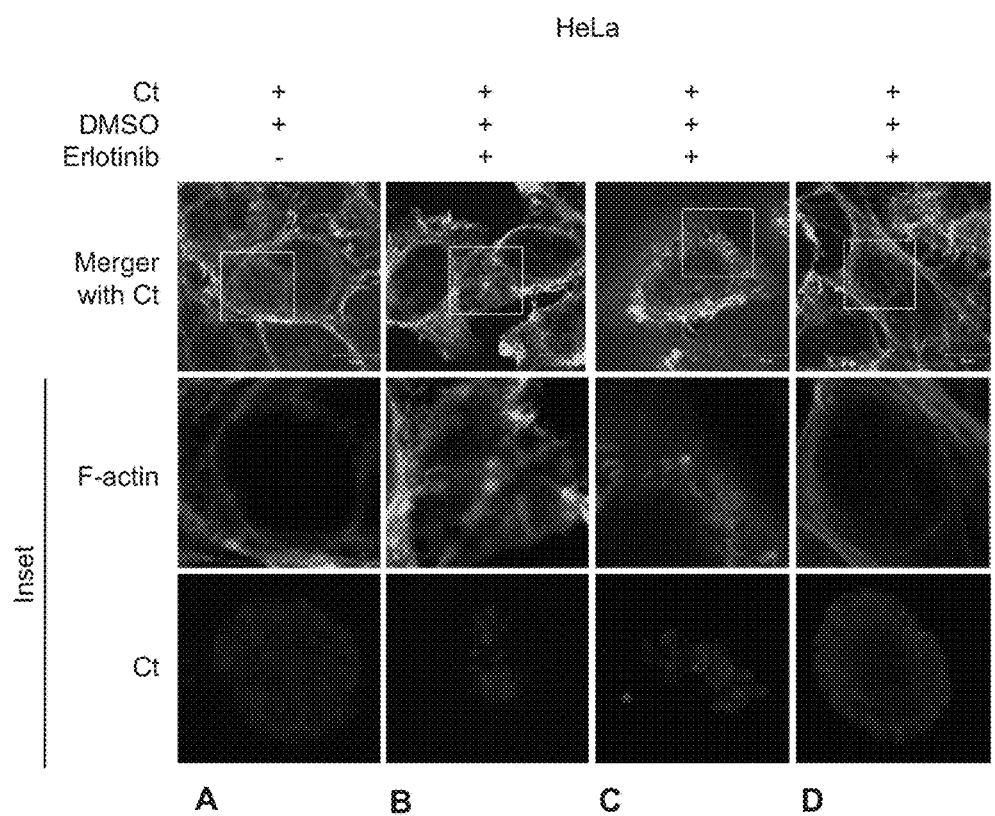
FIG. 5. EGFR is essential for development of chlamydial inclusion post-bacterial entry. (Panels A-D) HeLa cells were infected with *C. trachomatis* for 24 h. In Panels B-D, EGFR inhibitor Erlotinib was added at 2.5, 5 and 18 hpi, respectively. Under all conditions the total time for *C. trachomatis* infection was 24 h followed by fixing, and processing for confocal microscopy. F-actin was detected with Alexa Fluor 488-phalloidin and chlamydial inclusions were detected using anti-chlamydial LPS antibody. Well-developed *C. trachomatis* inclusions were observed in the DMSO treated cells (Panel A) and in cells treated with Erlotinib at 18 hpi (Panel D); while incomplete inclusion development and bacterial aggregates were observed in cells treated with Erlotinib at 2.5 hpi (Panel B) and 5 hpi (Panel C). F-actin staining of HeLa cells with Erlotinib treatment but without *C. trachomatis* infection is shown in FIG. 21. Scale bar—10 mm.
Figure 18:
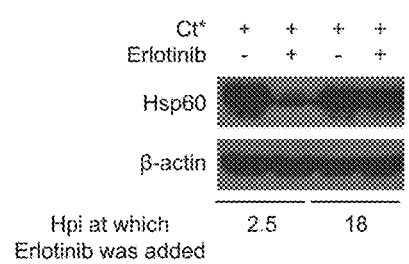
FIG. 18. Western blot analysis of chlamydial Hsp60. HeLa cells were infected with Ct and then treated with Erlotinib (25 µM) at either 2.5 hpi or 18 hpi. The total time for Ct infection was 24 h followed by Western blotting with anti-chlamydial Hsp60 antibody. Significant decrease in the Hsp60 was observed in cells treated with Erlotinib at 2.5 hours post Ct infection but not in cells treated with Erlotinab at 18 hpi. β-actin was used as loading control.

To further distinguish between the role of EGFR in bacterial attachment from the growth-associated consequences during *C. trachomatis* infection, experiments were performed in which EGFR inhibitor (Erlotinib) was added at different time points (2.5, 5 and 18 hpi), post bacterial infection. Under all conditions the total time of infection with *C. trachomatis* was 24 h. EGFR inhibition after 2.5 and 5 hpi, impaired regular inclusion formation and resulted in formation of numerous bacterial aggregates (FIG. 5, Panels B and C, respectively). On the other hand, EGFR inhibition at 18 hpi did not significantly affect the inclusion development (FIG. 5, Panel D). These observations correlate well with the pattern of EGFR signaling shown in FIG. 2, Panels A-B. The results were further confirmed by Western blot analysis of chlamydial Hsp60. Significantly lower expression of Hsp60 was noted in cells treated with Erlotinib at 2.5 hpi compared with Erlotinib addition at 18 hpi (cells harvested at 24 hpi; FIG. 18). Together, the results described above show that EGFR has discrete functions both at the level of bacterial attachment/internalization and subsequent inclusion development.

Figure 6:
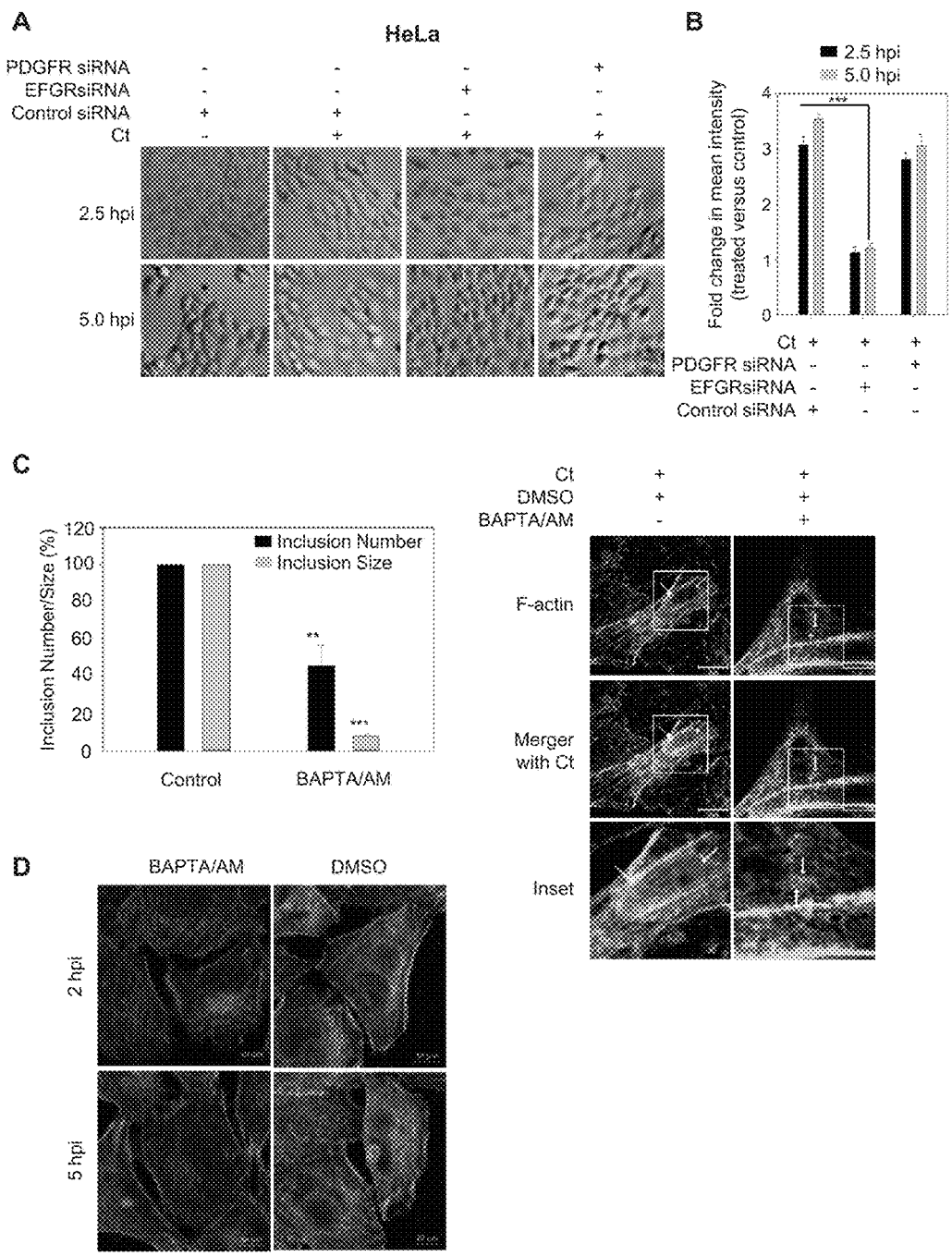
FIG. 6. EGFR is required for *C. trachomatis*-induced calcium mobilization. (Panels A-B) Calcium mobilization induced by *C. trachomatis* infection. HeLa cells treated with control siRNA, EGFR siRNA or PDGFRβ siRNA were infected with *C. trachomatis* for 2.5 h or 5 h and stained with Fluo-4 AM for visualization of calcium ($Ca^{2+}$) by fluorescence microscopy. The fluorescence intensity of calcium staining from three independent experiments was quantified using ImageJ (Panel B). Note the weak calcium signal in EGFR inhibited cells (P<0.001) whereas in the case of PDGFRβ inhibition the levels of calcium induced by *C. trachomatis* are equivalent as in control cells infected with *C. trachomatis*, indicating that EGFR is required for *C. trachomatis*-induced increase in calcium levels. (Panel C) Inclusion development and organization of F-actin at the chlamydial inclusion periphery. HeLa cells were pre-treated with BAPTA/AM (a calcium chelator) for 1 h followed by infection with *C. trachomatis* for 24 h, fixed, and processed for confocal microscopy. Data from three independent experiments were analyzed for number and size of inclusions that were significantly reduced in BAPTA/AM treated cells (left panel). F-actin was detected with Alexa Fluor 488-phalloidin and chlamydial inclusions were detected using anti-chlamydial LPS antibody (right panel). Note the diffused assembly of F-actin at the inclusion periphery (arrow). (Panel D) Inclusion development in post infection BAPTA/AM treated cells. HeLa cells were infected with *C. trachomatis* for 24 h. BAPTA/AM or control DMSO was added at 2 or 5 hpi. Under all conditions the total time for *C. trachomatis* infection was 24 h followed by fixing, and processing for confocal microscopy. F-actin was detected with Alexa Fluor 488-phalloidin and chlamydial inclusions were detected using anti-*C. trachomatis* EB antibody. Data are representative of two independent experiments. Note the impaired inclusion development in BAPTA/AM treated cells in comparison to the DMSO treated cells. F-actin staining for HeLa cells with BAPTA/AM treatment but without *C. trachomatis* infection is also shown in FIG. 21. Scale bar—10 mm.
Figure 19:
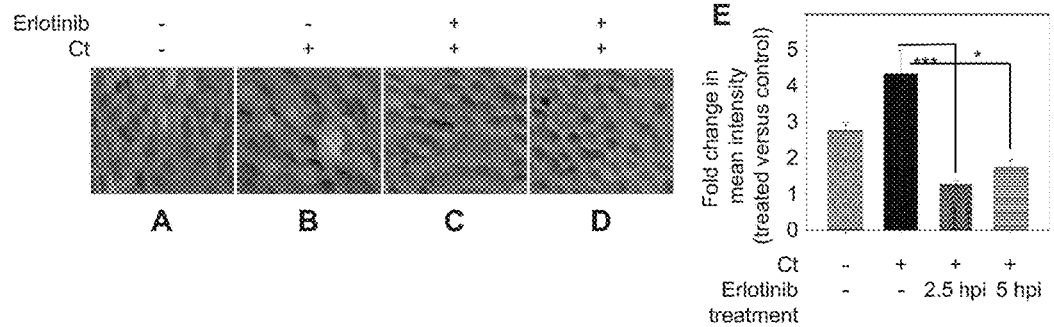
FIG. 19. HeLa cells were infected with Ct for 24 h. In Panels C-D, EGFR inhibitor Erlotinib was added at 2.5 and 5 hpi, respectively. Under all conditions the total time for Ct infection was 24 h and cells were stained with Fluo-4 AM for visualization of calcium (Ca$^{2+}$) by fluorescence microscopy. (Panel E) The fluorescence intensity of calcium staining shown in Panels A-D was quantified using Image J. Note the weak calcium signal in EGFR inhibited cells (P<0.05) in comparison with cells infected with Ct in the absence of Erlotinib.
Figure 20:
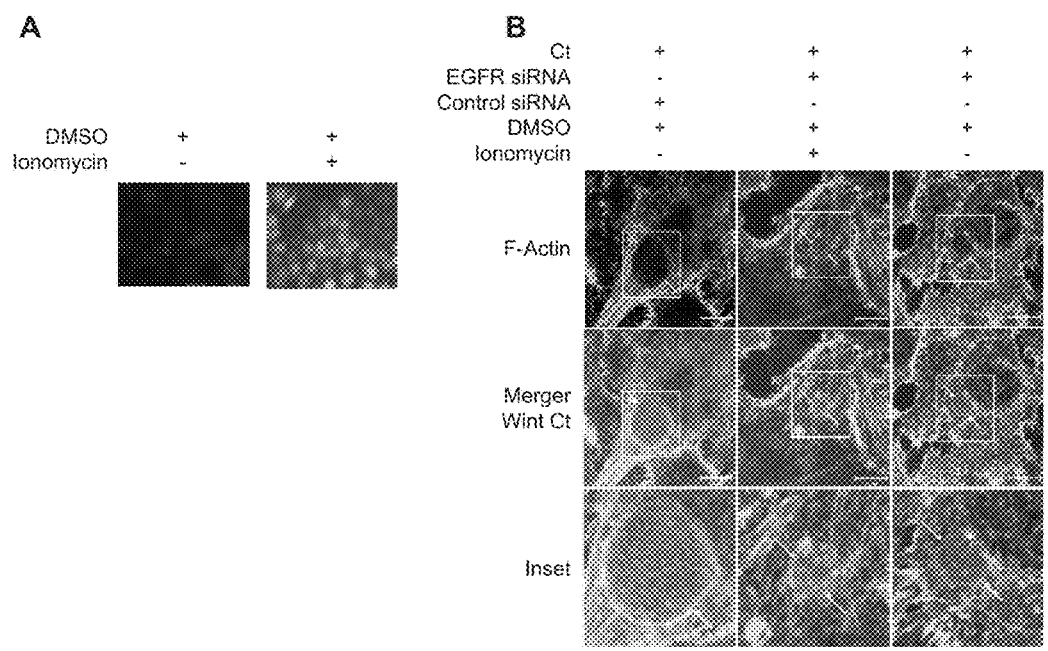
FIG. 20. Effect of Ionomycin treatment on inclusion formation. (Panel A) HeLa cells were treated with Ionomycin (1 µg/ml) for 1 h and stained with Fura-2/AM for visualization of calcium (Ca$^{2+}$) by fluorescence microscopy. Increased intracellular free calcium was observed with Ionomycin treatment. (Panel B) HeLa cells treated with EGFR siRNA with or without one hour pre-treatment with Ionomycin (1 µg/ml) were infected with Ct for 24 h and fixed, and processed for confocal microscopy to compare the inclusion formation in comparison to the Ct-infected control cells. F-actin was detected with Alexa Fluor 488-phalloidin and chlamydial inclusions were detected using anti-chlamydial LPS antibody. In comparison to control, small inclusions were formed in the EGFR depleted cells and no significant difference was observed between the inclusions formed in EGFR siRNA treated cells with or without Ionomycin treatment. Scale bar—10 µm.
Figure 21:
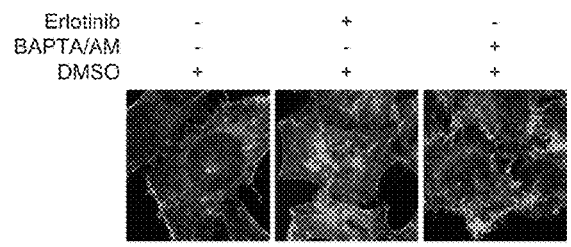
FIG. 21. F-actin staining in HeLa cells. F-actin staining was performed with Alexa Fluor 488-phalloidin in HeLa cells treated with Erlotinib or BAPTA/AM. F-actin staining for untreated HeLa cells is also shown.

EGFR regulates intracellular calcium during *C. trachomatis* infection. We next tested whether EGFR could be involved in *C. trachomatis*-induced calcium release in host cells. HeLa cells were treated with control siRNA, EGFR siRNA or PDGFRβ siRNA followed by *C. trachomatis* infection. At 2.5 and 5 hpi cells were analyzed by fluorescence microscopy for intracellular calcium. At 2.5 and 5 hpi, a significant increase in calcium was observed upon *C. trachomatis* infection in control siRNA and PDGFRβ siRNA treated cells but not in EGFR siRNA treated cells (FIG. 6, Panels A-B; P<0.001). In another set of experiments, Erlotinib was added at 2.5 and 5 hpi and cells were incubated for up to 24 hpi when they were stained for calcium. A significant drop in calcium signal was observed in *C. trachomatis*-infected cells that had been treated with Erlotinib at 2.5 and 5 hpi (FIG. 19). Examination of these results, in combination with the observations described in FIG. 5 suggests that EGFR-induced calcium release is necessary for the development of *C. trachomatis* inclusions. Next, we mimicked a calcium deficient environment by treating HeLa cells with the calcium chelator BAPTA/AM for 1 h followed by *C. trachomatis* infection for 24 h. A significant decrease in both inclusion size and number was noted, similar to the conditions of EGFR inhibition in HeLa cells (FIG. 6, Panel C). Impaired inclusion formation was also observed in *C. trachomatis*-infected cells treated with BAPTA/AM at 2 and 5 hpi (more severe in 2 hpi BAPTA/AM treated cells) compared with the control DMSO treated cells (FIG. 6, Panel D). The addition of Ionomycin (a calcium ionophore) to EGFR siRNA treated cells was not able to rescue the formation of chlamydial inclusion (FIG. 20). This shows that a coordinated and synchronized regulation of EGFR-dependent calcium release along with other factors regulated by EGFR are required for formation of inclusions within the host cells.

Figure 7:
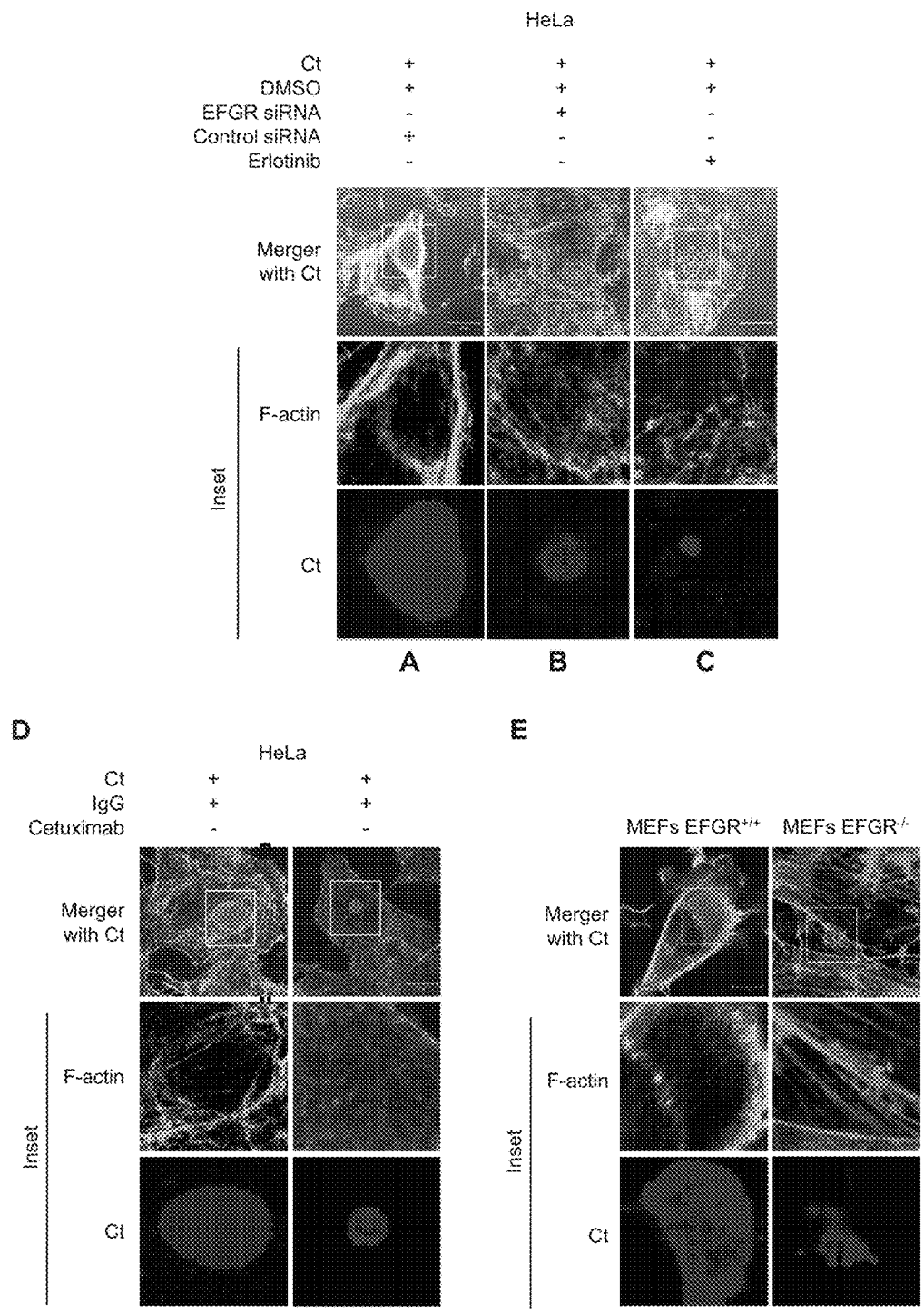
FIG. 7. EGFR is required for the reorganization of F-actin at the periphery of chlamydial inclusions. (Panels A-C) Organization of F-actin at the chlamydial inclusion periphery. HeLa cells treated with (Panel A) control siRNA, (Panel B) EGFR siRNA or (Panel C) Erlotinib, were infected with *C. trachomatis* for 24 h, fixed, and processed for confocal microscopy. F-actin was detected with Alexa Fluor 488-phalloidin and chlamydial inclusions were detected using anti-chlamydial LPS antibody. Note the distinct assembly of F-actin at the inclusion periphery in (Panel A) which is altered upon inhibition of EGFR (Panels B-C). (Panel D) HeLa cells treated with IgG or Cetuximab were infected with Ct for 24 h, fixed, and processed for confocal microscopy. F-actin was detected with Alexa Fluor 488-phalloidin and chlamydial inclusions were detected using anti-chlamydial LPS antibody. Note the distinct assembly of F-actin at the inclusion periphery in IgG treated cells and the lack of it in Cetuximab treated cells. Scale bar—10 μm. (Panel E) Organization of F-actin at the chlamydial inclusion periphery in MEFs EFGR$^{+/+}$ and MEFs EGFR$^{-/-}$. MEFs EGFR$^{+/+}$ and MEFs EGFR$^{-/-}$ were infected and processed as in (Panel A). F-actin is noticeably rearranged at the chlamydial inclusion periphery in the MEFs EFGR$^{+/+}$ but not in the MEFs EGFR$^{-/-}$ cells.

EGFR is essential for F-actin assembly around chlamydial inclusions. To examine the role of EGFR in arrangement of F-actin at the inclusion periphery, HeLa cells treated with Erlotinib, Cetuximab, and EGFR siRNA were infected with *C. trachomatis* for 24 h and processed for confocal microscopy to visualize the intracellular arrangement of F-actin. We observed formation of a distinct F-actin ring at the inclusion periphery in *C. trachomatis* infected control cells (DMSO, control siRNA or IgG control) (FIG. 7, Panel A and Panel D). In the EGFR siRNA treated cells, the arrangement of F-actin around the *C. trachomatis* inclusion was either diffused or disorganized (FIG. 7, Panel B). Similar results were observed in the Erlotinib and Cetuximab treated HeLa cells (FIG. 7, Panels C-D), as well as in the MEFs EGFR$^{+/+}$ cells (FIG. 7, Panel E).

Figure 8:
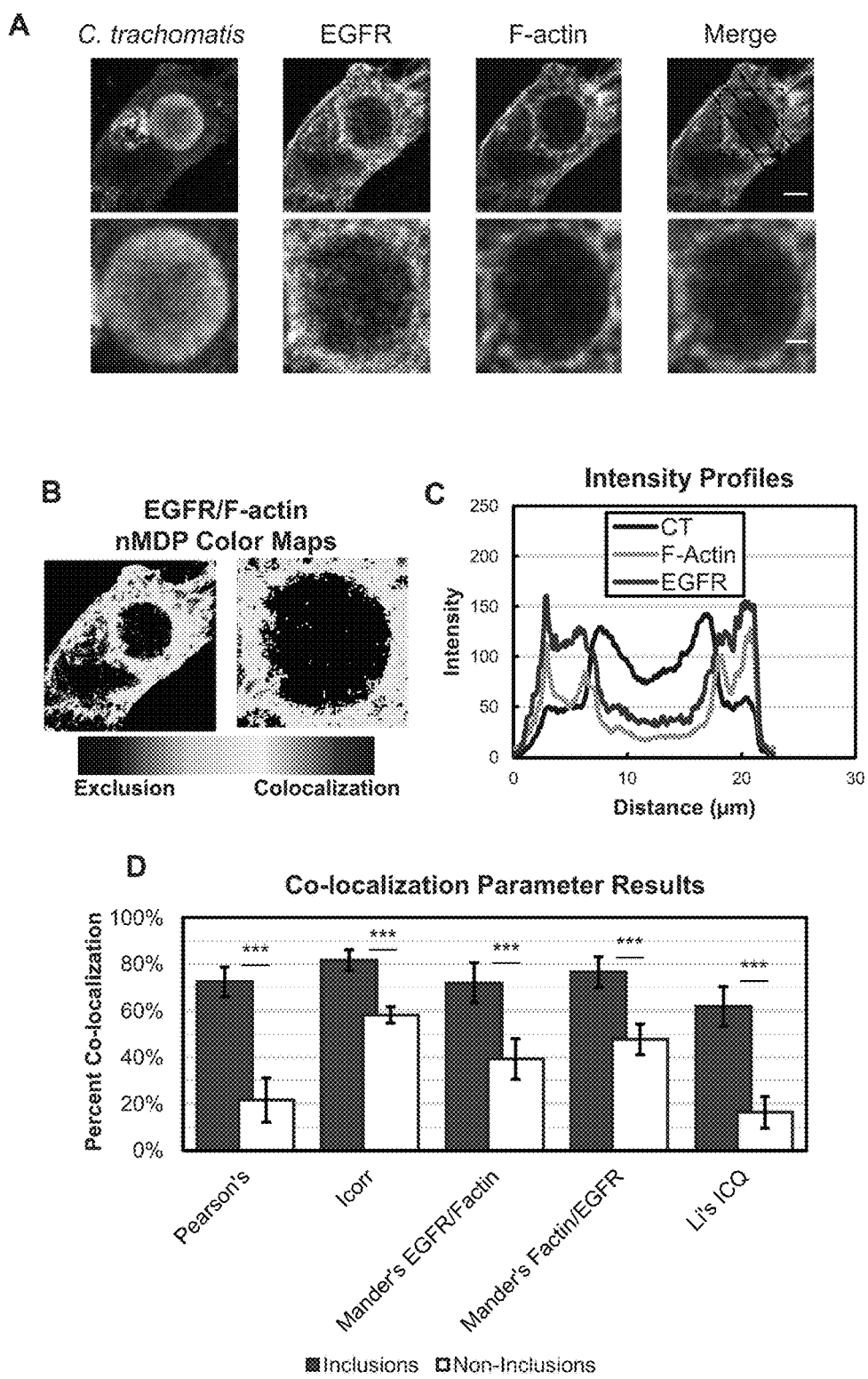
FIG. 8. Co-localization of EGFR and F-actin at the periphery of *C. trachomatis* inclusion. (Panel A) HeLa cells were infected with *C. trachomatis* for 24 h, fixed and processed for confocal imaging to detect *C. trachomatis*, F-actin and EGFR. The merged image shows co-localization of EGFR and F-actin. Dashed box represents the inclusion area, solid box represents area and direction of intensity profile measurement in (Panel C). Scale bars are 5 µm and 2 µm in whole cell and inclusion area images, respectively. (Panel B) nMDP color maps showing heat maps of co-localization areas in whole cell and inclusion area images. Both cell and inclusion boundaries show similar evidence of co-localization ranging from moderate to intense. (Panel C) Intensity profiles of *C. trachomatis*, EGFR, and F-actin from cell boundary to cell boundary across the inclusion. EGFR and F-actin signals rise and fall in similar patterns along the inclusion boundary (located at approximately 6 µm and 18 µm on the x-axis) indicating co-localization in a similar manner as at the cell boundary (located at approximately 3 µm and 21 µm on the x-axis). (Panel D) Comparison of co-localization parameters between inclusion area images and non-inclusion area images (details in the legend for FIGS. 23-29). All five parameters show significant increase of co-localization in inclusion areas compared with non-inclusion areas. Data presented represent the mean±standard deviation; n=8 images within each subset, ***p<0.001.

Since EGFR is an F-actin binding protein, we performed additional experiments to investigate whether EGFR co-localizes with F-actin ring at the periphery of inclusion. HeLa cells were infected with *C. trachomatis* and at 24 hpi the cells were stained for *C. trachomatis* EB, EGFR and F-actin (FIG. 8, Panel A). Co-localization of EGFR and F-actin at the periphery of *C. trachomatis* inclusion was evidenced by overlapping fluorescence signals (FIG. 8, Panel A, Merge). The normalized mean deviation product (nMDP) was calculated for each pixel in the image to identify regions of intense co-localization or exclusion within the image. The resulting nMDP color maps of the whole cell and the inclusion area (dashed box in FIG. 8, Panel A) show areas with co-localization ranging from moderate to intense, with no areas of exclusion (FIG. 8, Panel B). The intensity profile for a cross-section in FIG. 8, Panel A, which includes from top left to bottom right (left to right in the intensity profile plot), shows clear enrichment of EGFR and F-actin at the periphery of inclusion as well as the cell membrane (FIG. 8, Panel C). Quantitative processing of the image data shown in FIG. 8 was performed using a number of independent algorithms, which are described in the legend for FIGS. 23-29. Similar analysis was applied to other 7 inclusion areas and 8 non-inclusion areas (cells that were not infected with *C. trachomatis*) and all five parameters show significant increase of EGFR and F-actin co-localization in inclusion areas compared with non-inclusion areas (p<0.001, FIG. 8, Panel D). Additional representative images and analyses are shown in FIGS. 24-29. Collectively, all quantitative analyses show strong and statistically significant evidence o f co-localization of EGFR and F-actin at the periphery of inclusion.

As an intracellular pathogen, *C. trachomatis* has developed an arsenal of molecular tools that enables it to hijack signaling and metabolic pathways of the host cell and establish an intracellular niche favorable to its development. An extensive network of interactions exists between *C. trachomatis* and host proteins to facilitate bacterial attachment and entry and *C. trachomatis* development in the host cell. *C. trachomatis* can interact with and modulate the activity of numerous cell surface receptors to promote attachment and entry into the host cell. EGFR is an important cell surface receptor tyrosine kinase with a central role in cell growth, proliferation and migration. We provide here the first evidence that *C. trachomatis* has the ability to upregulate EGFR activity in host cells and establish EGFR as a critical effector molecule in the formation of chlamydial inclusions within the host cells.

We demonstrate that *C. trachomatis* induces an increase in EGFR phosphorylation and that inhibition of EGFR phosphorylation or depletion of EGFR protein impairs *C. trachomatis* attachment and its development in the host cells. Our results are further supported by the EGFR-dependent increase in phosphorylation of downstream targets like Akt, STAT5 and PLCγ1 in *C. trachomatis* infected cells. The lack of Akt phosphorylation in EGFR$^{-/-}$ cells demonstrates EGFR as the upstream regulator of Akt phosphorylation, which was not known before.

We demonstrate here that inhibition of EGFR abrogates the *C. trachomatis*-induced increase in intracellular calcium flux. Also, removal of calcium by chelation resulted in marked reduction in the size and number of chlamydial inclusion similar to EGFR inhibition.

Our data show distinct co-localization of EGFR with the F-actin ring around the chlamydial inclusion and interruption in the formation of F-actin rings around the chlamydial inclusions in both calcium depleted and EGFR inhibited cells.

EGFR-dependent regulation of F-actin and calcium release can affect inclusion formation at multiple stages of *C. trachomatis* infection. First, it can have a direct effect on the bacterial attachment and entry. Consistent with this, our data indicate that EGFR inhibition significantly impairs the bacterial attachment to the host cell surface at a level comparable with inhibition of PDGFRβ

Figure 9:
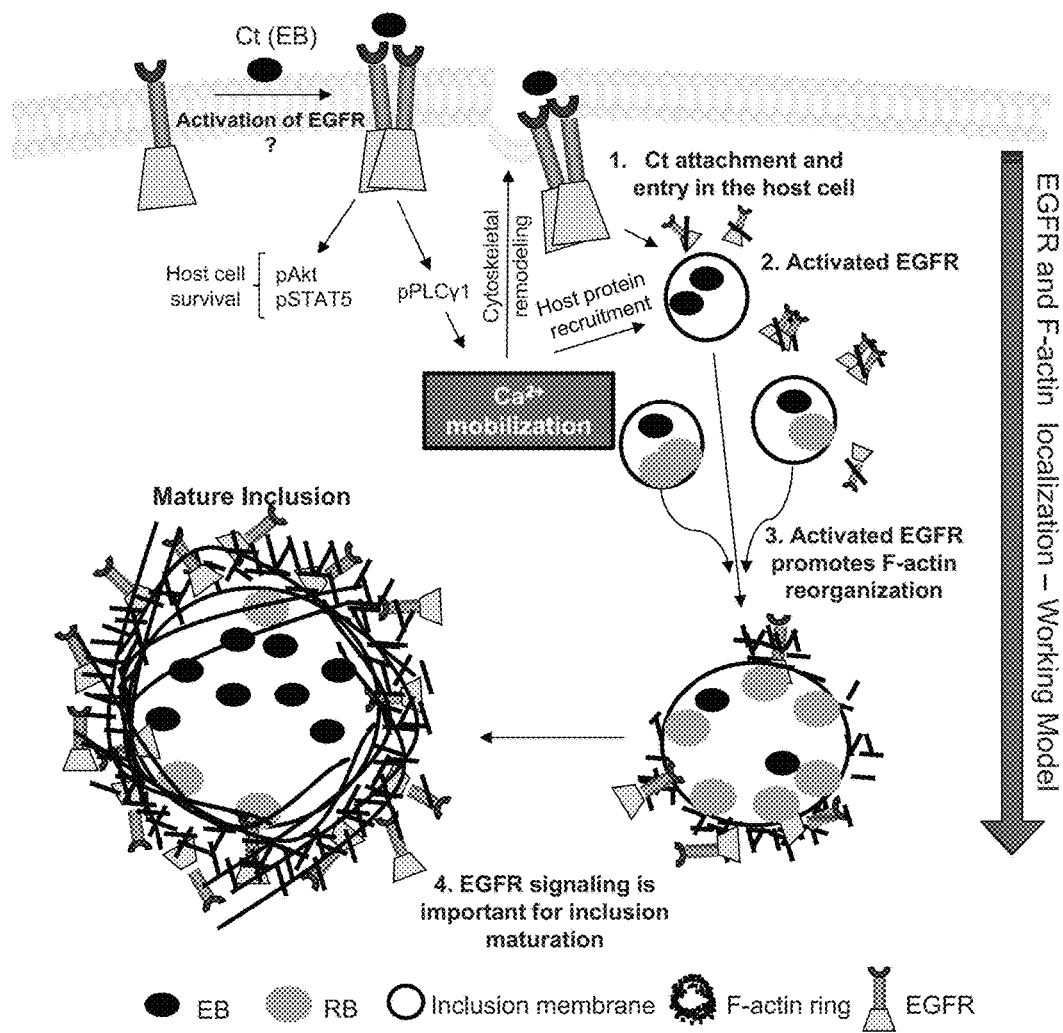
FIG. 9. Proposed model of EGFR involvement at various stages of *C. trachomatis* infection. *C. trachomatis* infection induces EGFR phosphorylation and activation of downstream targets like Akt, STAT5 and PLCγ1. Activation of EGFR signaling can upregulate host cell survival mechanisms and induce increased calcium mobilization. EGFR co-localization with F-actin is suggestive of a possible direct role of EGFR in formation of F-actin rings at the periphery of inclusion. The increased calcium signaling can have several functions ranging from cytoskeletal remodeling to recruitment of host proteins at the inclusion membrane. The EGFR-induced formation of F-actin ring and other cytoskeletal elements at the inclusion periphery can further aid in inclusion expansion via vesicular trafficking and nutrient uptake.

In summary, the studies included here show that chlamydial infection upregulates EGFR activity in host cells. This results in activation of downstream effectors of EGFR such as PLCγ1, Akt and STAT5. We demonstrate that EGFR and EGFR-mediated signaling play a role in both *C. trachomatis* attachment and development of *C. trachomatis* inclusions in host cells through mechanisms that involve EGFR-dependent regulation of calcium release, actin cytoskeleton rearrangement, and EGFR co-localization with F-actin at the inclusion periphery. These findings shed light on the complexity of *C. trachomatis*-host cell interactions, which open new venues to treat *C. trachomatis* infections and *C. trachomatis*-associated diseases. These results form the basis of the model we propose in FIG. 9. In this model, EGFR plays a key role in the early and middle stages of *C. trachomatis* infection wherein the EGFR mediated calcium signaling and F-actin remodeling are central to the establishment of a successful *C. trachomatis* infection inside the eukaryotic cells.

Reagents. Antibodies were obtained from the following sources: goat anti-chlamydial LPS, goat anti-*C. trachomatis* EB (Meridian Life Sciences, Saco, Me., USA); FITC conjugated anti-chlamydial EBs (Fitzgerald, Mass., USA), rabbit anti-EGFR, rabbit anti-PLCγ1, rabbit anti-pPLCγ1, rabbit anti-Stat5, rabbit anti-pStat5, rabbit anti-Akt, rabbit anti-pAkt, rabbit anti-pPDFGRβ (Y751), rabbit anti-EGFR (Alexa Fluor 594 conjugate) and rabbit anti-β actin (Cell Signaling, Danvers, Mass., USA); rabbit anti-pEGFR (Y1173), rabbit anti-PDGFRβ, mouse anti-chlamydial Hsp60 and rabbit anti-mouse IgG HRP antibodies (Santa Cruz Biotechnology, Santa Cruz, Calif., USA); rabbit anti-pEGFR antibodies (Y845, Y992, Y1045, Y1148; Millipore, Temecula, Calif., USA); donkey anti-goat IgG H&L (Alexa Fluor 405) (Abcam, Cambridge, Mass., USA); anti-EGFR-Alexa Fluor 488 antibody (Millipore, Temecula, Calif., USA), goat anti-rabbit IgG HRP, FITC-conjugated anti-rabbit antibody and rhodamine red conjugated anti-goat secondary antibodies (Jackson Laboratories, West Grove, Pa., USA). EGFR siRNA (human and mouse), PDGFRβ siRNA (human), control siRNA and siRNA transfection reagents were obtained from Santa Cruz Biotechnology, Santa Cruz, Calif., USA and Dharmacon USA. DMEM, DMEM (Ca$^{++}$ free), FCS, FBS and Alexa Fluor 488 phalloidin and Fluo-4 AM were purchased from Invitrogen, Grand Island, N.Y., USA. Pathfinder *Chlamydia* Culture Confirmation System was purchased from BioRad, Hercules, Calif., USA. HBSS and PBS were purchased from Lonza, Walkersville, Md., USA. DEAE dextran, BAPTA/AM, Ionomycin, and cyclohexamide were purchased from Sigma Aldrich, St. Louis, Mo., USA. Cell Proliferation Kit I (MTT) and Fast Start Universal SYBR green (Rox) were obtained from Roche, Indianapolis, Ind., USA. Erlotinib was purchased from Selleck Chemicals LLC, Houston, Tex., USA and Cetuximab was obtained from Yale University. Bicinchoninic acid (BCA) assay for protein quantification was purchased from Thermo Scientific, Rockford, Ill., USA. ECL Plus Western blotting detection reagent was purchased from Perkin Elmer, Waltham, Mass., USA.

Cell culture. *Chlamydia trachomatis* strain D, HeLa and NIH 3T3 were purchased from ATCC. Mouse embryonic fibroblasts (MEFs EGFR$^{+/+}$ and EGFR$^{-/-}$) were obtained from the University of Pittsburgh. HeLa and MEFs were cultured using DMEM+10% FBS. NIH 3T3 cells were cultured in DMEM+10% FCS. All cell lines were maintained at 37° C. and 5% $CO_2$.

Propagation of *Chlamydia* and infections. *Chlamydia trachomatis* strain D (*C. trachomatis*) was propagated in HeLa cells grown in complete DMEM containing cyclohexamide (2 μg/ml). After 48 h, infected cells were harvested in sucrose-phosphate-glutamate (SPG) buffer, ruptured by vortexing with 3 mm glass beads. EBs were purified using previously described methods. The resulting bacterial pellet was resuspended in cold SPG buffer with a 21 to 22-gauge injection needle and stored in aliquots at −80° C. For infection, chlamydial EBs were added to cells in monolayer (80% confluence) at a multiplicity of infection (MOI) of 2-10 for all studies included here. Centrifugation was not used during the infection.

Immunoblotting. Cells were harvested and lysed in modified RIPA buffer (50 mM Tris, 150 mM NaCl, 1% sodium deoxycholate, 1% NP-40, 1 mM sodium fluoride) supplemented with protease inhibitor cocktail and phosphatase inhibitor tablet (Roche). For Western blotting of *C. trachomatis* antigens, the *C. trachomatis*-infected cells were lysed in 20 mM HEPES buffer (pH 8.0) containing 8 M urea supplemented with protease inhibitors. Cell lysates were incubated on ice for 1 h and then sonicated briefly. The soluble protein fraction was collected by centrifugation at 10,000 rpm. Total protein was estimated using the BCA method and equal amounts of proteins (10-20 μg) were processed for immunoblotting. Proteins were resolved on 10% SDS polyacrylamide gel and transferred onto a nitrocellulose membrane. The blot was blocked using 3% BSA and incubated with the indicated antibodies. ECL was used to detect the proteins according to the manufacturer's instructions.

siRNA transfections. Cells were grown to 60% confluency followed by transfection with EGFR siRNA/PDGFRβ siRNA or control siRNA (Santa Cruz/Dharmacon) according to manufacturer's protocol. After 24 h, transfected cells were replated for a second round of transfection. After another 24 h, cells were infected with *C. trachomatis* and incubated for different time intervals (siRNA was maintained during the infection) according to the experimental design and were either stained for analyzing the inclusion development or prepared for Western blot analysis.

EGFR inhibitor treatment. Erlotinib and Cetuximab treatments were used for EGFR inhibition. The cells were pretreated with Erlotinib (25 μM) for 2 h and then infected with *C. trachomatis*. For Cetuximab treatment, cells were treated with 20 μg/ml drug for 2 h in DMEM+0.1% FBS followed by *C. trachomatis* infection. The inhibitor concentration was maintained during the infection. In certain experiments in which protein phosphorylation was investigated (FIG. 1, Panels B, D, F and G, FIG. 2, FIG. 3 and FIG. 11) the cells were serum starved overnight before drug treatment and *C. trachomatis* infection. DMSO was used as the vehicle control for Erlotinib and IgG was used as control treatment for Cetuximab. Infected samples were used either for Western blotting or confocal imaging as described below. In another set of experiments the cells were infected with *C. trachomatis* followed by addition of Erlotinib at 2.5, 5 and 18 hpi. The total time for *C. trachomatis* infection was 24 h after which the samples were used for Western blotting or confocal imaging.

Control experiments. Chlamydial EBs were mixed with complete DMEM (DMEM+10% FBS) containing either 25 µM Erlotinib, 20 µg/ml Cetuximab or DMSO and incubated for 2.5 h at 37° C., and centrifuged at 16,000 rpm at 4° C. for 30 minutes. EB pellets were washed and resuspended in SPG buffer and used for subsequent HeLa cell infection. At 24 hpi cells were lysed for Western blotting of chlamydial Hsp60 antigen.

Inside out staining. Differential staining of external and internalized bacteria was performed as described previously and using three independent studies. Briefly, cells were grown overnight in 2-well Lab-Tek chamber slides and treated with either EGFR inhibitors or siRNA as described above and subsequently infected with *Chlamydia* for 2.5 h at 37° C. to allow for bacterial attachment and internalization. For blocking EGFR with Cetuximab, cells were pre-incubated with Cetuximab or control IgG for 2 h before addition of bacteria. Infected cells were washed five times in PBS and fixed in 1% paraformaldehyde (PFA). After fixation, cells were blocked in 5% BSA for 1 h and then incubated with FITC-conjugated antibody against chlamydial EBs for 1 h to stain external EBs. Cells were then permeabilized with 0.1% Triton X-100, blocked again, and incubated with antibody against chlamydial LPS followed by incubation with rhodamine-conjugated anti-goat antibody to stain intracellular and extracellular EBs. Imaging was performed using confocal microscopy (Carl Zeiss, Germany). The quantification for the inside out experiments was performed manually based on the number of attached EBs observed per infected cell. The statistical analysis was based on imaging data collected from fifteen fields containing 3-10 cells per field as described below.

Immunofluorescence. Cells were infected with *C. trachomatis* as described above. The cells were washed 5 times with PBS and fixed at either 2.5 hpi or 24 hpi with 4% PFA for 10 min and blocked with 5% BSA for 1 h. After washing with TBS (50 mM Tris HCl, pH 7.4 and 150 mM NaCl) the cells were permeabilized for 15 min with 0.1% Triton X-100 and again washed with TBS followed by incubation with the indicated primary antibodies overnight. The cells were washed three times (10 min each) with TBS and incubated with appropriate secondary antibodies and Alexa Fluor 488-phalloidin (1:40 dilution in PBS) for 1 h. After repeated washings, the coverslips were mounted and analyzed using Zeiss LSM 510 or 710 laser scanning confocal microscope. For the studies shown in FIG. 1, Panel A, *C. trachomatis* inclusions were stained using the Pathfinder *Chlamydia* Culture Confirmation System (BioRad, Hercules, Calif., USA). At 24 h post *C. trachomatis* infection, cells were fixed with methanol for 10 min at room temperature and stained with the FITC conjugated pathfinder anti-chlamydial mAb according to the manufacturer's protocol (Bio-Rad, Hercules, Calif.). For the co-localization studies, 30,000 HeLa cells were seeded into EZ slide 4-well glass slides (Millipore, Temecula, Calif., USA) and infected with *C. trachomatis* as described above for 2.5 h the next day. Cells were fixed 24 h later in 4% formaldehyde in PBS for 15 min, permeabilized in 0.1% Triton X-100 for 10 min, and blocked in 1% BSA for 1 h at room temperature. Then the cells were incubated with anti-EGFR rabbit mAb (Alexa Fluor 594 conjugate, Cell Signaling, Danvers, Mass., USA) overnight at 4° C., followed by incubation with Alexa Fluor 488 Phalloidin (Invitrogen, Grand Island, N.Y., USA) for 1 h at room temperature. The slides were mounted with Fluoromount mounting medium (Sigma Aldrich, St. Louis, Mo., USA), sealed, and examined using Zeiss 710 laser scanning confocal microscope.

Intracellular calcium staining. Cells were washed with calcium free incomplete DMEM and incubated with 2 µM Fluo-4 AM diluted in $Ca^{2+}$ free incomplete DMEM at 37° C. for 30 min. The cells were then washed with $Ca^{2+}$ free HBSS and analyzed for calcium levels using an Olympus IX71 fluorescence microscope.

BAPTA/AM and Ionomycin treatment. Monolayers of HeLa cells were washed with PBS and replaced with calcium free DMEM+1% FBS and pretreated for 1 h with BAPTA/AM (15 µM) followed by *C. trachomatis* infection for 24 h. BAPTA/AM concentration was maintained during the *C. trachomatis* infection. The control cells were treated with DMSO (<0.1%) followed by 24 h of *C. trachomatis* infection. In another set of experiments, HeLa cells were infected with *C. trachomatis* followed by addition of BAPTA/AM (15 µM) or DMSO at 2 or 5 hpi. The total time for *C. trachomatis* infection was 24 h. To induce mobilization of calcium from intracellular stores to the cytoplasm, cultured cells were pretreated for 1 h with 1 µg/ml Ionomycin before chlamydial infection. *C. trachomatis*-infected cells were washed three times with PBS after 24 hpi and processed for immunofluorescence as described above.

Cell proliferation assay. To ensure that the dose of Erlotinib (25 µM) provided maximal inhibition without affecting cell viability, MTT assays were performed. HeLa cells were cultured for 24 h, treated with 25 µM Erlotinib and incubated at 37° C., 5% $CO_2$ for 24 h. After washing the cells, the procedure for cell viability assay was followed as per manufacturer's instructions (Roche).

Transmission electron microscopy. HeLa cells were infected with *C. trachomatis* as described above. Twenty-four hours post chlamydial infection the cells were washed with PBS and fixed with 2.5% glutaraldehyde in 0.1 N Millonig's buffer (pH 7.2) for 1 h at room temperature. The cells were then washed and post-fixed for 1 h in 1% osmic acid in 0.1 N Millonig's buffer followed by 1 h treatment with 1% uranyl acetate. A graded ethanol series (25%, 50%, 70-75%, 90-95% and 100%) was used to dehydrate the cells prior to embedding in Spurr's resin. Thin sections were then cut with a Reichert ultracut E microtome and stained with 1% uranyl acetate and Reynold's lead citrate solutions, followed by the analysis using 80 kV Tecnai Spirit BioTwin transmission electron microscope.

Image acquisition and statistical analysis. Images of stained cells were acquired in a Z-series on a Zeiss LSM 710 AxioObserver Z.1 inverted laser scanning confocal microscope using a Zeiss Plan-Apochromat 63×/1.3 water-immersion objective with 3× digital zoom at the Wake Forest University Microscopic Imaging Core Facility and Confocal Microscopy Center. Lasers of 405 nm (25 mW diode), 488 nm (35 mW Argon laser), and 594 nm (2 mW He/Ne laser) were used to illuminate the samples and images were captured using a R6357 photomultiplier tube (Hamamatsu Photonics, Hamamatsu City, Japan) with a pixel dwell time of 0.79 µs. Final image magnification at the time of image capture was 1,890×, with each voxel representing 0.02 μm×0.02 μm×0.39 μm. A pinhole of 53.88 μm (~1 Airy unit for the red channel) was used for all color channels of all images. All images were captured at 2048×2048 pixels, saved in 8-bit .lsm image format, and converted to .tif format for analysis in the MacBiophotonics ImageJ package (McMaster University Biophotonics Facility, Hamilton, Ontario, Calif.). A median filter of 7×7 pixels was applied to EGFR images using Zeiss Zen 2011 Blue Edition (Carl Zeiss Microscopy GmbH, Gottingen, Germany) to reduce background noise. Co-localization of each image was determined using eight independent techniques. Standard overlays and intensity profile data were generated using Zen 2011, while six different co-localization analysis algorithms were performed using the JACoP and Colocalization Colormap plugins for ImageJ (National Institutes of Health, USA).

ImageJ was used for quantification of the Western blots, counting and estimation of chlamydial inclusion size and for the counting of the bound and internalized EBs (inside out studies). To define the chlamydial inclusion number and size, at least fifteen random fields were analyzed for each result. The number of inclusions was calculated per $10^5$ cells and expressed as a percentage of the respective controls. Similarly, fifteen random fields (3-10 cells per field) were used for the inside out experiments. All results are presented as mean±SEM. A t-test was used for comparisons and calculating the level of significance using SigmaPlot version 12.0.

Example 2

Identification of Cancer Relevant Biomarkers of Infection using Western Blot (WB) and Quantitative Mass Spectrometry (MS)

Figure 30:
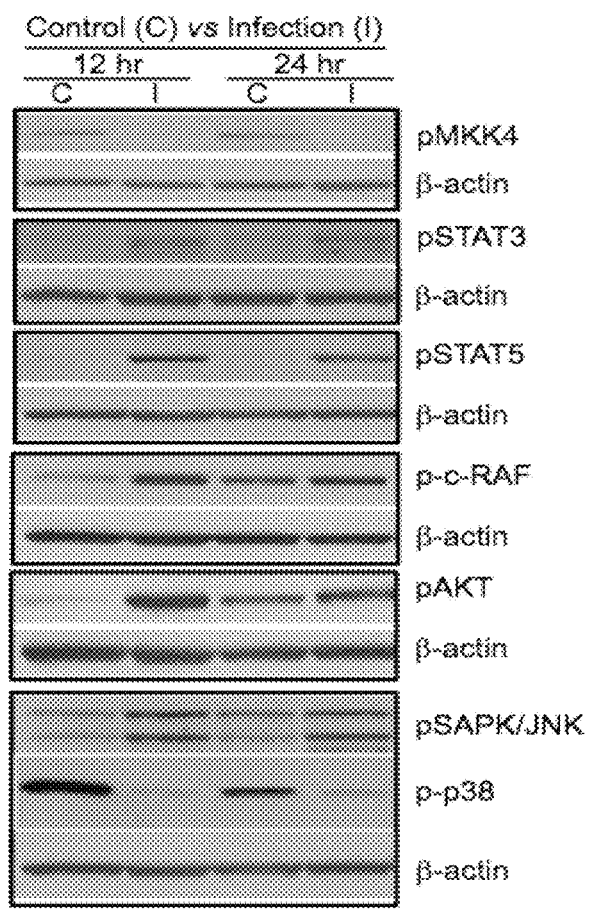
FIG. 30. *C. trachomatis*-induced regulation of protein phosphorylation in J774A.1 macrophages.

We initiated a series of targeted and discovery screening experiments to evaluate changes in protein, protein phosphorylation and protein oxidation in cells infected with *C. trachomatis*. Targeted analysis for a number of key signaling proteins is shown in FIG. 30. Important for this disclosure, the results revealed down-regulation of MKK4 at 12 and 24 hpi (hours post-infection) with *C. trachomatis* (FIG. 30). MKK4 is an important suppressor of metastasis. Down-regulation of MKK4 upon infection with *C. trachomatis* is significant for several reasons: i) it supports MKK4 as a potential biomarker of infection associated with unique developmental stages of *C. trachomatis* and cancer; ii) it opens opportunities for identifying MKK4-centered signaling networks that could be manipulated to prevent or combat chlamydial infections and cancer; and, iii) it could lead to the development of novel therapies to interfere with tumor metastasis. Since MKK4 is known to activate p38 and JNK pathways, we monitored phosphorylation of p38 and JNK. p38 phosphorylation decreased at 12 and 24 hpi as expected; however, JNK phosphorylation increased, suggesting compensatory mechanisms. In addition, *C. trachomatis* also induced phosphorylation of STAT3, STAT5, c-Raf and AKT. STAT3/5 can activate the Bcl-2 family of proteins, which leads to inhibition of mitochondrial cytochrome c release and down-regulation of apoptosis. The WB data suggest an anti-apoptotic, pro-proliferative state of *C. trachomatis* infected cells. STAT proteins are known mediators of angiogenesis and therefore important for tumor growth.

Summary of MS data. Comparative Western analysis can provide insight into specific molecular features of host-pathogen interactions; however, because of the limited linear range of detection, it is not feasible to apply this or other antibody-based technologies to quantitative, wide-scale investigations of global proteomic changes. Mass spectrometry (MS) has emerged as an alternative technology for quantitative, high-throughput studies of complex biological samples. Label-free quantitation, stable isotope dilution and stable isotope labeling with amino acids in cell culture (SILAC) are the top methods of quantification in MS studies of biological systems. MS has previously been applied to investigate host-pathogen interaction in cancer (e.g., *H. pylori*). No such studies have been reported for HPV or *C. trachomatis*.

Figure 31:
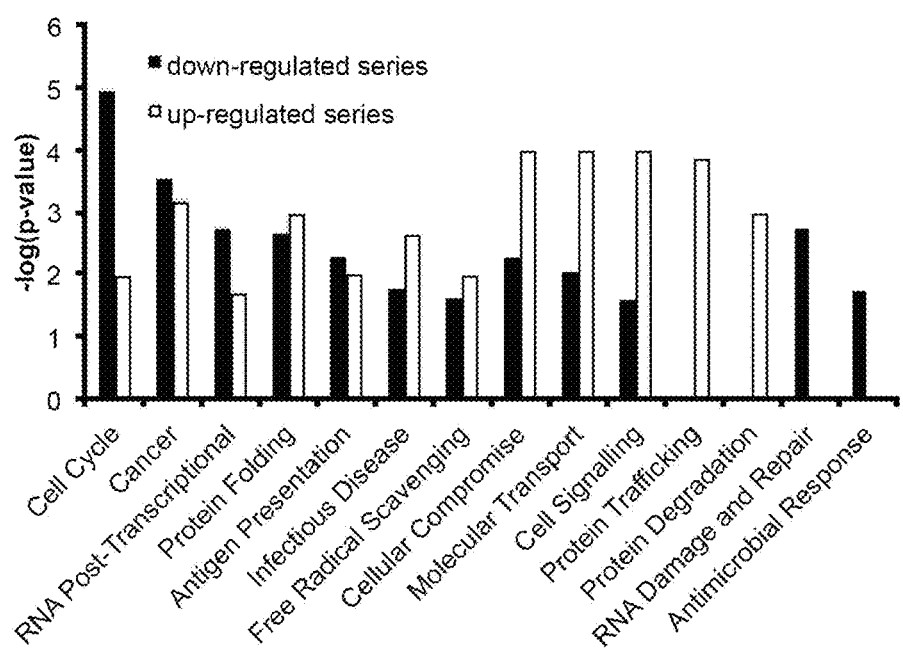
FIG. 31. Ingenuity Pathway Analysis of proteins that were up or down regulated in SQ-20B upon infection with *C. trachomatis*. A. Summary of top functions. B. Protein mapping to G2/M checkpoint pathway.
Figure 31:
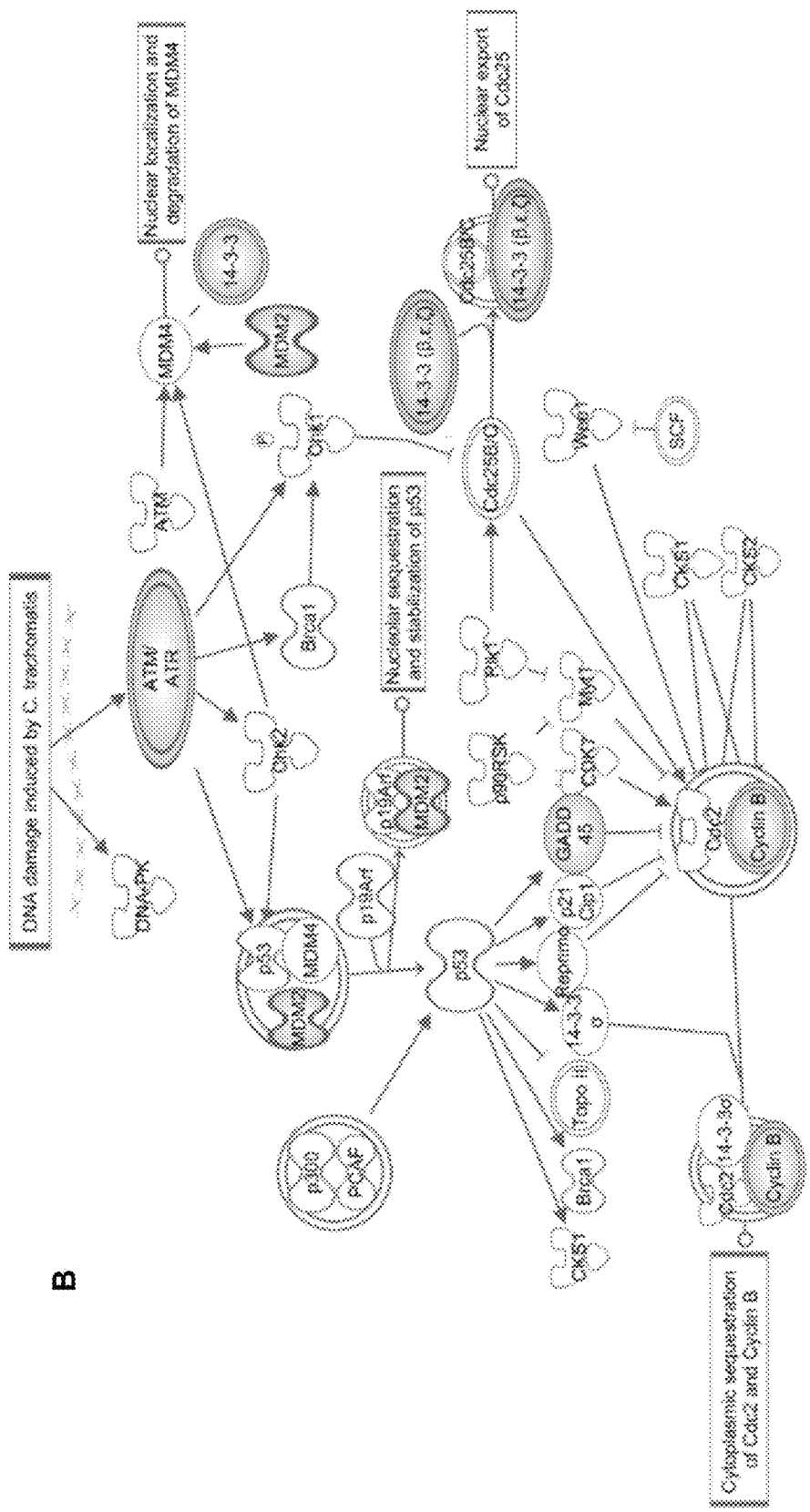

We thus ran a series of preliminary experiments to determine the effects of *C. trachomatis* infection on head and neck cancer. Proteomic changes induced by *C. trachomatis* in SQ-20B (head and neck cancer cell line) were quantified using mass spectrometry and SILAC (uninfected Arg0/Lys0, infected (24 hpi) Arg10/Lys8) and data were analyzed using Ingenuity Pathways Analysis (Ingenuity® Systems). A total of 221 mapped IDs were identified as down-regulated and 195 as up-regulated by infection with *C. trachomatis* at 24 hpi (threshold of fold-change set at 1.5). The contribution of these to various molecular and cellular functions is shown in FIG. 31, Panel A. Interestingly, the top diseases these proteins mapped to were cancer and infectious diseases. Because *C. trachomatis* has been reported to cause centrosomal defects, we were intrigued to find an imbalance in down-regulation of proteins involved in cell cycle control. In particular, regulation of the G2/M checkpoint is important for maintaining genomic stability and preventing cells from undergoing malignant transformation. Proteins that were down- or up-regulated by *C. trachomatis* were mapped to the G2/M checkpoint pathway shown in FIG. 31, Panel B. Down-regulated proteins relevant to control of cell cycle were: ATR, cyclin B1, GADD45 (highlighted in FIG. 31, Panel B), and MDM1, an isoform of MDM2 (FIG. 31, Panel B). MDM1 has not yet been characterized with respect to its function in cell cycle control. MDM2's function is to sequester p53, and MDM1 could potentially have a similar role. Two proteins were up-regulated, YWHAE and RbL1 at 24 hpi (FIG. 31, Panel B). RbL1 is relevant to regulation of the G1/S checkpoint.

To determine whether any of the *C. trachomatis*-regulated proteins in our dataset have biomarker potential, the dataset was filtered using IPA Biomarker filter with the following restrictions: cancer-relevant, application for diagnosis and monitoring of disease progression, and presence in biofluids that are readily available (plasma/serum and saliva). Nine of the proteins that were down-regulated and six of those up-regulated passed the cancer biomarker filter. Among these were heat shock protein 70 kDa (HSPA8), mitochondrial superoxide dismutase 2, and endothelial nitric oxide synthase 3 (all up-regulated), and alpha-fetoprotein, apolipoprotein A-1, early growth response 1, peroxiredoxin 3, and MKI67-antigen identified by monoclonal antibody Ki-67 (all down-regulated). Studies using clinical specimens are ongoing to further verify these as emerging biomarkers of *Chlamydia* infection.

*C. trachomatis* infection induces reactive oxygen species (ROS) and this is EGFR-dependent. Previous studies have shown that human cervical pre-neoplastic and neoplastic lesions are characterized by decreased catalase activity accompanied by an increase in $H_2O_2$. *C. trachomatis* is known to increase ROS in host cells through a mechanism dependent on NADPH oxidase, an enzyme that catalyzes the electron transfer from NADPH to molecular oxygen to produce superoxide. EGFR and a number of other receptor tyrosine kinases are known activators of NADPH oxidase.

Figure 32:
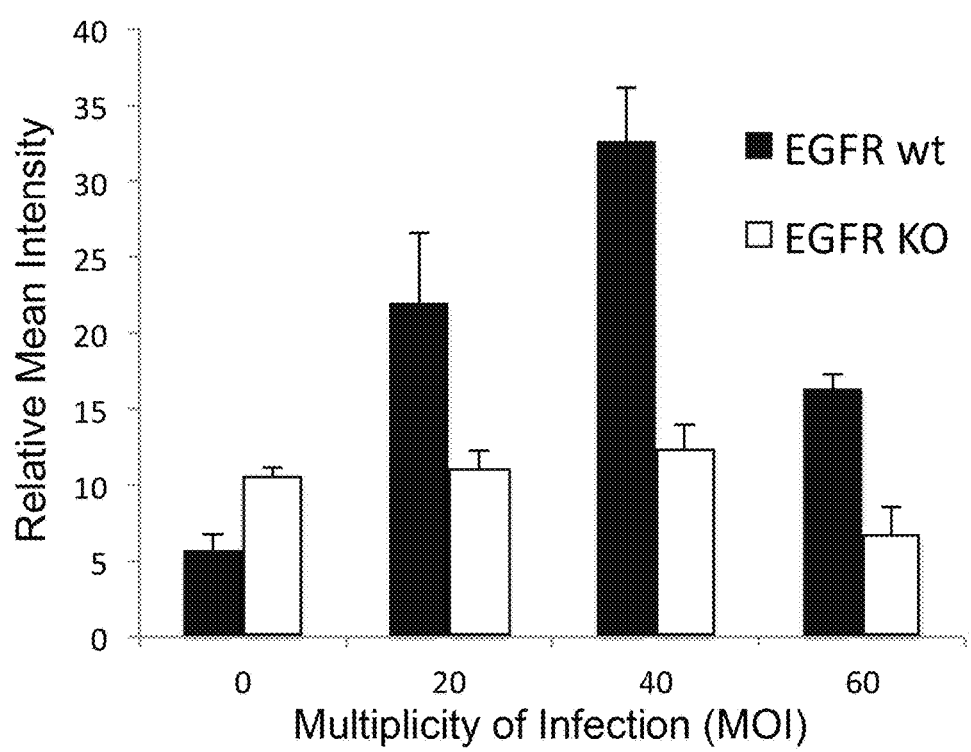
FIG. 32. *C. trachomatis* induces ROS production in EGFR wt MEFs but not in EGFR KO MEFs.

We asked whether *C. trachomatis*-induced ROS is dependent on EGFR. Data in FIG. 32 show the results of experiments performed in EGFR WT and EGFR KO MEFs. Cells were infected with *Chlamydia* at increasing multiplicity of infection (MOI) and the increase in ROS at 5 hpi was quantified using the fluorescent dye DCF (CM-H2DCFDA, Invitrogen) and imaging. A strong dependence of ROS on the MOI was observed in EGFR WT compared with KO cells. This confirms EGFR-dependent activation of NADPH oxidase as the major source of ROS in infected cells.

Figure 33:
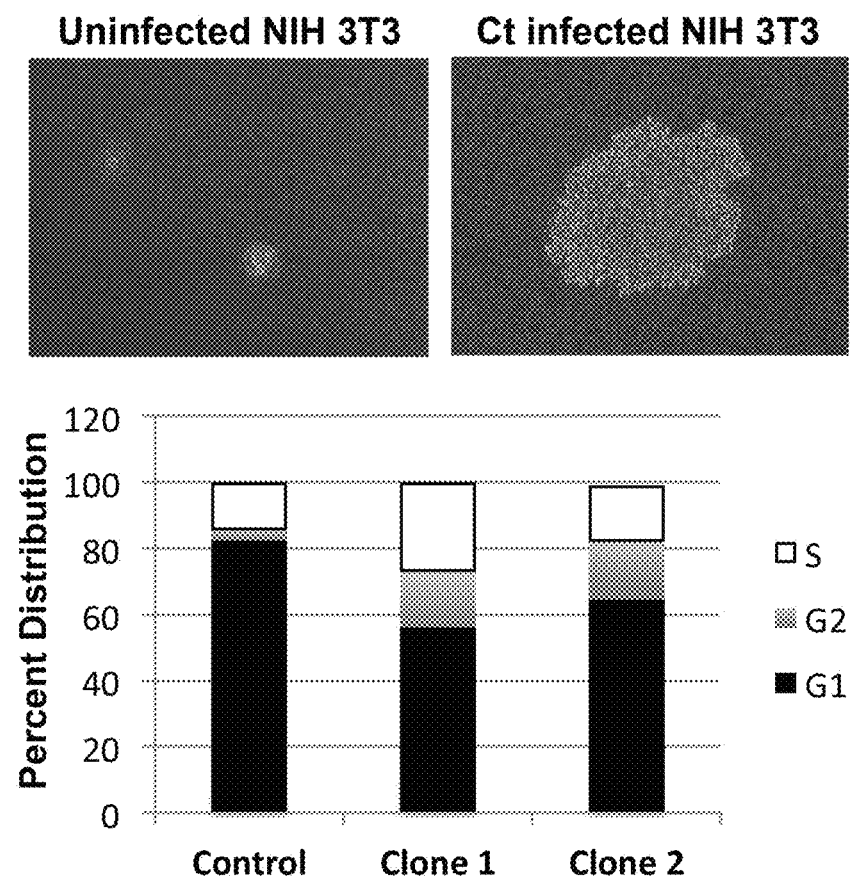
FIG. 33. Anchorage-independent growth of Ct infected NIH 3T3 cells. Upper: Colony formation using soft agar assay. Bottom: Cell cycle analysis of two transformed cell colonies picked from the soft agar.

Infection with *C. trachomatis* induces cell transformation. Many studies show a good correlation between in vitro cell transformation by cancer-inducing agents and tumor development in vivo. For example, HPV's potential to induce cell transformation established this viral pathogen as a causative factor for cervical and head and neck cancer. The most stringent and common test for cell transformation is to monitor anchorage-independent growth as colony formation in soft agar. We applied this method to monitor colony growth of Ct infected and uninfected NIH 3T3 cells (FIG. 33). In comparison to the control NIH 3T3 cells (upper panel, left), large colonies were observed for *C. trachomatis*-infected NIH 3T3 cells (upper panel, right) after four weeks of incubation. We analyzed two of these clones with respect to cell cycle distribution. In comparison to the control, increased cell population in G2/S phase of the cell cycle was observed in transformed NIH 3T3 clones. This is the first evidence of cell transformation by *C. trachomatis* alone, supporting the tumor-inducing potential of this bacterial pathogen.

The foregoing is illustrative of the present invention, and is not to be construed as limiting thereof. The invention is defined by the claims provided herein, with equivalents of the claims to be included therein.

All publications, patent applications, patents, patent publications, sequences identified by GenBank® Database accession numbers and/or SNP accession numbers, and other references cited herein are incorporated by reference in their entireties for the teachings relevant to the sentence and/or paragraph in which the reference is presented.

What is claimed is:

1. A method of treating a vaginal chlamydial infection or pelvic inflammatory disease in a subject, comprising administering to the subject an effective amount of Erlotinib, Cetuximab, Gefitinib, Lapatinib, Canertinib, Vandetanib and any combination thereof.

2. The method of claim 1, further comprising administering to the subject an antibiotic, a chemotherapeutic agent, an anti-inflammatory agent, an immunomodulatory agent and/or radiation, in any combination.

* * * * *

UNITED STATES PATENT AND TRADEMARK OFFICE
CERTIFICATE OF CORRECTION

PATENT NO. : 10,017,768 B2
APPLICATION NO. : 15/153401
DATED : July 10, 2018
INVENTOR(S) : Tsang et al.

Page 1 of 1

It is certified that error appears in the above-identified patent and that said Letters Patent is hereby corrected as shown below:

In the Specification

Column 9, Line 58: Please correct "(Icon)" to read -- (Icorr) --

Column 16, Line 30: Please correct "RbL 1" to read -- RbL1 --

Column 24, Line 53: Please correct "EFGR$^{+/+}$" to read -- EGFR$^{+/+}$ --

Column 28, Line 12: Please correct "EGFR$^{+/+}$" to read -- EGFR$^{-/-}$ --

Column 29, Line 21: Please correct "PDGFRIβ" to read -- PDGFRβ --

Signed and Sealed this
Ninth Day of October, 2018

Andrei Iancu
*Director of the United States Patent and Trademark Office*